US012545924B2

(12) United States Patent
Crawford

(10) Patent No.: US 12,545,924 B2
(45) Date of Patent: Feb. 10, 2026

(54) MUTATION OF GROWTH REGULATING FACTOR FAMILY TRANSCRIPTION FACTORS FOR ENHANCED PLANT GROWTH

(71) Applicant: Pairwise Plants Services, Inc., Durham, NC (US)

(72) Inventor: Brian Charles Wilding Crawford, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 18/609,099

(22) Filed: Mar. 19, 2024

(65) Prior Publication Data

US 2024/0263189 A1 Aug. 8, 2024

Related U.S. Application Data

(62) Division of application No. 17/126,469, filed on Dec. 18, 2020, now Pat. No. 11,965,170.

(60) Provisional application No. 62/951,593, filed on Dec. 20, 2019.

(51) Int. Cl.
*C12N 15/82* (2006.01)

(52) U.S. Cl.
CPC ..... *C12N 15/8262* (2013.01); *C12N 15/8213* (2013.01)

(58) Field of Classification Search
None
See application file for complete search history.

(56) References Cited

U.S. PATENT DOCUMENTS

2006/0174380 A1 8/2006 Carrington et al.
2015/0143581 A1 5/2015 Liu et al.
2015/0315605 A1 11/2015 Li et al.

FOREIGN PATENT DOCUMENTS

CN 110157730 A 8/2019
WO 2012149316 A2 11/2012
WO 2013102762 A1 7/2013
WO WO-2019158911 A1 * 8/2019 ........... A01H 6/4636
WO 2021004269 A1 1/2021

OTHER PUBLICATIONS

Nelissen et al. "Dynamic Changes in ANGUSTIFOLIA3 Complex Composition Reveal a Growth Regulatory Mechanism in the Maize Leaf" 2015 Plant Cell 27:1605-1619. (Year: 2015).*
International Search Report and the Written Opinion of the International Searching Authority corresponding to International Patent Application No. PCT/US2022/033701 mailed Nov. 25, 2022 (21 pages).
International Search Report and Written Opinion corresponding to PCT/US2020/065858; dated May 7, 2021 (20 pages).

(Continued)

*Primary Examiner* — Matthew R Keogh
*Assistant Examiner* — Rebecca Stephens
(74) *Attorney, Agent, or Firm* — Myers Bigel, P.A.

(57) ABSTRACT

This invention relates to compositions and methods for modifying Growth Regulating Factor (GRF) family transcription factors in plants to produce plants having improved phenotypic characteristics including increased growth. The invention further relates to plants produced using the methods and compositions of the invention.

8 Claims, 9 Drawing Sheets

Specification includes a Sequence Listing.

(56) References Cited

OTHER PUBLICATIONS

Chandran, Viswanathan , et al., "miR396-OsGRFs Module Balances Growth and Rice Blast Disease-Resistance", Front. Plant Sci. 9, Article No. 1999, 2019, 1-16.
Chen, Feng , et al., "Genome-wide identification of GRF transcription factors in soybean and expression analysis of GmGRF family under shade stress", BMC Plant Biology. 19:269 (2019).
Hu, Jiang , et al., "A Rare Allele of GS2 Enhances Grain Size and Grain Yield in Rice", Molecular Plant 8(10), 2015, 1455-1465.
Li, Shan , et al., "Modulating plant growth-metabolism coordination for sustainable agriculture", Nature, 560, 2018, 595-600.
Liebsch, Daniela , et al., "MicroRNA miR396, GRF transcription factors and GIF co-regulators: a conserved plant growth regulatory module with potential for breeding and biotechnology", Current Opinion in Plant Biology, 53, 2020, 31-42.
Liu, Jing , et al., "The BnGRF2 gene (GRF2-like gene from *Brassica napus*) enhances seed oil production through regulating cell number and plant photosynthesis", Journal of Experimental Botany 63(1), 2012, 3727-3740.
Liu, Weican , et al., "Tissue-Specific Regulation of Gma-miR396 Family on Coordinating Development and Low Water Availability Responses", Frontiers in Plant Science. 8:1112 (2017).
Nelissen, Hilde , et al., "Dynamic Changes in ANGUSTIFOLIA3 Complex Composition Reveal a Growth Regulatory Mechanism in the Maize Leaf", The Plant Cell. 27: 1605-1619 (2015).
Noon, Jason B., et al., "Homeostasis in the soybean miRNA396-GRF network is essential for productive soybean cyst nematode infections", Journal of Experimental Botany 70(5), 2019, 1653-1668.
Soto-Suárez, Mauricio , et al., "The *Arabidopsis* miR396 mediates pathogen-associated molecular pattern-triggered immune responses against fungal pathogens", Scientific Reports 9, Article No. 44898, 2017, 1-14.
Van Daele, Inge , et al., "A comparative study of seed yield parameters in *Arabidopsis thaliana* mutants and transgenics", Plant Biotechnology Journal 10(4), 2012, 488-500.
NCBI Reference Sequence: NM_001371441.1 "Glycine max growth-regulating factor (GRF2), mRNA" NCBI (2 pages) (Apr. 30, 2021).
Extended European Search Report corresponding to European Patent Application No. 20903876.9 (11 pages) (dated Jun. 11, 2024).
"Predicted: Glycine max growth-regulating factor (GRF10), mRNA—Nucleotide" NCBI (2 pages) (Apr. 19, 2021).

* cited by examiner

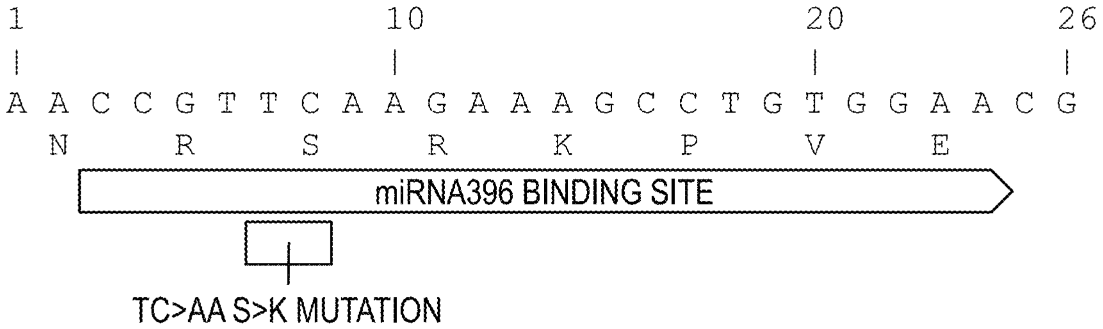

*FIG. 1*

| Name | Sequence / Translation | Mutation |
|---|---|---|
| Zm GRF6 TGTGG (WILDTYPE) | AACCGTTCAAGAAAGCCTGTGGAAACG | |
| FRAME 1 | N R S R K P V E T | |
| Zm GRF6 TGTAA | AACCGTTCAAGAAAGCCTGTAAAAACG | |
| FRAME 1 | N R S R K P V K T | GG>AA |
| Zm GRF6 TATAA | AACCGTTCAAGAAAGCCTATAAAAACG | |
| FRAME 1 | N R S R K P I K T | GG>AA |
| Zm GRF6 TGTCA | AACCGTTCAAGAAAGCCTGTCAAAACG | |
| FRAME 1 | N R S R K P V K T | GG>CA |
| Zm GRF6 A AND TATAA | AACCGTTCAAAAAAGCCTATAAAAACG | |
| FRAME 1 | N R S K K P I K T | G>A; GG>AA |
| Zm GRF6 TCTCA | AACCGTTCAAGAAAGCCTCTCAAAACG | |
| FRAME 1 | N R S R K P L K T | GG>CA |
| Zm GRF6 TGTAC | AACCGTTCAAGAAAGCCTGTACAAACG | |
| FRAME 1 | N R S R K P V Q T | GG>AC |
| Zm GRF6 A AND TGTGG | AACCGTTCAAAAAAGCCTGTGGAAACG | |
| FRAME 1 | N R S K K P V E T | G>A |
| Zm GRF6 A AND TGTAA | AACCGTTCAAAAAAGCCTGTAAAAACG | |
| FRAME 1 | N R S K K P V K T | G>A; GG>AA |

*FIG. 2*

| SEQUENCE | PAM | SCORE | GENE |
|---|---|---|---|
| TTTCCACAGGCTTTCTTGAA | CGG | 100.0 | GRMZM5G893117 |
| TTTCCACAGGCTTTCTTGAA | CGG | 100.0 | GRMZM2G034876 |
| CTTCCACAGGCTTTCTTGAA | CGG | 100.0 | GRMZM2G045977 |
| TTTCCACAGGCTTTCTTGAA | CGG | 100.0 | GRMZM2G033612 |
| CTTCCACAGGCTTTCTTGAA | CGG | 100.0 | GRMZM2G129147 |
| TTTCCACAGGCTTTCTTGAA | CGG | 100.0 | GRMZM2G105335 |
| CTTCCACAGGCTTTCTTGAA | CGG | 100.0 | GRMZM2G124566 |
| TTTCCACAGGCTTTCTTGAA | CGG | 100.0 | GRMZM2G018414 |
| CTTCCACAGGCTTTCTTGAA | CGG | 100.0 | GRMZM2G041223 |
| ATTCCACAGGCTTTCTTGAA | CGG | 100.0 | GRMZM2G119359 |
| CTTCCACAGGCTTTCTTGAA | CGG | 100.0 | GRMZM2G067743 |
| CTTCCACAGGCTTTCTTGAA | CGG | 100.0 | GRMZM5G850129 |
| ATTCCACAGGCTTTCTTGAA | CGG | 100.0 | GRMZM2G098594 |

FIG. 7

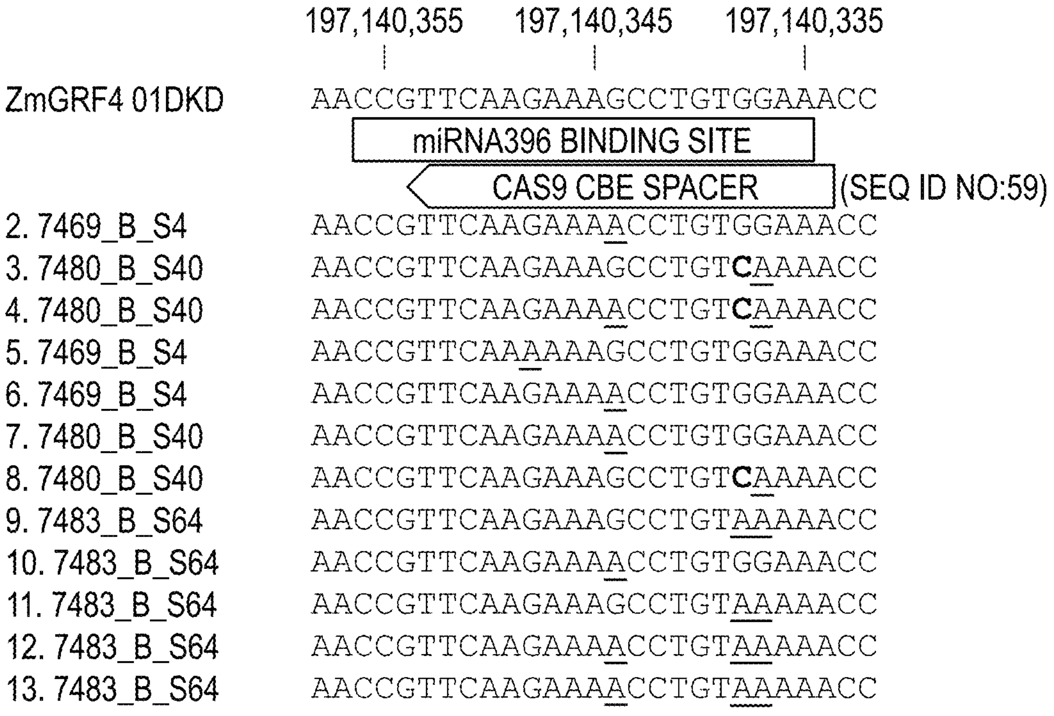

FIG. 8

| SEQUENCE | PAM | SCORE | GENE |
|---|---|---|---|
| CACAGGCTTTCTTGAACGGTTCT | TTTC | 100.0 | GRMZM5G893117 |
| CACAGGCTTTCTTGAACGGTTGC | TTTC | 100.0 | GRMZM2G034876 |
| CACAGGCTTTCTTGAACGGTGAC | TTTC | 100.0 | GRMZM2G033612 |
| CACAGGCTTTCTTGAACGGTTCT | TTTC | 100.0 | GRMZM2G105335 |
| CACAGGCTTTCTTGAACGGTGGC | TTTC | 100.0 | GRMZM2G018414 |
| CACAGGCTTTCTTGAACTGTGAA | TTTC | 50.0 | GRMZM2G092607 |

*FIG. 11*

MUTATION OF GROWTH REGULATING FACTOR FAMILY TRANSCRIPTION FACTORS FOR ENHANCED PLANT GROWTH

STATEMENT OF PRIORITY

This application is a continuation of and claims priority to U.S. application Ser. No. 18/541,481 filed Dec. 15, 2023, and the benefit, under 35 U.S.C. § 119 (e), of U.S. Provisional Application No. 62/951,593 filed on Dec. 20, 2019, the entire contents of each of which is incorporated by reference herein.

STATEMENT REGARDING ELECTRONIC FILING OF A SEQUENCE LISTING

A Sequence Listing in XML text format, submitted under 37 C.F.R. § 1.821-1.834, entitled 1499.16DV_ST26.xml, 522,375 bytes in size, generated on Mar. 16, 2024, and filed electronically, is provided in lieu of a paper copy. This Sequence Listing is hereby incorporated herein by reference into the specification for its disclosures.

FIELD OF THE INVENTION

This invention relates to compositions and methods for modifying growth regulating factor (GRF) family transcription factors in plants to produce plants having improved phenotypic characteristics including increased growth. The invention further relates to plants produced using the methods and compositions of the invention.

BACKGROUND OF THE INVENTION

GRFs are land-plant-specific transcription factors that function with GRF-interacting factors (GIFs), which are found in plants and metazoans but not in fungi. The number of GRF family members is about 8-20 across the land plants. Recent studies have uncovered the functions of GRFs in other aspects of plant biology such as flowering, seed and root development, the control of growth under stress conditions, and the regulation of plant longevity.

Analysis of GRF mutants and overexpressing plants have shown that these transcription factors promote cell proliferation during leaf development. It has also been established that the mRNA of some GRFs are targeted by the microRNA miR396. For example, seven out of the nine *Arabidopsis* GRFs have a binding site for micro-RNA (miRNA) miR396. While initial work on the GRF transcription factor family focused on the effect of GRF mis-expression on leaf size, later work established that larger seeds can be achieved in *Arabidopsis* by heterogeneous expression of *Brassica napus* GRF2 or overexpression of AtGRF1, AtGRF2 and AtGRF5 (van Daele et al. *Plant Biotechnology Journal* 10:488-500 2012)).

Grain size is one of the key components of grain yield and is regulated by quantitative trait loci (QTLs) in rice. A semi-dominant QTL for grain size and weight (GS2) have been reported in rice, which encodes the transcription factor OsGRF4 (GROWTH-REGULATING FACTOR 4) and is regulated by OsmiR396. A 2 bp substitution mutation in GS2 perturbs OsmiR396-directed regulation of GS2, resulting in large and heavy grains and increased grain yield (FIG. 1).

SUMMARY OF THE INVENTION

One aspect of the invention provides a plant or plant part thereof comprising at least one non-natural mutation in an endogenous gene encoding a Growth Regulating Factor (GRF) transcription factor, wherein the at least one non-natural mutation in the endogenous gene encoding a GRF transcription factor results in increased levels of mRNA produced by the endogenous gene.

Another aspect of the invention provides a plant cell, comprising a base editing system comprising: (a) a CRISPR-associated effector protein; (b) a cytidine deaminase or adenosine deaminase; and (c) a guide nucleic acid (gRNA, gDNA, crRNA, crDNA) having a spacer sequence with complementarity to an endogenous target gene encoding a GRF transcription factor.

A further aspect of the invention provides a plant cell comprising at least one non-naturally occurring genomic modification within a miR396 binding site of a GRF transcription factor gene that prevents or reduces binding of the miR396 to the GRF transcription factor mRNA, wherein the genomic modification is a substitution, insertion or a deletion that is introduced using an editing system that comprises a nucleic acid binding domain that binds to a target site in the GRF transcription factor gene having the nucleotide sequence of any one of SEQ ID NOs: 4-18, 121-144, or 173-198.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs: 4, 5 and 9-18, wherein each of SEQ ID NOs: 4, 5 and 9-18 comprise a sequence having at least 90% sequence identity to SEQ ID NO:1, and the target gene is modified (e.g., mutated) within the sequence having at least 90% sequence identity to SEQ ID NO:1.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to the nucleotide sequence of SEQ ID NO:6 or SEQ ID NO:7, wherein each of SEQ ID NO:6 or SEQ ID NO:7 comprise a sequence having at least 90% sequence identity to SEQ ID NO: 2, and the target gene is modified (e.g., mutated) within the sequence having at least 90% sequence identity to SEQ ID NO: 2.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NO:8, wherein SEQ ID NO:8 comprises a sequence having at least 90% sequence identity to SEQ ID NO: 3, and the target gene is modified (e.g., mutated) within the sequence having at least 90% sequence identity to SEQ ID NO: 3.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs: 121-144, wherein each of SEQ ID NOs: 121-144 comprise a sequence having at least 90% sequence identity to any one of SEQ ID NOs: 145-146, and the target gene is modified (e.g., mutated) within the sequence having at least 90% sequence identity to any one of SEQ ID NO:145-146.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs: 173-198, wherein each of SEQ ID NOs: 173-198 comprise a sequence having at least 90% sequence identity to any one of SEQ ID NOs: 199-202, and the target gene is modified (e.g., mutated) within the sequence having at least 90% sequence identity to any one of SEQ ID NOs: 199-202.

An additional aspect of the invention provides a plant comprising a Growth Regulating Factor (GRF) transcription factor gene that comprises a mutation in any one of the nucleotide sequences of SEQ ID NOs: 1-33 and/or comprises the nucleotide sequence of any one of SEQ ID NOs: 34-41.

A further aspect of the invention provides a corn plant comprising a Growth Regulating Factor (GRF) transcription factor gene that comprises a nucleotide sequence of any one of SEQ ID NOs: 34-42.

An additional aspect of the invention provides a maize plant comprising a mutation in the miR396 binding site of a Growth Regulating Factor (GRF) transcription factor gene, the GRF transcription factor gene comprising a nucleotide sequence of any one of SEQ ID NOs: 1 33.

An additional aspect of the invention provides a wheat plant comprising a mutation in the miR396 binding site of a Growth Regulating Factor (GRF) transcription factor gene, the GRF transcription factor gene comprising a nucleotide sequence of any one of SEQ ID NOs: 147-202.

A further aspect of the invention provides a soybean plant comprising a mutation in the miR396 binding site of a Growth Regulating Factor (GRF) transcription factor gene comprising a nucleotide sequence of any one of SEQ ID NOs: 97-146.

The invention further provides a method of producing/breeding a transgene-free base-edited plant, comprising: (a) crossing a plant of the invention with a transgene free plant, thereby introducing the at least one mutation, the mutation, or the modification into the plant that is transgene-free; and (b) selecting a progeny plant that comprises the at least one single nucleotide substitution but is transgene-free, thereby producing a transgene free base-edited plant.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 80% sequence identity to the nucleotide sequence of any one of SEQ ID NO: 4-18, 121-144, or 173-198, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 65% sequence identity to the nucleotide sequence of SEQ ID NO:9 or SEQ ID NO:14 and comprising a miR396 binding site sequence at bp position 21 to 42 of SEQ ID NO:9 (GRF8 60 nt cDNA or SEQ ID NO: 14 (GRF5 60 nt cDNA), the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs: 4, 5, or 9-18 and comprising a miR396 binding site sequence at bp position 21 to 42 of any one of SEQ ID NOs: 4, 5, or 9-18, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO: 6 or SEQ ID NO:7, and comprising a miR396 binding site sequence at bp position 21 to 42 of SEQ ID NO:6 or SEQ ID NO:7, the binding site sequence having at least 90% sequence identity to SEQ ID NO:2, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO: 8, and comprising a miR396 binding site sequence at bp position 21 to 42 of SEQ ID NO:8, the binding site sequence having at least 90% sequence identity to SEQ ID NO:3, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:4, and comprising a miR396 binding site sequence at bp position 21 to 42 of SEQ ID NO:4, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:5, and comprising a miR396 binding site sequence at bp position 21 to 42 of SEQ ID NO:5, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:9, and comprising a miR396 binding site sequence at bp position 21 to 42 of SEQ ID NO:9, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:10, and comprising a miR396 binding site sequence at bp position 21 to 42 of SEQ ID NO:10, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:11, and comprising a miR396 binding site sequence at bp position 21 to 42 of SEQ ID NO:1, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:12, and comprising a miR396 binding site sequence at bp position 21 to 42 of SEQ ID NO:12, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:13, and comprising a miR396 binding site sequence at bp position 21 to 42 of SEQ ID NO:13, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:14, and comprising a miR396 binding site sequence at bp position 21 to 42 of SEQ ID NO:14, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:15, and comprising a miR396 binding site sequence at bp position 21 to 42 of SEQ ID NO:15, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:16, and comprising a miR396 binding site sequence at bp position 21 to 42 of SEQ ID NO:16, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:17, and comprising a miR396 binding site sequence at bp position 21 to 42 of SEQ ID NO:17, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:18, and comprising a miR396 binding site sequence at bp position 21 to 42 of SEQ ID NO:18, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs: 121-144 and comprising a miR396 binding site sequence at bp position 21 to 42 of any one of SEQ ID NOs: 121-144, the binding site sequence having at least 90% sequence identity to any one of SEQ ID NOs: 145-146, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs: 173-198 and comprising a miR396 binding site sequence at bp position 21 to 42 of any one of SEQ ID NOs: 173-198, the binding site sequence having at least 90% sequence identity to any one of SEQ ID NOs: 199-202, thereby generating an edit in the endogenous GRF transcription factor gene of the plant cell.

An additional aspect of the invention provides a method for making a plant, comprising: (a) contacting a population of plant cells comprising an endogenous gene encoding a GRF transcription factor with an editing system comprising a nucleic acid binding domain that binds to a sequence having at least 80% identity to the nucleotide sequence of SEQ ID NOs: 1-3, 145, 146, or 199-202 or SEQ ID NOs: 4-18, 121-144, or 173-198; (b) selecting a plant cell from said population comprising a mutation in at least one endogenous gene encoding a GRF transcription factor, wherein the mutation is a substitution of at least one nucleotide in the at least one endogenous gene, wherein the mutation reduces or eliminates the ability of miR396 to bind to a mRNA produced by the at least one endogenous gene encoding a GRF transcription factor comprising the mutation; and (c) growing the selected plant cell into a plant.

In some aspects, the invention provides a method for producing a plant or part thereof comprising at least one cell in which an endogenous GRF transcription factor gene is mutated, the method comprising contacting a target site in the GRF transcription factor gene in the plant or plant part with an editing system comprising a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising at least one cell having a mutation in the endogenous GRF transcription factor gene A further aspect of the invention provides a method of producing a plant or part thereof comprising a mutated endogenous GRF transcription factor gene producing a mRNA having reduced miR396 binding, the method comprising contacting a target site in an endogenous GRF transcription factor gene with an editing system comprising a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising a mutated endogenous GRF transcription factor gene producing a mRNA having reduced miR396 binding.

Another aspect of the invention provides a method of producing a plant or part thereof having increased growth or an increased growth rate, the method comprising contacting a target site in an endogenous GRF transcription factor gene with an editing system comprising a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising a mutated endogenous GRF transcription factor gene that produces a mRNA having reduced miR396 binding, thereby producing a plant or part thereof having increased growth or an increased growth rate.

An additional aspect of the invention provides a guide nucleic acid (e.g., gRNA) that binds to a target site in a GRF transcription factor gene, the target site comprising any one of the nucleotide sequences of SEQ ID NOs: 44-71.

A further aspect of the invention provides a system comprising the guide nucleic acid of the invention and a CRISPR-Cas effector protein that associates with the guide nucleic acid.

Another aspect of the invention provides a gene editing system comprising a CRISPR-Cas effector protein in association with a guide nucleic acid, wherein the guide nucleic acid comprises a spacer sequence that binds to a GRF transcription factor gene.

An additional aspect of the invention provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one of SEQ ID NOs: 19-33, 97-120, or 147-172, wherein the nuclease cleaves the target strand.

An additional aspect of the invention provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one of SEQ ID NOs: 1-3, 145, 146, or 199-202, or SEQ ID NOs: 4-18, 121-144, or 173-198, wherein the nuclease cleaves the target strand.

Another aspect of the invention provides an expression cassette comprising a (a) polynucleotide encoding CRISPR-Cas effector protein comprising a cleavage domain and (b) a guide nucleic acid that binds to a target site in a GRF transcription factor gene, wherein the guide nucleic acid comprises a spacer sequence that is complementary to and binds to a sequence having at least 80% sequence identity to at least a portion of any one of the nucleotide sequences of SEQ ID NOs: 1-3, 145, 146, or 199-202, or SEQ ID NOs: 4-18, 121-144, or 173-198.

A further aspect of the invention provides a nucleic acid encoding a GRF transcription factor mRNA having a mutated miR396 binding site, wherein the mutated miR396 binding site comprises a mutation that disrupts miR396 binding and results in increased levels of the GRF transcription factor mRNA.

An additional aspect of the invention provides a corn plant or plant part thereof that comprises at least one non-natural mutation in at least one endogenous Growth Regulating Factor (GRF) transcription factor that is located in a defined chromosome interval on chromosome 1, 2, 4, 5, 6, 7, 9, and/or 10 of the corn plant, wherein the mutation disrupts the binding of miR396 to the GRF transcription factor mRNA resulting in increased levels of the GRF transcription factor mRNA.

Another aspect of the invention provides a guide nucleic acid that binds to a target nucleic acid in a GRF transcription factor in a corn plant, wherein the target nucleic acid is located in a defined chromosome interval on chromosome 1, 2, 4, 5, 6, 7, 9, and/or 10 of the corn plant.

Further provided are plants produced by the methods of the invention and comprising in their genome one or more mutated GRF transcription factor genes that produce mRNAs having a reduced ability to bind the corresponding miR396, as well as polypeptides, polynucleotides, nucleic acid constructs, expression cassettes and vectors for making a plant or part thereof this invention.

These and other aspects of the invention are set forth in more detail in the description of the invention below.

BRIEF DESCRIPTION OF THE SEQUENCES

SEQ ID NOs: 1-3 are miR396 binding site sequences in growth regulating factor (GRF) transcription factors from maize.

SEQ ID NOs: 4-18 are partial cDNA sequences of GRF transcription factors from maize.

SEQ ID NOs: 19-33 are full cDNA sequences of GRF transcription factors from maize.

SEQ ID NOs: 34-41 are examples of mutated miR396 binding site sequences of growth regulating factor (GRF) transcription factor 6 (GRF6).

SEQ ID NOs: 42-47 are GRF transcription factor proteins in, wild type (SEQ ID NO: 42) and mutant proteins (SEQ ID NOs: 43-47), respectively.

SEQ ID NOs: 48-71 show example spacer sequences.

SEQ ID NOs: 72-76, 209-213 are example adenosine deaminase sequences useful with this invention.

SEQ ID NOs: 77-80, 206-208 are example cytosine deaminase amino acid sequences useful with this invention.

SEQ ID NO:81 is an exemplary uracil-DNA glycosylase inhibitor (UGI) useful with this invention.

SEQ ID NO: 82-83 are exemplary regulatory sequences encoding a promoter and intron.

SEQ ID NOs: 84-96 are the mature miR396 sequences from maize.

SEQ ID NOs: 97-120 are full cDNA sequences of GRF transcription factors from soybean.

SEQ ID NOs: 121-144 are partial cDNA sequences of GRF transcription factors from soybean.

SEQ ID NOs: 145-146 are miR396 binding site sequence in growth regulating factor (GRF) transcription factors from soybean.

SEQ ID NOs: 147-172 are full cDNA sequences of GRF transcription factors from wheat.

SEQ ID NOs: 173-198 are partial cDNA sequences of GRF transcription factors from wheat.

SEQ ID NOs: 199-202 are miR396 binding site sequences of growth regulating factor (GRF) transcription factors from wheat.

SEQ ID NOs: 203-205 provides an example of a protospacer adjacent motif position for a Type V CRISPR-Cas12a nuclease.

SEQ ID NOs: 214-230 are exemplary Cas12a amino acid sequences useful with this invention.

SEQ ID NOs: 231-233 are exemplary Cas12a nucleotide sequences useful with this invention.

SEQ ID NOs: 234-250 are exemplary Cas12a nucleotide sequences useful with this invention.

BRIEF DESCRIPTION OF THE DRAWINGS

FIG. 1 shows a natural QTL controlling grain size and yield in rice. A 2 bp substitution removes mir396 binding of GRF4 in rice (top sequence: SEQ ID NO:252, bottom sequence: SEQ ID NO:253).

FIG. 2 shows base pair and amino acid changes observed in the E0 plants from an experiment with a CRISPR-CBE (CRISPR-Cas cytosine base editor). From top to bottom: SEQ ID NOs: 254, 42, 34, 43, 35, 44, 36, 43, 37, 45, 38, 255, 39, 46, 40, 256, 41 and 47.

(FIG. 4A top sequence: SEQ ID NO:4, bottom sequence: SEQ ID NO:260; FIG. 4B top sequence: SEQ ID NO:4, bottom sequence: SEQ ID NO:260).

FIG. 5B top sequence: SEQ ID NO:4, bottom sequence: SEQ ID NO:260).

FIG. 7 shows GRF6 and four other GRF loci targeted with 100% match to the spacer sequence. The Cas9 base editor spacer sequence (TTTCCACAGGCTTTCTTGAA SEQ ID NO: 58) targets several GRF transcription factors with 100% specificity. Other GRF transcription factor targets have miss-matches (underlined nucleotides) in the spacer target sequence. The target sequence, PAM, specificity score and target gene are shown. From top to bottom: SEQ ID NOs: 58, 58, 261, 58, 261, 58, 261, 58, 261, 262, 261, 261, and 262.

FIG. 8 shows Cas9 base edits in E0 plants. The wildtype GRF6 sequence is on top. The miR396 sequence is highlighted red, the spacer used for base edits blue (SEQ ID NO: 58). Individual NGS reads are below for plants 7469, 7480, and 7483. Edited bases are colored. Progeny from these plants were used for phenotypic analysis in subsequent plant generations. From top to bottom: SEQ ID NOs: 263, 264, 265, 266, 267, 264, 264, 265, 268, 264, 268, 269 and 269.

FIG. 11 shows that Cpf1 spacer CACAGGCTTTCTT-GAACGGTTGC (SEQ ID NO: 55) targets only GRF6 (GRMZM2G034876) with 100% specificity. Other GRF transcription factor targets have miss-matches (red nucleotides) in the spacer target sequence. The target sequence, PAM, specificity score and target gene are shown. From top to bottom: SEQ ID NOs: 270, 55, 271, 272, 273, and 274.

DETAILED DESCRIPTION

Figure 3:
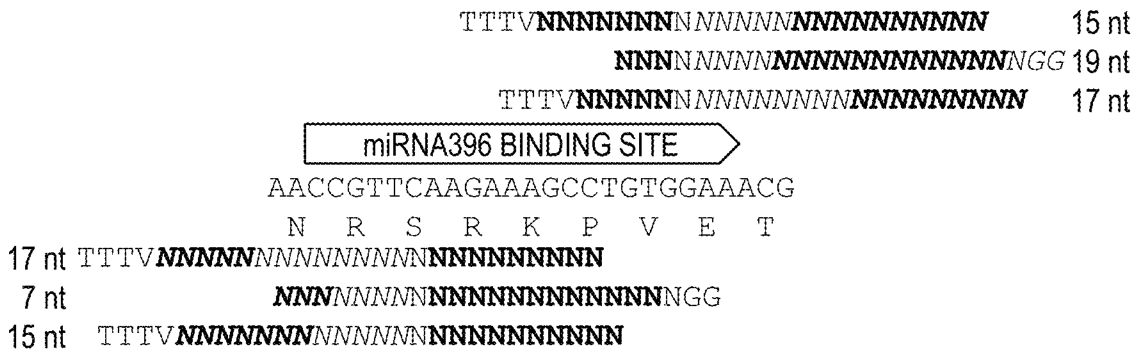
FIG. 3 shows an example editing window for a miR396 binding site. From top to bottom: SEQ ID NOs: 257, 258, 259, 254, 42, 257, 258, and 259.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms “a,” “an” and “the” are intended to include the plural forms as well, unless the context clearly indicates otherwise.

Also as used herein, “and/or” refers to and encompasses any and all possible combinations of one or more of the associated listed items, as well as the lack of combinations when interpreted in the alternative (“or”).

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term “comprise,” “comprises” and “comprising” as used herein, specify the presence of the stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

As used herein, the terms “increase,” “increasing,” “increased,” “enhance,” “enhanced,” “enhancing,” and “enhancement” (and grammatical variations thereof) describe an elevation of at least about 15%, 20%, 25%, 50%, 75%, 100%, 150%, 200%, 300%, 400%, 500% or more as compared to a control.

As used herein, the terms “reduce,” “reduced,” “reducing,” “reduction,” “diminish,” and “decrease” (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms “express,” “expresses,” “expressed” or “expression,” and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with with increased yield under non-water stress conditions" refers to a marker whose presence or absence can be used to predict whether a plant will display with increased yield under non-water stress conditions.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

As used herein, "increased growth" and/or "an increased growth rate" refers to any plant trait associated with growth, for example, biomass, yield, nitrogen use efficiency (NUE), inflorescence size/weight, fruit yield, fruit quality, fruit size, seed size, seed number, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, length of roots, number of roots, size and/or weight of root mass, or any combination thereof. Thus, in some aspects, "increased growth" and/or "an increased growth rate" may include, but is not limited to, increased inflorescence production, increased fruit production (e.g., increased number, weight and/or size of fruit; e.g., increase number, weight, and/or size of ears for, e.g., maize), increased fruit quality, increased number, size and/or weight of roots, increased meristem size, increased seed size, increased biomass, increased leaf size, increased nitrogen use efficiency, increased disease resistance, increased height and/or increased internode length as compared to a control plant or part thereof (e.g., a plant that does not comprise a modified endogenous nucleic acid encoding a GFR transcription factor as described herein).

"Seed weight" is jointly determined by grain morphology traits such as seed length, seed width and seed thickness as well as grain filling and these traits are all governed by quantitative genetics.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like). In some embodiments, a nucleic acid fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more consecutive nucleotides of a nucleotide sequence encoding a GRF transcription factor.

In some embodiments, a fragment or portion may be a fragment or portion of a GRF transcription factor gene. In some embodiments, a fragment or portion may be a fragment or portion of any one of the nucleotide sequences of SEQ ID NOs: 4-18, 121-144, or 173-198, wherein the fragment or portion comprises about 5, 6, 7, 8, 9, 10, 11, 12, 13, 14, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 consecutive nucleotides, or any range or value therein of any one of the nucleotide sequences of SEQ ID NOs: 4-18, 121-144, or 173-198. In some embodiments, a fragment or portion may be a fragment or portion of the nucleotide sequence of any one of SEQ ID NOs: 4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs: 4-18, 121-144, or 173-198. In some embodiments, an example fragment or portion of any one of the nucleotide sequences of SEQ ID NOs: 4-18, 121-144, or 173-198 may be a fragment or portion comprising consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs: 4-18, 121-144, or 173-198 (counted from the 5' end). In some embodiments, a fragment or portion of any one of the nucleotide sequences of SEQ ID NOs: 4-18, 121-144, or 173-198 may be a fragment or portion comprising consecutive nucleotides from base pair position 20 to base pair position 42 of any one of the nucleotide sequences of SEQ ID NOs: 4-18, 121-144, or 173-198 (counted from the 5' end) . . . . In some embodiments, the at least a portion may comprise at least one nucleotide or at least two (e.g., 2, 3, 4, 5, 6, 7, 8, 9, 10, 11, 12, 13, 14, 15, 16, 17, 18, 19, 20, 21, or 22) consecutive nucleotides of any one of the nucleotide sequences of SEQ ID NOs: 4-18, 121-144, or 173-198).

In some embodiments, a sequence-specific DNA binding domain may bind to one or more fragments or portions of nucleotide sequences as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400 or more consecutive amino acids of a reference polypeptide. In some embodiments, a polypeptide fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700 or more consecutive amino acid residues of a GRF transcription factor.

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments, such as Southern and Northern hybridizations, are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific DNA binding domain (e.g., a sequence-specific DNA binding domain from a a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol*. Rep. 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, Ubi promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79:87-94), maize (Christensen et al., 1989. *Plant Molec. Biol.* 12:619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231:150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP U.S. Pat. No. 255,378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9 (5): 297-306 (2015)), ZmSTK2_USP from maize (Wang et al. *Genome* 60 (6): 485-495 (2017)), LAT52 and LAT59 from tomato (Twell et al. *Development* 109 (3): 705-713 (1990)), Zm13 (U.S. Pat. No. 10,421,972), $PLA_2$-δ promoter from arabidopsis (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37 (8): 1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g, SEQ ID NO:83 and SEQ ID NO:84).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific DNA binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific DNA binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a sequence specific DNA binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

The plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further and particularly emphasized examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CrylA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CrylF protein or hybrids derived from a CrylF protein (e.g. hybrid CrylA-CrylF proteins or toxic fragments thereof), the CrylA-type proteins or toxic fragments thereof, preferably the CrylAc protein or hybrids derived from the CrylAc protein (e.g. hybrid CrylAb-CrylAc proteins) or the CrylAb or Bt2 protein or toxic fragments thereof, the Cry2Ae, Cry2Af or Cry2Ag proteins or toxic fragments thereof, the CrylA. 105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), *Proc Natl Acad Sci US A*. 28; 93 (11): 5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated Arabidopsis ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties include but are not limited to increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRI (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insectcontrol-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 orWO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); EventEE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINI (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652);

Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No. PTA-11041) optionally stacked with event EE-GM1/LL27 or event EE-GM2/LL55 (WO2011/063413A2), event DAS-68416-4 (soybean, herbicide tolerance, ATCC Accession No. PTA-10442, WO2011/066360A1), event DAS-68416-4 (soybean, herbicide tolerance, ATCC Accession No. PTA-10442, WO2011/066384A1), event DP-040416-8 (corn, insect control, ATCC Accession No. PTA-11508, WO2011/075593A1), event DP-043A47-3 (corn, insect control, ATCC Accession No. PTA-11509, WO2011/075595A1), event DP-004114-3 (corn, insect control, ATCC Accession No. PTA-11506, WO2011/084621A1), event DP-032316-8 (corn, insect control, ATCC Accession No. PTA-11507, WO2011/084632A1), event MON-88302-9 (oilseed rape, herbicide tolerance, ATCC Accession No. PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No. available, WO2012071039Al), event DP-073496-4 (oilseed rape, herbicide tolerance, no deposit No. available, US2012131692), event 8264.44.06.1 (soybean, stacked herbicide tolerance, Accession No. PTA-11336, WO2012075426A2), event 8291.45.36.2 (soybean, stacked herbicide tolerance, Accession No. PTA-11335, WO2012075429A2), event SYHTOH2 (soybean, ATCC Accession No. PTA-11226, WO2012/082548A2), event MON88701 (cotton, ATCC Accession No. PTA-11754, WO2012/134808A1), event KK179-2 (alfalfa, ATCC Accession No. PTA-11833, WO2013/003558A1), event pDAB8264.42.32.1 (soybean, stacked herbicide tolerance, ATCC Accession No. PTA-11993, WO2013/010094A1), event MZDT09Y (corn, ATCC Accession No. PTA-13025, WO2013/012775A1).

The genes/events (e.g., polynucleotides of interest), which impart a desired trait may also be present in combinations with one another in a transgenic plant. Examples of transgenic plants include, but are not limited to, crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific DNA binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific DNA binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g. expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby sequence-specific DNA binding protein, the reverse transcriptase and the deaminase are expressed and the sequence-specific DNA binding protein binds to the target nucleic acid, and the reverse transcriptase and/or deaminase may be either fused to the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol.* Lett. 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

GRF transcription factors are involved in growth promotion in plants. The expression of GRF transcription factors can increase growth when they are ectopically or over expressed. One common mechanism to repress expression of the GRF transcription factors is through the microRNA, miR396. MicroRNAs are small non-coding RNA molecule found in plants, animals and some viruses, which function in RNA silencing and post-transcriptional regulation of gene expression. miRNAs function via base-pairing with complementary sequences within mRNA molecules. The present inventors have discovered that by changing the binding site of miRNA binding in a target mRNA it is possible to remove the ability of the miRNA to post-transcriptionally regulate the target genes expression.

Figure 6:
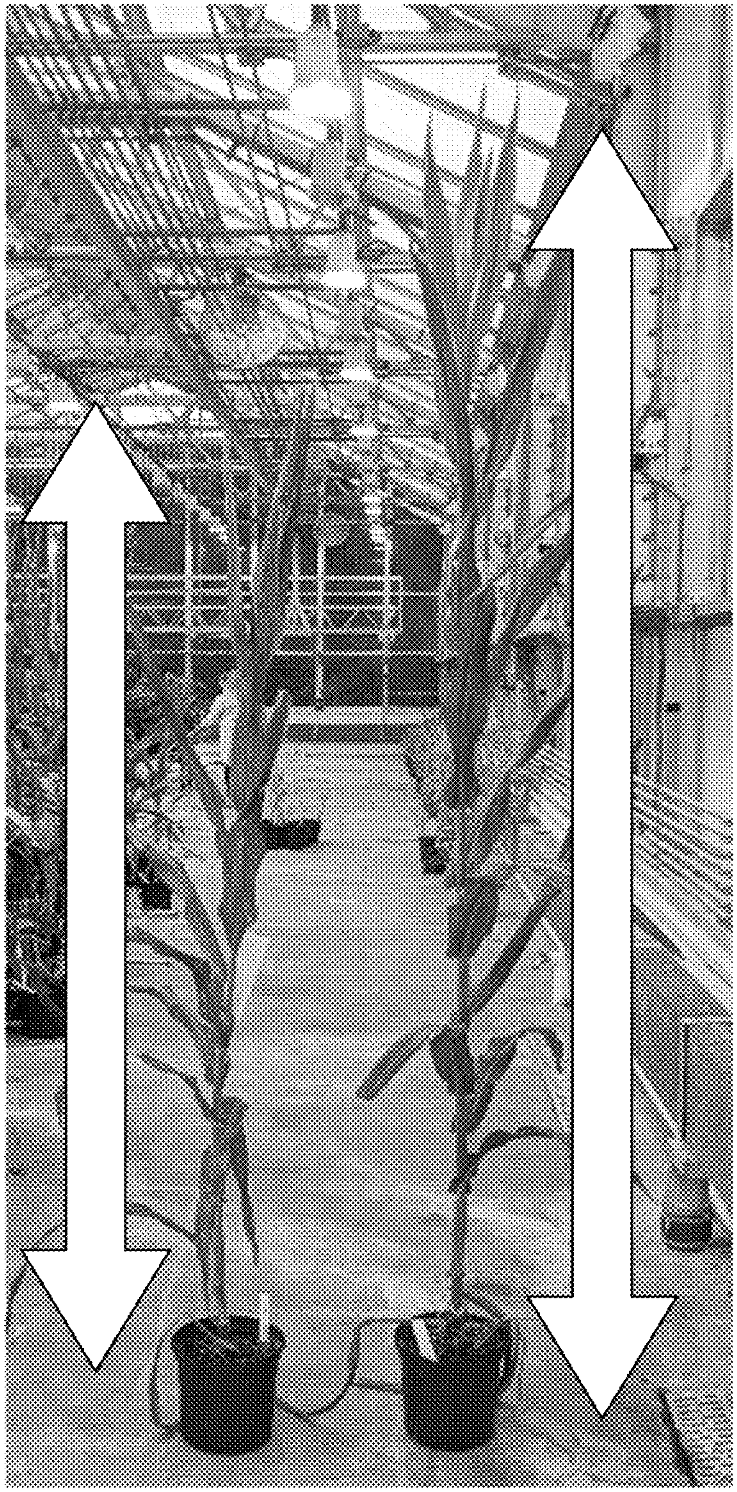
FIG. 6 shows the phenotype of an E1 corn plant having a mutation in a GRF transcription factor obtained using the methods and base editing compositions as described herein.

In some embodiments, a plant or plant part thereof is provided, the plant or part there of comprising at least one non-natural mutation in at least one gene encoding an endogenous Growth Regulating Factor (GRF) transcription factor, wherein the mutation disrupts the binding of miR396 to the mRNA that is produced by the at least one gene encoding the endogenous GRF transcription factor resulting in increased levels of the mRNA. In some embodiments, a mutation that disrupts the binding of miR396 to the GRF transcription factor mRNA and results in increased levels of the mRNA as described herein is a stable mutation, optionally wherein the mutation is in the miR396 binding site of the mRNA encoded by the GRF transcription factor gene (see, e.g., FIG. 3). In some embodiments, at least one non-natural mutation in at least one gene encoding an GRF transcription factor is a semi-dominant mutation and/or a hypomorphic mutation. In some embodiments, the endogenous GRF transcription factor that is mutated may include, but is not limited to, a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. The plant may be any plant as described herein. In some embodiments, the plant may be a wheat plant or a corn plant (see, e.g., Table 1). In some embodiments, GRF transcription factor may be from corn and may comprise a GRF6, GRF2, GRF1, GRF14, GRF15, GRF8, GRF4, GRF12, GRF10, GRF11, GRF5, GRF3, GRF9, GRF13, or a GRF7. In some embodiments, the corn plant may comprise a short stature/semi-dwarf phenotype (see, e.g., FIG. 6). In some embodiments, the at least one non-natural mutation in at least one gene encoding an endogenous GRF transcription factor in a wheat plant may be in the A genome, B genome, or D genome, or any combination thereof.

In some embodiments, a GRF transcription factor gene produces an mRNA that binds a corresponding miR396. In some embodiments, the corresponding miR396 may be a mir396a, a miR396b, a mir396c, a miR396d, a mir396e, a miR396f, a mir396g, and/or a miR396h (see, e.g., SEQ ID NOs: 84-96). In some embodiments, a GRF transcription factor mRNA binds a miR396a. In some embodiments, a GRF transcription factor mRNA binds a miR396b. In some embodiments, reduced miR396 binding to a GRF transcription factor mRNA may be measured by measuring the levels of the GRF transcription factor mRNA.

In some embodiments, the at least one non-natural mutation in at least one endogenous GRF transcription factor gene may be a base substitution, a deletion and/or an insertion. In some embodiments, the at least one mutation may be a synonymous mutation in the portion of the GRF transcription factor gene that produces the miRNA binding site of the GRF transcription factor mRNA. In some embodiments, at least one non-natural mutation in at least one gene encoding an GRF transcription factor is a semi-dominant mutation and/or a hypomorphic mutation. In some embodiments, the portion of the GRF transcription factor gene that produces the miR396 binding site in the GRF transcription factor mRNA encodes a portion of the endogenous GRF transcription factor polypeptide, wherein the portion of the endogenous GRF transcription factor polypeptide comprises the amino acid sequence of NRSRKPVET (SEQ ID NO: 42). In some embodiments, the at least one mutation may be a non-synonymous mutation in the nucleotide sequence that encodes a portion of the endogenous GRF transcription factor amino acid sequence, said portion having the amino acid sequence of NRSRKPVET (SEQ ID NO:42). In some embodiments, the at least one mutation may be an in-frame deletion in the nucleotide sequence that encodes a portion of the endogenous GRF transcription factor amino acid sequence, said portion having the amino acid sequence of NRSRKPVET (SEQ ID NO:42). Thus, in some embodiments the invention provides a plant cell comprising a stable and targeted (e.g., non-natural) single nucleotide substitution in an endogenous gene encoding a GRF transcription factor. In some embodiments, a mutation in an endogenous gene encoding a GRF transcription factor does not result in a mutation in the polypeptide sequence of the GRF transcription factor. In some embodiments, a mutation in an endogenous gene encoding a GRF transcription factor produces a polypeptide comprising a mutation in the polypeptide sequence of the GRF transcription factor. In some embodiments, a mutated GRF transcription factor polypeptide may comprise the amino acid sequence of NRSRKPVKT (SEQ ID NO:43), NRSRKPIKT (SEQ ID NO:44), NRSKKPIKT (SEQ ID NO:45), NRSRKPVQT (SEQ ID NO:46), and/or NRSKKPVKT (SEQ ID NO:47).

In some embodiments, an endogenous GRF transcription factor gene that produces an mRNA having a miR396 binding site comprises: (a) a nucleotide sequence having at least 90% sequence identity to any one of the nucleotide sequences of SEQ ID NOs: 1-3, 145, 146, or 199-202; (b) a nucleotide sequence having at least 95% identity (e.g., about 95, 96, 70, 98, 99, or 100%) to any one of the nucleotide sequences of SEQ ID NOs: 1-3, 145, 146, or 199-202; or (c) the nucleotide sequence set forth in any one of the nucleotide sequences of SEQ ID NOs: 1-3, 145, 146, or 199-202. In some embodiments, a base substitution can be a substitution of any base to any different base, e.g., to an A, T, C, or G. In some embodiments, the endogenous GRF transcription factor gene may comprise a mutation in at least one of positions 11, 19, 21 and/or 22 of any one of the nucleotide sequences of SEQ ID NOs: 1-3, 145, 146, or 199-202. In some embodiments, a mutation at position 11 of any one of the nucleotide sequences of SEQ ID NOs: 1-3, 145, 146, or 199-202 may be from G to A, T, or C (e.g., G>A, G>T, G>C), a mutation at position 19 of any one of the nucleotide sequences of SEQ ID NOs: 1-3, 145, 146, or 199-202 may be from G to A, T, or C, a mutation at position 21 of any one of the nucleotide sequences of SEQ ID NOs: 1-3, 145, 146, or 199-202 may be from G to A, T, or C and/or a mutation at position 22 of any one of the nucleotide sequences of SEQ ID NOs: 1-3, 145, 146, or 199-202 is from G to A, T, or C. In some embodiments, a mutation at position 11 of any one of the nucleotide sequences of SEQ ID NOs: 1-3, 145, 146, or 199-202 may be G>A. In some embodiments, a mutation at position 19 of any one of the nucleotide sequences of SEQ ID NOs: 1-3, 145, 146, or 199-202 may be G>A or G>C. In some embodiments, a mutation at position 21 of any one of the nucleotide sequences of SEQ ID NOs: 1-3, 145, 146, or 199-202 may be G>A or G>C. In some embodiments, a mutation at position 22 of any one of the nucleotide sequences of SEQ ID NOs: 1-3, 145, 146, or 199-202 may be G>A or G>C.

A mutation in an endogenous GRF transcription factor gene that comprises the nucleotide sequence of any one of SEQ ID NOs: 1-3, 145, 146, or 199-202 may or may not produce a change in the amino acid sequence. Thus, a mutation to an endogenous GRF transcription factor gene comprising the nucleotide sequence of any one of SEQ ID NOs: 1-3 may result in the same amino acid sequence of NRSRKPVET (SEQ ID NO:42). In some embodiments, a mutation to endogenous GRF transcription factor gene comprising the nucleotide sequence of any one of SEQ ID NOs: 1-3 may result in an amino acid sequence that can include, but is not limited to, the amino acid sequence of any one of NRSRKPVKT (SEQ ID NO:43), NRSRKPIKT (SEQ ID NO:44), NRSKKPIKT (SEQ ID NO:45), NRSRKPVQT (SEQ ID NO:46), and/or NRSKKPVKT (SEQ ID NO:47).

In some embodiments, the invention provides a plant cell, the plant cell comprising a base editing system comprising: (a) a sequence-specific binding domain (e.g., a CRISPR-associated effector protein); (b) a cytidine deaminase or adenosine deaminase; and (c) a guide nucleic acid (gRNA) having a spacer sequence with complementarity to an endogenous target gene encoding a GRF transcription factor. In some embodiments, an endogenous target gene encoding a GRF transcription factor may comprise at least about 90% sequence identity (e.g., about 90, 91, 92, 93, 94, 95, 96, 70, 98, 99, or 100%) to any one of the nucleotide sequences of SEQ ID NOs: 1-3, 145, 146, or 199-202. In some embodiments, a guide nucleic acid may comprise a spacer sequence having the nucleotide sequence of, for example, any one of SEQ ID NOs: 48-71.

In some embodiments, a guide nucleic acid useful with this invention may comprise spacer that is complementary to a fragment or portion of the nucleotide sequence of any one of SEQ ID NOs: 4-18, 121-144, or 173-198, wherein the fragment or portion of any one of SEQ ID NOs: 4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs: 4-18, 121-144, or 173-198. In some embodiments, a fragment or portion of any one of SEQ ID NOs: 4-18, 121-144, or 173-198 to which a spacer for a guide nucleic acid may be complementary may comprise consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs: 4-18, 121-144, or 173-198 (counted from the 5' end). In some embodiments, a spacer sequence for a guide nucleic acid may be complementary to consecutive nucleotides from base pair position 20 to base pair position 42 of any one of the nucleotide sequences of SEQ ID NOs: 4-18, 121-144, or 173-198 (counted from the 5' end). In some embodiments, a spacer sequence for a guide nucleic acid may comprise a spacer sequence having the nucleotide sequence of any one of SEQ ID NOs: 48-71.

In some embodiments, a plant part or plant cell produced by the methods of this invention may be regenerated to produce a plant comprising a stable mutation in at least one gene encoding an endogenous GRF transcription factor, wherein the mutation results in reduced binding of a corresponding miR396 to the mRNA that is produced by the endogenous GRF transcription factor gene, optionally wherein the mutation is a semi-dominant mutation and/or a hypomorphic mutation.

In some embodiments, the invention further provides a plant cell comprising at least one non-naturally occurring genomic modification within a miR396 binding site of a GRF transcription factor gene that prevents or reduces binding of the miR396 to the GRF transcription factor mRNA transcribed from the GRF transcription factor gene comprising the at least one non-natural genomic modification, wherein the genomic modification is a substitution, insertion or a deletion that is introduced using an editing system that comprises a nucleic acid binding domain that binds to a target site in the GRF transcription factor gene having the nucleotide sequence of any one of SEQ ID NOs: 4-18, 121-144, or 173-198.

In some embodiments, the invention provides a plant or part thereof comprising a mutated endogenous GRF transcription factor gene that produces an mRNA having reduced miR396 binding, wherein the mutated endogenous GRF transcription factor gene comprises a target gene (a target nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs: 4, 5 or 9-18, wherein each of SEQ ID NOs: 4, 5 or 9-18 comprise a sequence having at least 90% sequence identity (e.g., about 90, 91, 92, 93, 94, 95, 96, 70, 98, 99, or 100%) to SEQ ID NO:1, and the target gene is modified (e.g., mutated) within the sequence having at least 90% sequence identity to SEQ ID NO:1. In some embodiments, the modification (e.g., mutation) within the sequence having at least 90% sequence identity to the nucleotide sequence of SEQ ID NO:1 may be introduced using an editing system that comprises a sequence-specific DNA binding domain that binds to a target site within a nucleotide sequence having at least 80% identity to any one of the nucleotide sequences of SEQ ID NOs: 4, 5 or 9-18. In some embodiments, the modification within the sequence having at least 90% sequence identity to the nucleotide sequence of SEQ ID NO:1 may be introduced using an editing system that comprises a sequence-specific DNA binding domain that binds to a target site within the nucleotide sequence of any one of SEQ ID NOs: 19-33.

In some embodiments, a plant or part thereof is provided, the plant or plant part thereof comprising a mutated endogenous GRF transcription factor gene that produces a mRNA having reduced miR396 binding and resulting in increased levels of mRNA produced by the endogenous GRF transcription factor gene, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:6 or SEQ ID NO:7, wherein each of the nucleotide sequence of SEQ ID NO:6 or SEQ ID NO:7 comprise a sequence having at least 90% sequence identity to the nucleotide sequence of SEQ ID NO: 2, and the target gene is modified (e.g., mutated) within the sequence having at least 90% sequence identity (e.g., about 90, 91, 92, 93, 94, 95, 96, 70, 98, 99, or 100%) to the nucleotide sequence of SEQ ID NO: 2. In some embodiments, the modification (e.g., mutation) within the sequence having at least 90% sequence identity to SEQ ID NO: 2 may be introduced using an editing system that comprises a nucleic acid binding domain that binds to a target site within the sequence having at least 80% identity SEQ ID NO:6 or SEQ ID NO: 7. In some embodiments, the modification/mutation within the sequence having at least 90% sequence identity to SEQ ID NO: 2 may be introduced using an editing system that comprises a sequence-specific DNA binding domain that binds to a target site within the nucleotide sequence of any one of SEQ ID NO:21 or SEQ ID NO:22. In some embodiments, the mutation that is introduced by the editing system may be in at least one gene encoding an GRF transcription factor is a semi-dominant mutation and/or a hypomorphic mutation.

In some embodiments, a plant or part thereof is provided comprising at least one non-natural mutation in an endogenous gene encoding a Growth Regulating Factor (GRF) transcription factor, wherein the at least one non-natural mutation in the endogenous gene encoding a GRF transcription factor results in increased levels of mRNA produced by the endogenous gene. In some embodiments, the at least one non-natural mutation in the endogenous gene encoding a GRF transcription factor results in increased levels of mRNA produced by the endogenous gene and disrupts binding of miR396 to the mRNA produced by the GRF transcription factor gene.

In some embodiments, a plant or part thereof is provided, the plant or plant part thereof comprising a mutated endogenous GRF transcription factor gene that produces a mRNA having reduced miR396 binding and resulting in increased levels of GRF transcription factor mRNA, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:8, wherein the nucleotide sequence of SEQ ID NO:8 comprises a sequence having at least 90% sequence identity (e.g., about 90, 91, 92, 93, 94, 95, 96, 70, 98, 99, or 100%) to the nucleotide sequence of SEQ ID NO: 3, and the target gene is modified (e.g., mutated) within the sequence having at least 90% sequence identity to the nucleotide sequence of SEQ ID NO: 3. In some embodiments, the modification (e.g., mutation) within the sequence having at least 90% sequence identity to SEQ ID NO:3 may be introduced using an editing system that comprises a nucleic acid binding domain that binds to a target site within the sequence having at least 80% identity to SEQ ID NO:8. In some embodiments, the modification within the sequence having at least 90% sequence identity to SEQ ID NO:3 may be introduced using an editing system that comprises a sequence-specific DNA binding domain that binds to a target site within the nucleotide sequence of any one of SEQ ID NO:23.

In some embodiments, the invention provides a plant or part thereof comprising a mutated endogenous GRF transcription factor gene that produces a mRNA having reduced miR396 binding, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs: 121-144, wherein each of SEQ ID NOs: 121-144 comprise a sequence having at least 90% sequence identity (e.g., about 90, 91, 92, 93, 94, 95, 96, 70, 98, 99, or 100%) to any one of SEQ ID NOs: 145-146, and the target gene is modified (e.g., mutated) within the sequence having at least 90% sequence identity to any one of SEQ ID NOs: 145-146. In some embodiments, the modification (e.g., mutation) within the sequence having at least 90% sequence identity to any one of the nucleotide sequence of SEQ ID NOs: 145-146 may be introduced using an editing system that comprises a sequence-specific DNA binding domain that binds to a target site within a nucleotide sequence having at least 80% identity to any one of the nucleotide sequences of SEQ ID NOs: 121-144. In some embodiments, the modification within the sequence having at least 90% sequence identity to any one of the nucleotide sequence of SEQ ID NOs: 145-146 may be introduced using an editing system that comprises a sequence-specific DNA binding domain that binds to a target site within the nucleotide sequence of any one of SEQ ID NOs: 121-144.

In some embodiments, the invention provides a plant or part thereof comprising a mutated endogenous GRF transcription factor gene that produces a mRNA having reduced miR396 binding, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs: 173-198, wherein each of SEQ ID NOs: 173-198 comprise a sequence having at least 90% sequence identity (e.g., about 90, 91, 92, 93, 94, 95, 96, 70, 98, 99, or 100%) to any one of SEQ ID NOs: 199-202, and the target gene is modified (e.g., mutated) within the sequence having at least 90% sequence identity to any one of SEQ ID NOs: 199-202, and the target gene is modified (e.g., mutated) within the sequence having at least 90% sequence identity to any one of SEQ ID NOs: 199-202. In some embodiments, the modification (e.g., mutation) within the sequence having at least 90% sequence identity to any one of the nucleotide sequence of SEQ ID NOs: 199-202 may be introduced using an editing system that comprises a sequence-specific DNA binding domain that binds to a target site within a nucleotide sequence having at least 80% identity to any one of the nucleotide sequences of SEQ ID NOs: 173-198. In some embodiments, the modification within the sequence having at least 90% sequence identity to any one of the nucleotide sequence of SEQ ID NOs: 199-202 may be introduced using an editing system that comprises a sequence-specific DNA binding domain that binds to a target site within the nucleotide sequence of any one of SEQ ID NOs: 174-198.

An additional aspect of the invention provides a plant comprising a Growth Regulating Factor (GRF) transcription factor gene that comprises a mutation in any one of the nucleotide sequences of any one of SEQ ID NOs: 1-33 or 97-202. In some embodiments, the invention provides a plant comprising a mutated Growth Regulating Factor (GRF) transcription factor gene that comprises a nucleotide sequence of any one of SEQ ID NOs: 34-41. In some embodiments, the mutated GRF transcription factor comprises a semi-dominant mutation and/or a hypomorphic mutation.

In some embodiments, the invention provides a corn plant comprising a Growth Regulating Factor (GRF) transcription factor gene that comprises a nucleotide sequence of any one of SEQ ID NOs: 34-41.

In some embodiments, the invention provides a wheat plant comprising a Growth Regulating Factor (GRF) transcription factor gene that produces a mRNA having a mutated miR396 binding site such that the binding of miR396 to the miR396 binding site of the GRF transcription factor mRNA is reduced. In some embodiments, the invention provides a wheat plant having a mutation in the miR396 binding site of a mRNA produced by a Growth Regulating Factor (GRF) transcription factor gene that comprises a nucleotide sequence of any one of SEQ ID NOs: 147-198. In some embodiments, the Growth Regulating Factor (GRF) transcription factor gene that comprises a nucleotide sequence of any one of SEQ ID NOs: 147-198 is in the A genome, the B genome, the D genome, or any combination thereof, of a wheat plant.

In some embodiments, the invention provides a wheat plant comprising a Growth Regulating Factor (GRF) transcription factor gene that produces a mRNA having a mutated miR396 binding site such that the binding of miR396 to the miR396 binding site of the GRF transcription factor mRNA is reduced. In some embodiments, the invention provides a soybean plant having a mutation in the miR396 binding site of a mRNA produced by a Growth Regulating Factor (GRF) transcription factor that comprises a nucleotide sequence of any one of SEQ ID NOs: 97-144. In some embodiments, the Growth Regulating Factor (GRF) transcription factor that comprises a nucleotide sequence of any one of SEQ ID NOs: 97-144 is in the A genome, the B genome, the D genome, or any combination thereof, of a wheat plant.

In some embodiments, the invention provides a corn plant or plant part thereof comprising at least one non-natural mutation in at least one endogenous Growth Regulating Factor (GRF) transcription factor that is located in: (a) a chromosome interval defined by and including base pair (bp) position 211773221 to base pair position 211774543 on chromosome 5 (e.g., Gene ID No. GRMZM5G893117), optionally a chromosome interval defined by and including base pair (bp) position 211773897 to base pair position 211773957; (b) a chromosome interval defined by and including base pair (bp) position 200344009 to base pair position 200348833 on chromosome 5 (e.g., Gene ID No. GRMZM2G034876), optionally a chromosome interval defined by and including base pair (bp) position 200346611 to base pair position 200346671; (c) a chromosome interval defined by and including base pair (bp) position 13817620 to base pair position 13822440 on chromosome 5 (e.g., Gene ID No. GRMZM2G033612), optionally a chromosome interval defined by and including base pair (bp) position 138197933 to base pair position 13819853; (d) a chromosome interval defined by and including base pair (bp) position 177151736 to base pair position 177154443 on chromosome 4 (e.g., Gene ID No. GRMZM2G105335), optionally a chromosome interval defined by and including base pair (bp) position 177152804 to base pair position 177152864; (e) a chromosome interval defined by and including base pair (bp) position 257245490 to base pair position 257249295 on chromosome 1 (e.g., Gene ID No. GRMZM2G018414), optionally a chromosome interval defined by and including base pair (bp) position 257247225 to base pair position 257247285; (f) a chromosome interval defined by and including base pair (bp) position 25722859 to base pair position 25725873 on chromosome 9 (e.g., Gene ID No. GRMZM2G119359), optionally a chromosome interval defined by and including base pair (bp) position 25723770 to base pair position 25723830; (g) a chromosome interval defined by and including base pair (bp) position 60351912 to base pair position 60356302 on chromosome 6 (e.g., Gene ID No. GRMZM2G098594), optionally a chromosome interval defined by and including base pair (bp) position 60354489 to base pair position 60354549; (h) a chromosome interval defined by and including base pair (bp) position 196192921 to base pair position 196194872 on chromosome 5, optionally a chromosome interval defined by and including base pair (bp) position 196194175 to base pair position 196194235; (i) a chromosome interval defined by and including base pair (bp) position 140393394 to base pair position 140398705 on chromosome 10 (e.g., Gene ID No. GRMZM2G129147), optionally a chromosome interval defined by and including base pair (bp) position 140396272 to base pair position 140396332; (j) a chromosome interval defined by and including base pair (bp) position 155831622 to base pair position 155833517 on chromosome 4 (e.g., Gene ID No. GRMZM2G124566), optionally a chromosome interval defined by and including base pair (bp) position 155832749 to base pair position 155832809;

(k) a chromosome interval defined by and including base pair (bp) position 12201898 to base pair position 12208052 on chromosome 2 (e.g., Gene ID No. GRMZM2G041223), optionally a chromosome interval defined by and including base pair (bp) position 12204599 to base pair position 12204659; (l) a chromosome interval defined by and including base pair (bp) position 9818327 to base pair position 9820186 on chromosome 9 (e.g., Gene ID No. GRMZM2G067743), optionally a chromosome interval defined by and including base pair (bp) position 9819224 to base pair position 9819284; (m) a chromosome interval defined by and including base pair (bp) position 108477686 to base pair position 108480099 on chromosome 6 (e.g., Gene ID No. GRMZM5G850129), optionally a chromosome interval defined by and including base pair (bp) position 108478747 to base pair position 108478807; (n) a chromosome interval defined by and including base pair (bp) position 225827712 to base pair position 225832487 on chromosome 2 (e.g., Gene ID No. GRMZM2G099862), optionally a chromosome interval defined by and including base pair (bp) position 225830099 to base pair position 225830159; (o) a chromosome interval defined by and including base pair (bp) position 272414778 to base pair position 272420567 on chromosome 1 (e.g., Gene ID No. GRMZM2G178261); (p) a chromosome interval defined by and including base pair (bp) position 199377455 to base pair position 199381799 on chromosome 2; (q) a chromosome interval defined by and including base pair (bp) position 145016279 to base pair position 145019899 on chromosome 7; and/or (r) a chromosome interval defined by and including base pair (bp) position 8708791 to base pair position 8711617 on chromosome 5 (e.g., Gene ID No. GRMZM5G853392), wherein the mutation results in increased GRF transcription factor mRNA, and optionally, disrupts the binding of miR396 to the GRF transcription factor, and the chromosomal intervals of (a) to (r) correspond to the reference maize genome of B73.

In some embodiments, a corn plant may comprise a mutation on chromosome 5 (a) bp position 211773927, (b) bp position 200346641, (c) bp position 13819823, and (d) bp position 196194205, wherein the chromosomal position of (a) to (e) correspond to the reference maize genome of B73.

In some embodiments, a corn plant may comprise a mutation on chromosome 4 (a) bp position 177152834, and/or (b) bp position 155832779, wherein the chromosomal position of (a) and (b) correspond to the reference maize genome of B73.

In some embodiments, a corn plant may comprise a mutation on chromosome 1, bp position 257247255, wherein the chromosomal position of 257247255 corresponds to the reference maize genome of B73.

In some embodiments, a corn plant may comprise a mutation on chromosome 9 (a) bp position 25723800 and/or (b) bp position 9819254, wherein the chromosomal position of (a) and (b) correspond to the reference maize genome of B73.

In some embodiments, a corn plant may comprise a mutation on chromosome 6 (a) bp position 60354519 and/or (b) bp position 108478777, wherein the chromosomal position of (a) and (b) correspond to the reference maize genome of B73.

In some embodiments, a corn plant may comprise a mutation on chromosome 10, bp position 140396302, wherein the chromosomal position of 140396302 corresponds to the reference maize genome of B73.

In some embodiments, a corn plant may comprise a mutation on chromosome 2 (a) bp position 12204629, and/or (b) bp position 225830129, wherein the chromosomal position of (a) and (b) correspond to the reference maize genome of B73.

With regard to corn (*Zea mays*), markers of the present invention are described herein with respect to the positions of marker loci in the B73 corn genome "B73 RefGen_v3" (assembly aka B73 RefGen_v3, AGPv3) at the MaizeGDB internet resource (maizegdb.org/assembly).

The present invention provides methods and compositions for modifying GRF transcription factors involved in plant growth and development, in particular those GRF transcription factors that regulate biomass, yield, inflorescence size/weight, fruit yield, fruit quality, fruit size, seed size, seed number, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, length of roots, number of roots, size and/or weight of root mass, or any combination of these characteristics. Thus, in some embodiments of the invention, a plant comprising a mutated endogenous GRF transcription factor gene having reduced miR396 binding, may exhibit at least one of the following phenotypes of increased meristem size, increased seed size, increased biomass, increased leaf size, increased root size, increased nitrogen use efficiency, increased disease resistance, increased height and/or increased internode length as compared to a control plant that does not comprise the mutated endogenous GRF transcription factor gene having reduced miR396 binding.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 4-18, 121-144, or 173-198, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having at least 65% sequence identity (e.g., about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 70, 98, 99, or 100%) to the nucleotide sequence of SEQ ID NO: 9 or SEQ ID NO:14 and comprising a miR396 binding site sequence at bp position 21 to 42 of SEQ ID NO:9 (GRF8 60 nt cDNA or SEQ ID NO:14 (GRF5 60 nt cDNA), the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 4, 5, or 9-18 and comprising a miR396 binding site sequence at bp position 21 to 42 of any one of SEQ ID NOs: 4, 5, or 9-18, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:6 or SEQ ID NO:7, and comprising a miR396 binding site sequence at bp position 21 to 42 of SEQ ID NO:6 or SEQ ID NO: 7, the binding site sequence having at least 90% sequence identity (e.g., about 90, 91, 92, 93, 94, 95, 96, 70, 98, 99, or 100%) to SEQ ID NO:2, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO: 8, and comprising a miR396 binding site sequence at bp position 21 to 42 of SEQ ID NO:8, the binding site sequence having at least 90% sequence identity (e.g., about 90, 91, 92, 93, 94, 95, 96, 70, 98, 99, or 100%) to SEQ ID NO:3, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:4, and comprising a miR396 binding site sequence at bp position 21 to 42 of SEQ ID NO:4, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:5, and comprising a miR396 binding site sequence at bp position 21 to 42 of SEQ ID NO:5, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:9, and comprising a miR396 binding site sequence at bp position 21 to 42 of SEQ ID NO:9, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:10, and comprising a miR396 binding site sequence at bp position 21 to 42 of SEQ ID NO:10, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:11, and comprising a miR396 binding site sequence at bp position 21 to 42 of SEQ ID NO:11, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:12, and comprising a miR396 binding site sequence at bp position 21 to 42 of SEQ ID NO:12, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:13, and comprising a miR396 binding site sequence at bp position 21 to 42 of SEQ ID NO:13, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:14, and comprising a miR396 binding site sequence at bp position 21 to 42 of SEQ ID NO:14, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:15, and comprising a miR396 binding site sequence at bp position 21 to 42 of SEQ ID NO:15, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:16, and comprising a miR396 binding site sequence at bp position 21 to 42 of SEQ ID NO:16, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:17, and comprising a miR396 binding site sequence at bp position 21 to 42 of SEQ ID NO:17, the binding site sequence having at least 90% sequence identity (e.g., about 90, 91, 92, 93, 94, 95, 96, 70, 98, 99, or 100%) to SEQ ID NO: 1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:18, and comprising a miR396 binding site sequence at bp position 21 to 42 of SEQ ID NO:18, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 121-144 and comprising a miR396 binding site sequence at bp position 21 to 42 of any one of SEQ ID NOs: 121-144, the binding site sequence having at least 90% sequence identity (e.g., about 90, 91, 92, 93, 94, 95, 96, 70, 98, 99, or 100%) to SEQ ID NO:145 or SEQ ID NO:146, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 173-198 and comprising a miR396 binding site sequence at bp position 21 to 42 of any one of SEQ ID NOs: 173-198, the binding site sequence having at least 90% sequence identity (e.g., about 90, 91, 92, 93, 94, 95, 96, 70, 98, 99, or 100%) to SEQ ID NO:145 or SEQ ID NO:146, thereby generating an edit in the endogenous GRF transcription factor gene of the plant cell.

In some embodiments, the method may further comprise regenerating a plant from the plant cell comprising an edit in the endogenous GRF transcription factor gene to produce a plant comprising the edit in its endogenous GRF transcription factor gene. In some embodiments, the plant comprising the edit in its endogenous GRF transcription factor gene may have increased growth compared to a control plant that does not comprise the edit. In some embodiments, the edit results in a non-natural mutation.

In some embodiments, a method for making a plant is provided, the method comprising: (a) contacting a population of plant cells comprising an endogenous gene encoding a GRF transcription factor with an editing system comprising a nucleic acid binding domain that binds to a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NOs: 1-3, 145, 146, or 199-202 or SEQ ID NOs: 4-18, 121-144, or 173-198; (b) selecting a plant cell from said population comprising a mutation in at least one endogenous gene encoding a GRF transcription factor, wherein the mutation is a substitution of at least one nucleotide in the at least one endogenous gene, wherein the mutation reduces or eliminates the ability of miR396 to bind to a mRNA produced by the at least one endogenous gene encoding a GRF transcription factor comprising the mutation; and (c) growing the selected plant cell into a plant.

In some embodiments, the present invention provides a method for producing a plant or part thereof comprising at least one cell in which an endogenous GRF transcription factor gene is mutated, the method comprising contacting a target site in the GRF transcription factor gene in the plant or plant part with an editing system comprising a nucleic acid binding domain that binds to a target site in (or within) the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising at least one cell having a mutation in the endogenous GRF transcription factor gene. In some embodiments, a mutated endogenous GRF transcription factor gene produces a mRNA that has reduced binding of its corresponding miR396 (e.g., the miR396 that naturally binds to the wild type GRF transcription factor mRNA).

In some embodiments, the present invention provides a method of producing a plant or part thereof that comprises a mutated endogenous GRF transcription factor gene that produces an mRNA having reduced miR396 binding, the method comprising contacting a target site in an endogenous GRF contacting a target site in an endogenous GRF transcription factor gene with an editing system comprising a nucleic acid binding domain that binds to a target site in the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising a mutated endogenous GRF transcription factor gene producing a mRNA having reduced miR396 binding. In some embodiments, the nucleotide sequence of any one of SEQ ID NOs: 4-18, 121-144, or 173-198, or SEQ ID NOs: 19-33, 97-120, or 147-172 comprises a sequence having at least 90% sequence identity (e.g., about 90, 91, 92, 93, 94, 95, 96, 70, 98, 99, or 100%) to the nucleotide sequence of any one of SEQ ID NOs: 1-3, 145, 146, or 199-202, the sequence having at least 90% sequence identity to the nucleotide sequence of any one of SEQ ID NOs: 1-3, 145, 146, or 199-202 is modified.

In some embodiments, a plant comprising a mutated endogenous GRF transcription factor gene that produces a mRNA having reduced miR396 binding exhibits increased growth as compared to a control plant (e.g., a plant that does not comprise said modification or mutation in its endogenous GRF transcription factor gene or in which the plant's endogenous GRF transcription factor gene has not been contacted with the editing system). In some embodiments, a plant comprising a mutated endogenous GRF transcription factor gene that produces a mRNA having reduced miR396 binding exhibits at least one of the following phenotypes of increased meristem size, increased seed size, increased biomass, increased leaf size, increased root size, increased nitrogen use efficiency, increased disease resistance, increased height and/or increased internode length as compared to a control plant (e.g., a plant that does not comprise said modification or mutation in its endogenous GRF transcription factor gene or in which the plant's endogenous GRF transcription factor gene has not been contacted with the editing system).

In some embodiments, the present invention provides a method of producing a plant or part thereof having increased growth or an increased growth rate, the method comprising contacting a target site in an endogenous GRF transcription factor gene with an editing system comprising a nucleic acid binding domain that binds to a target site in the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising a mutated endogenous GRF transcription factor gene that produces a mRNA having reduced miR396 binding, thereby producing a plant or part thereof having increased growth or an increased growth rate. In some embodiments, the nucleotide sequence of any one of SEQ ID NOs: 4-18, 121-144, or 173-198 or SEQ ID NOs: 19-33, 97-120, or 147-172 comprises a sequence having at least 90% sequence identity (e.g., about 90, 91, 92, 93, 94, 95, 96, 70, 98, 99, or 100%) to the nucleotide sequence of any one of SEQ ID NOs: 1-3, 145, 146, or 199-202, the sequence having at least 90% sequence identity to the nucleotide sequence of any one of SEQ ID NOs: 1-3, 145, 146, or 199-202 is modified.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a GRF transcription factor may comprise contacting a target nucleic acid (e.g., a nucleic acid encoding a GRF transcription factor) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid (see, e.g., FIG. 2). In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a GRF transcription factor may comprise contacting a target nucleic acid (e.g., a nucleic acid encoding a GRF transcription factor) with a sequence-specific DNA binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific DNA binding fusion protein to the target nucleic acid and the sequence-specific DNA binding fusion protein is capable of recruiting the deaminase fusion protein to the target nucleic acid via the peptide tag-affinity polypeptide interaction, thereby editing a locus within the target nucleic acid. In some embodiments, the sequence-specific DNA binding fusion protein may be fused to the affinity polypeptide that binds the peptide tag and the deaminase may be fuse to the peptide tag, thereby recruiting the deaminase to the sequence-specific DNA binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific DNA binding fusion proteins, deaminase fusion proteins and guides may be provided as ribonucleoproteins (RNPs).

In some embodiments, methods such as prime editing may be used to generate a mutation in an endogenous GRF transcription factor gene. In prime editing, RNA-dependent DNA polymerase (reverse transcriptase, RT) and reverse transcriptase templates (RT template) are used in combination with sequence specific DNA binding domains that confer the ability to recognize and bind the target in a sequence-specific manner, and which can also cause a nick of the PAM-containing strand within the target. The DNA binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

In some embodiments, the mutation or modification may be an insertion, a deletion and/or a point mutation. In some embodiments, a plant part may be a cell. In some embodiments, the plant or plant part thereof may be any plant or part thereof as described herein. In some embodiments, a plant useful with this invention may be corn, soy, canola, wheat, rice, cotton, sugarcane, sugar beet, barley, oats, alfalfa, sunflower, safflower, oil palm. sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp. In some embodiments, a plant comprising a mutated endogenous GRF transcription factor gene that produces a mRNA having reduced miR396 binding may comprise increased growth and/or an increased growth rate, optionally an increased growth and/or increased growth rate of its roots and/or fruit.

In some embodiments, the plant may be corn and the fruit may be an ear, optionally wherein the corn plant comprises a short stature/semi-dwarf phenotype.

In some embodiments, a mutation that is introduced into an endogenous GRF transcription factor gene and resulting in the production of a mRNA having reduced miR396 binding may be a non-naturally occurring mutation. In some embodiments, a mutation that is introduced into an endogenous GRF transcription factor gene and resulting in the production of a mRNA having reduced miR396 binding may be a substitution, an insertion and/or a deletion. In some embodiments, a mutation that is introduced into an endogenous GRF transcription factor gene and resulting in the production of a mRNA having reduced miR396 binding may be a point mutation.

In some embodiments, a GRF transcription factor may include, but is not limited to, a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, a GRF transcription factor may include, but is not limited to, a GRF6, GRF2, GRF1, GRF14, GRF15, GRF8, GRF4, GRF12, GRF10, GRF11, GRF5, GRF3, GRF9, GRF13, or a GRF7.

In some embodiments, the present invention further provides a method of producing/breeding a transgene-free base-edited plant, the method comprising: (a) crossing a plant of this invention comprising at least one mutation/modification in at least one endogenous GRF transcription factor gene that results in a mRNA having reduced binding of the corresponding miR396 with a transgene free plant, thereby introducing the at least one mutation/modification into the plant that is transgene-free; and (b) selecting a progeny plant that comprises the at least one single nucleotide substitution but is transgene-free, thereby producing a transgene free base-edited plant.

In some embodiments, a plant comprising a mutated endogenous GRF transcription factor gene that produces a mRNA having reduced miR396 binding may exhibit increased growth as compared to a control plant (e.g., a plant that does not comprise said modification or mutation in its endogenous GRF transcription factor gene or in which the plant's endogenous GRF transcription factor gene has not been contacted with the nuclease). In some embodiments, a plant comprising a mutated endogenous GRF transcription factor gene that produces a mRNA having reduced miR396 binding may exhibit at least one of the following phenotypes of increased meristem size, increased seed size, increased biomass, increased leaf size, increased root size, increased nitrogen use efficiency, increased disease resistance, increased height and/or increased internode length as compared to a control plant (e.g., a plant that does not comprise said modification or mutation in its endogenous GRF transcription factor gene or in which the plant's endogenous GRF transcription factor gene has not been contacted with the nuclease).

The present invention further provides a guide nucleic acid (e.g., gRNA) that binds to a target site in a GRF transcription factor gene, the target site comprising any one of the nucleotide sequences of SEQ ID NOs: 4-18, 121-144, or 173-198, optionally wherein the GRF transcription factor may be a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, a guide nucleic acid (e.g., gRNA) that binds to a target site in a GRF transcription factor gene is provide, the target site comprising any one of the nucleotide sequences of SEQ ID NOs: 4-18, 121-144, or 173-198, optionally wherein the GRF transcription factor may be a GRF6, GRF2, GRF1, GRF14, GRF15, GRF8, GRF4, GRF12, GRF10, GRF11, GRF5, GRF3, GRF9, GRF13, or a GRF7.

In some embodiments, a guide nucleic acid of a gene editing system of this invention may comprise a spacer that is complementary to a fragment or portion of the nucleotide sequence of any one of SEQ ID NOs: 4-18, 121-144, or 173-198, wherein the fragment or portion of any one of SEQ ID NOs: 4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs: 4-18, 121-144, or 173-198. In some embodiments, a guide nucleic acid may comprise a spacer having complementary to consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs: 4-18, 121-144, or 173-198 (counted from the 5' end). In some embodiments, a guide nucleic acid may comprise a spacer that is complementary to consecutive nucleotides from base pair position 20 to base pair position 42 of any one of the nucleotide sequences of SEQ ID NOs: 4-18, 121-144, or 173-198 (counted from the 5' end). In some embodiments, the guide nucleic acid may comprise a spacer having the nucleotide sequence of any one of SEQ ID NOs: 48-71.

The present invention further provides an editing system comprising a guide nucleic acid of the invention and a CRISPR-Cas effector protein that associates with the guide nucleic acid. In some embodiments, an editing system of the invention may further comprise tracr nucleic acid that associates with the guide nucleic acid and a CRISPR-Cas effector protein, optionally wherein the tracr nucleic acid and the guide nucleic acid are covalently linked.

The present invention further provides an editing system comprising a CRISPR-Cas effector protein in association with a guide nucleic acid, wherein the guide nucleic acid comprises a spacer sequence that binds to a GRF transcription factor gene. In some embodiments, the GRF transcription factor gene may be a GRF1 gene, GRF2 gene, GRF3 gene, GRF4 gene, GRF5 gene, GRF6 gene, GRF7 gene, GRF8 gene, GRF9 gene, GRF10 gene, GRF11 gene, GRF12 gene, GRF13 gene, GRF14 gene, GRF15 gene, GRF16 gene, GRF17 gene, GRF18 gene, GRF19 gene, or a GRF20 gene. In some embodiments, the GRF transcription factor gene may be a GRF6 gene, GRF2 gene, GRF1 gene, GRF14 gene, GRF15 gene, GRF8 gene, GRF4 gene, GRF12 gene, GRF10 gene, GRF11 gene, GRF5 gene, GRF3 gene, GRF9 gene, GRF13 gene, or a GRF7 gene. In some embodiments, the GRF transcription factor gene of the gene editing system may comprise the nucleotide sequence of any one of SEQ ID NOs: 1-3, 145, 146, or 199-202.

In some embodiments, a guide nucleic acid of the gene editing system may comprise a spacer sequence having the nucleotide sequence of any one of SEQ ID NOs: 48-71.

The present invention further provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one SEQ ID NOs: 4-18, 121-144, or 173-198, wherein the nuclease cleaves the target strand.

Further provided herein are expression cassettes comprising a (a) polynucleotide encoding CRISPR-Cas effector protein comprising a cleavage domain and (b) a guide nucleic acid that binds to a target site in a GRF transcription factor gene, wherein the guide nucleic acid comprises a spacer sequence that is complementary to and binds to a sequence having at least 80% sequence identity to at least a portion of any one of the nucleotide sequences of SEQ ID NOs: 1-3, 145, 146, or 199-202 or a sequence having at least 80% sequence identity to at least a portion of any one of the nucleotide sequences of SEQ ID NOs: 4-18, 121-144, or 173-198, as described herein. In some embodiments, the at least a portion may comprise at least one nucleotide or at least two (e.g., 2, 3, 4, 5, 6, 7, 8, 9, 10, 11, 12, 13, 14, 15, 16, 17, 18, 19, 20, 21, or 22) consecutive nucleotides of any one of the nucleotide sequences of SEQ ID NOs: 1-3, 145, 146, or 199-202.

In some embodiments, the at least a portion may be a portion of the nucleotide sequence of any one of SEQ ID NOs: 1-3, 145, 146, or 199-202 and/or any one of SEQ ID NOs: 4-18, 121-144, or 173-198, wherein the portion of any one of SEQ ID NOs: 1-3, 145, 146, or 199-202 and/or any one of SEQ ID NOs: 4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of any one of SEQ ID NOs: 1-3, 145, 146, or 199-202 and/or any one of SEQ ID NOs: 4-18, 121-144, or 173-198. In some embodiments, the at least a portion may comprise consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of any one of SEQ ID NOs: 1-3, 145, 146, or 199-202 and/or any one of SEQ ID NOs: 4-18, 121-144, or 173-198 (counted from the 5' end). In some embodiments, the at least a portion may comprise consecutive nucleotides from base pair position 20 to base pair position 42 of any one of the nucleotide sequences of any one of SEQ ID NOs: 1-3, 145, 146, or 199-202 and/or any one of SEQ ID NOs: 4-18, 121-144, or 173-198 (counted from the 5' end). In some embodiments, a portion of any one of SEQ ID NOs: 1-3, 145, 146, or 199-202 and/or any one of SEQ ID NOs: 4-18, 121-144, or 173-198 may be at least about 1, 2, 3, 4, 5, 6, 7, 8, 9, 10, 11, 12, 13, 14, 15, 16, 17, 18, 19, 20, 21, 22, 23, 24, or 25 or more consecutive nucleotides of any one of SEQ ID NOs: 1-3, 145, 146, or 199-202 and/or any one of SEQ ID NOs: 4-18, 121-144, or 173-198.

Also provided herein is a nucleic acid encoding GRF transcription factor that produces a mRNA having a mutated miR396 binding site, wherein the mutated miR396 binding site comprises a mutation that results in increased levels of the mRNA, and optionally, disrupts (reduced or eliminates) miR396 binding to the mRNA. In some embodiments, the mutation may eliminate the binding of the corresponding miR396 (e.g., zero detectable binding). In some embodiments, the mutation may reduce the ability of the corresponding miR396 to bind to the GRF transcription factor mRNA by at least about 75% (e.g., about 75, 76, 77, 78, 79, 80, 81, 82, 83, 84, 85, 86, 87, 88, 89, 90, 91, 92, 93, 94, 95, 96, 97, 98, 99% or more, or any range or value therein, of a reduction in miR396 binding, or any range or value therein). In some embodiments, the GRF transcription factor may be a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, the GRF transcription factor may be a GRF6, GRF2, GRF1, GRF14, GRF15, GRF8, GRF4, GRF12, GRF10, GRF11, GRF5, GRF3, GRF9, GRF13, or a GRF7. In some embodiments, a plant or part thereof is provided that comprises a nucleic acid of the invention encoding a GRF transcription factor that produces a mRNA having a mutated miR396 binding site, wherein the mutated miR396 binding site comprises a mutation that results in increased levels of the mRNA, and optionally, disrupts miR396 binding. In some embodiments the plant is a corn plant, optionally wherein the corn plant comprises a short stature/semi-dwarf phenotype. In some embodiments, the plant is a wheat plant or part thereof, optionally wherein the nucleic acid encoding a GRF transcription factor that produces a mRNA having a mutated miR396 binding site may be comprised in the A genome, the B genome, the D genome or in any combination thereof. In some embodiments, the plant or part thereof that comprises a nucleic acid of the invention encoding a GRF transcription factor that produces a mRNA having a mutated miR396 binding site may comprise increased growth or an increased rate of growth. In some embodiments, the plant or part thereof that comprises a nucleic acid of the invention encoding a GRF transcription factor that produces a mRNA having a mutated miR396 binding site may exhibit at least one of the following phenotypes of increased meristem size, increased seed size, increased biomass, increased leaf size, increased root size, increased nitrogen use efficiency, increased disease resistance, increased height and/or increased internode length.

In some embodiments, the present invention further provides a guide nucleic acid that binds to a target nucleic acid in a GRF transcription factor in a corn plant, wherein the target nucleic acid is located in: (a) a chromosome interval defined by and including base pair (bp) position 211773221 to base pair position 211774543 on chromosome 5, optionally a chromosome interval defined by and including base pair (bp) position 211773897 to base pair position 211773957; (b) a chromosome interval defined by and including base pair (bp) position 200344009 to base pair position 200348833 on chromosome 5, optionally a chromosome interval defined by and including base pair (bp) position 200346611 to base pair position 200346671; (c) a chromosome interval defined by and including base pair (bp) position 13817620 to base pair position 13822440 on chromosome 5, optionally a chromosome interval defined by and including base pair (bp) position 138197933 to base pair position 13819853; (d) a chromosome interval defined by and including base pair (bp) position 177151736 to base pair position 177154443 on chromosome 4, optionally a chromosome interval defined by and including base pair (bp) position 177152804 to base pair position 177152864; (e) a chromosome interval defined by and including base pair (bp) position 257245490 to base pair position 257249295 on chromosome 1, optionally a chromosome interval defined by and including base pair (bp) position 257247225 to base pair position 257247285; (f) a chromosome interval defined by and including base pair (bp) position 25722859 to base pair position 25725873 on chromosome 9, optionally a chromosome interval defined by and including base pair (bp) position 25723770 to base pair position 25723830; (g) a chromosome interval defined by and including base pair (bp) position 60351912 to base pair position 60356302 on chromosome 6, optionally a chromosome interval defined by and including base pair (bp) position 60354489 to base pair position 60354549; (h) a chromosome interval defined by and including base pair (bp) position 196192921 to base pair position 196194872 on chromosome 5, optionally a chromosome interval defined by and including base pair (bp) position 196194175 to base pair position 196194235; (i) a chromosome interval defined by and including base pair (bp) position 140393394 to base pair position 140398705 on chromosome 10, optionally a chromosome interval defined by and including base pair (bp) position 140396272 to base pair position 140396332; (j) a chromosome interval defined by and including base pair (bp) position 155831622 to base pair position 155833517 on chromosome 4, optionally a chromosome interval defined by and including base pair (bp) position 155832749 to base pair position 155832809; (k) a chromosome interval defined by and including base pair (bp) position 12201898 to base pair position 12208052 on chromosome 2, optionally a chromosome interval defined by and including base pair (bp) position 12204599 to base pair position 12204659; (l) a chromosome interval defined by and including base pair (bp) position 9818327 to base pair position 9820186 on chromosome 9, optionally a chromosome interval defined by and including base pair (bp) position 9819224 to base pair position 9819284; (m) a chromosome interval defined by and including base pair (bp) position 108477686 to base pair position 108480099 on chromosome 6, optionally a chromosome interval defined by and including base pair (bp) position 108478747 to base pair position 108478807; (n) a chromosome interval defined by and including base pair (bp) position 225827712 to base pair position 225832487 on chromosome 2, optionally a chromosome interval defined by and including base pair (bp) position 225830099 to base pair position 225830159; (o) a chromosome interval defined by and including base pair (bp) position 272414778 to base pair position 272420567 on chromosome 1; (p) a chromosome interval defined by and including base pair (bp) position 199377455 to base pair position 199381799 on chromosome 2; (q) a chromosome interval defined by and including base pair (bp) position 145016279 to base pair position 145019899 on chromosome 7; and/or (r) a chromosome interval defined by and including base pair (bp) position 8708791 to base pair position 8711617 on chromosome 5, wherein the mutation results in increased levels of the mRNA, and optionally, disrupts the binding of miR396 to the GRF transcription factor, wherein the chromosomal intervals of (a) to (r) correspond to the reference corn genome of B73 (see e.g., Table 1).

In some embodiments, a sequence-specific nucleic acid binding domain (DNA binding domains) of an editing system useful with this invention can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein.

In some embodiments, a sequence-specific DNA binding domain may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csnl and Csx12), Cas10, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

Figure 4A:
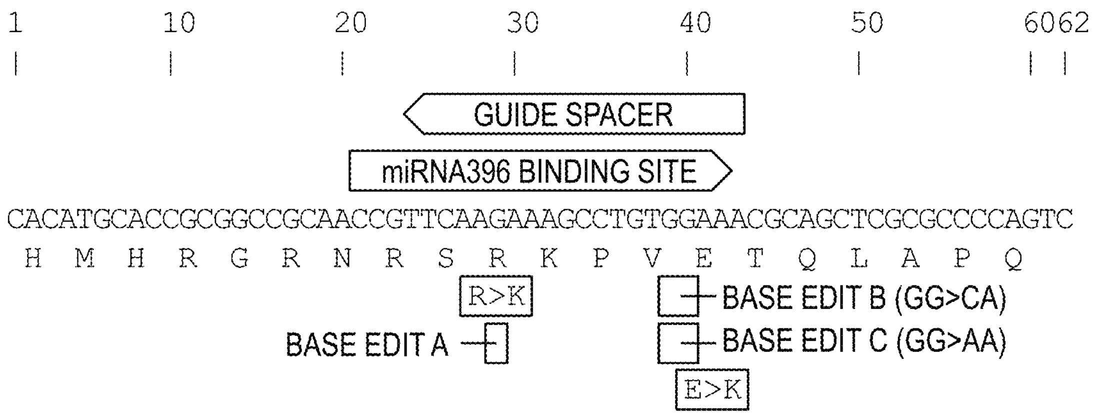
FIGS. 4A-4B show example Cas9 base edits.
Figure 4B:
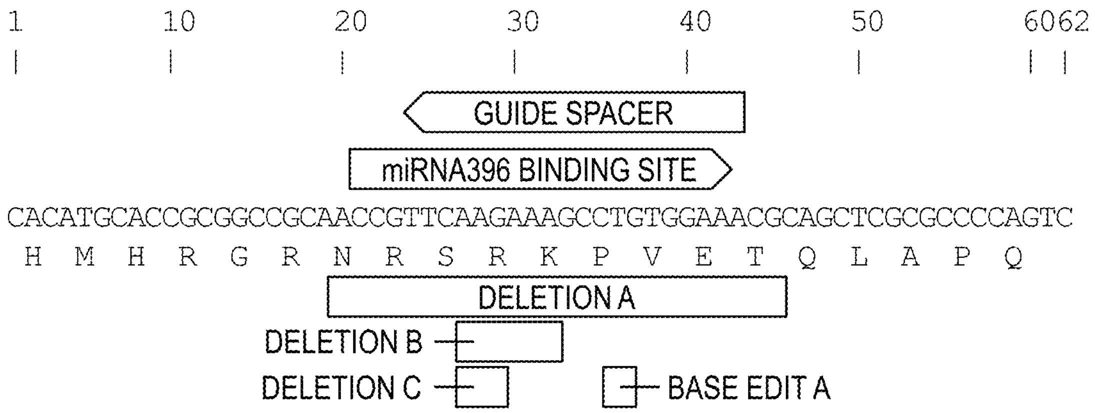

A CRISPR Cas9 effector protein or CRISPR Cas9 effector domain useful with this invention may be any known or later identified Cas9 nuclease (see, e.g., SEQ ID NOs: 234-250). In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., Weissella spp., and/or Olsenella spp. FIGS. 4A-4B show example base edits using Cas9.

In some embodiments, the CRISPR-Cas effector protein may be a Cas9 polypeptide derived from *Streptococcus pyogenes* and recognizes the PAM sequence motif NGG, NAG, NGA (Mali et al, *Science* 2013; 339 (6121): 823-826). In some embodiments, the CRISPR-Cas effector protein may be a Cas9 polypeptide derived from *Streptococcus* thermophiles and recognizes the PAM sequence motif NGGNG and/or NNAGAAW (W=A or T) (See, e.g., Horvath et al, *Science,* 2010; 327 (5962): 167-170, and Deveau et al, *J Bacteriol* 2008; 190 (4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190 (4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, *PNAS* 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease (see, e.g., SEQ ID NOs: 214-230, SEQ ID NOs: 231-233). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

Figure 5A:
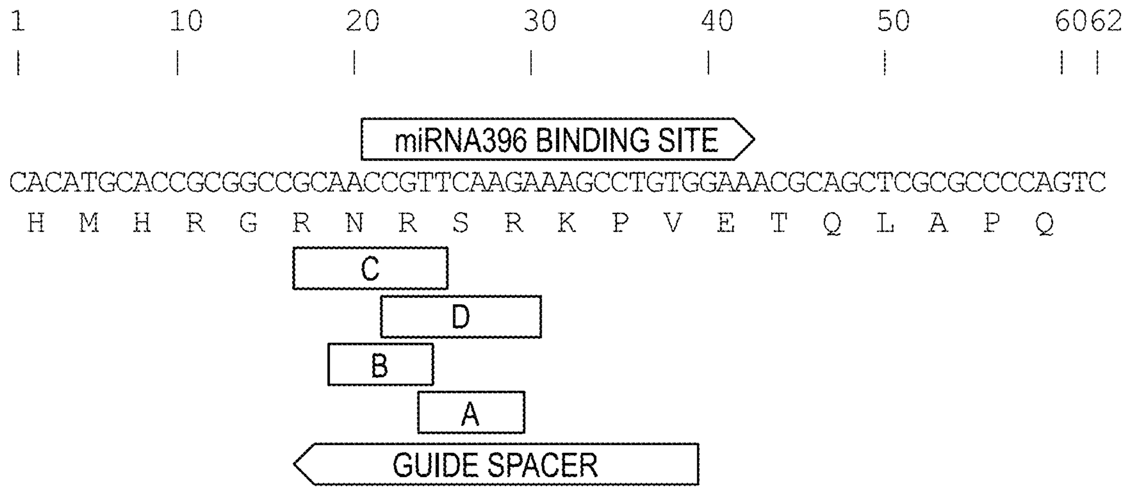
FIG. 5A-5B show example Cas12a (Cpf1) base edits (FIG. 5A top sequence: SEQ ID NO: 4, bottom sequence: SEQ ID NO:260.
Figure 5B:
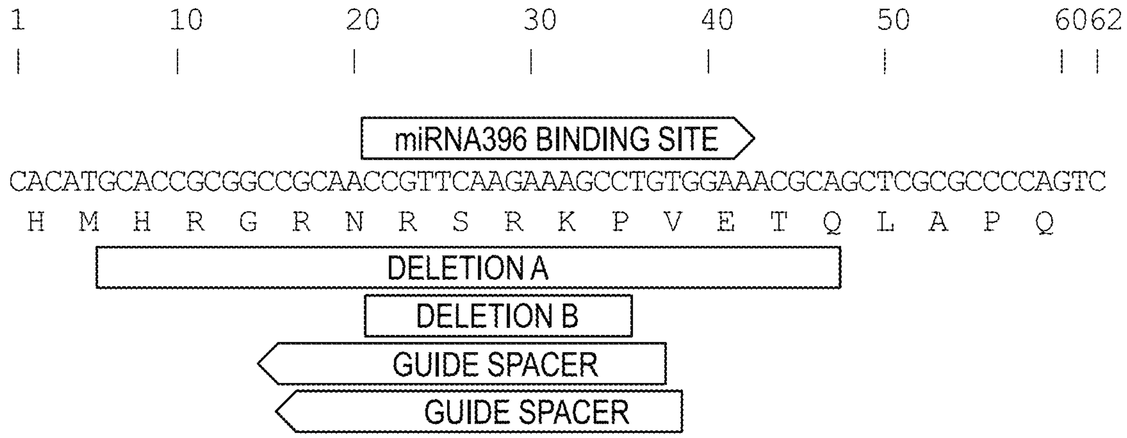

A CRISPR Cas12a effector protein/domain useful with this invention may be any known or later identified Cas12a polypeptide (previously known as Cpf1) (see, e.g., U.S. U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity. FIG. 5A-5B show example base edits using Cas12a (Cpf1).

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:206, SEQ ID NO:207 or SEQ ID NO:208). In some embodiments, the cytosine deaminase may be an APOBEC1 deaminase having the amino acid sequence of SEQ ID NO:77. In some embodiments, the cytosine deaminase may be an APOBEC3A deaminase having the amino acid sequence of SEQ ID NO:78. In some embodiments, the cytosine deaminase may be an CDA1 deaminase, optionally a CDA1 having the amino acid sequence of SEQ ID NO:79. In some embodiments, the cytosine deaminase may be a FERNY deaminase, optionally a FERNY having the amino acid sequence of SEQ ID NO:80. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:77, SEQ ID NO:78, SEQ ID NO:79 or SEQ ID NO:80

(e.g., at least 80%, at least 85%, at least 90%, at least 92%, at least 95%, at least 96%, at least 97%, at least 98%, at least 99%, or at least 99.5% identical to the amino acid sequence of SEQ ID NO: 77, SEQ ID NO: 78, SEQ ID NO: 79 or SEQ ID NO: 80, SEQ ID NO:206, SEQ ID NO: 207 or SEQ ID NO:208). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:81 or a polypeptide having about 70% to about 99.5% identity to the amino acid sequence of SEQ ID NO:81 (e.g., at least 80%, at least 85%, at least 90%, at least 92%, at least 95%, at least 96%, at least 97%, at least 98%, at least 99%, or at least 99.5% identical to the amino acid sequence of SEQ ID NO:81). For example, in some embodiments, a UGI domain may comprise a fragment of the amino acid sequence of SEQ ID NO:81 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:81. In some embodiments, a UGI domain may be a variant of a known UGI (e.g., SEQ ID NO:81) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO: 72. In some embodiments, a mutated/evolved *E. coli* TadA* comprises the amino acid sequence of SEQ ID NOs: 73-76 or 209-213 (e.g., SEQ ID NOs: 73, 74, 75, 76, 209, 210, 211, 212 or 213). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csnl and Csx12), Cas10, Csy1, Csy2, Csy3, Csel, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csxl7, Csxl4, Csx10, Csx16, CsaX, Csx3, Csx1, Csx15, Csfl, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csx17, Csx14, Csx10, Csx16, CsaX, Csx3, Csxl, Csx15, Csfl, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer) (e.g., consecutive nucleotides of any one of SEQ ID NOs: 1-18) (e.g., SEQ ID NOs: 48-71). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
    5'-NNNNNNNNNNNNNNNNNNNN-3' RNA Spacer (SEQ ID NO: 203)
       ||||||||||||||||||||
3'AAANNNNNNNNNNNNNNNNNNNNN-5' Target strand (SEQ ID NO: 204)
  ||||
5'TTTNNNNNNNNNNNNNNNNNNNNN-3' Non-target strand (SEQ ID NO: 205)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific DNA binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26 (5): 910-924 (2017)); Gilbreth (*Curr Opin Struc Biol* 22 (4): 413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihydrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

In some embodiments, the invention provides cells comprising one or more polynucleotides, guide nucleic acids, nucleic acid constructs, expression cassettes or vectors of the invention.

In some embodiments, a method of editing an endogenous GRF transcription factor gene in a plant or plant part is provided, the method comprising contacting a target site in the GRF transcription factor gene in the plant or plant part with a cytosine base editing system comprising a cytosine deaminase and a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, wherein the cytosine deaminase generates at least one C to T conversion in the nucleotide sequence of any one of SEQ ID NOs: 1-3, 145, 146, or 199-202, thereby producing a plant or part thereof comprising at least one cell having a mutation in the endogenous GRF transcription factor gene.

In some embodiments, a method of editing an endogenous GRF transcription factor gene in a plant or plant part is provided, the method comprising contacting a target site in the GRF transcription factor gene in the plant or plant part with an adenine base editing system comprising an adenine deaminase and a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, wherein the cytosine deaminase generates at least one A to G conversion in the nucleotide sequence of any one of SEQ ID NOs: 1-3, 145, 146, or 199-202, thereby producing a plant or part thereof comprising at least one cell having a mutation in the endogenous GRF transcription factor gene.

In some embodiments, a method of detecting a mutant GRF (a mutation in an endogenous GRF transcription factor gene) is provide, the method comprising detecting in the genome of a plant a base substitution in at least one of positions 11, 19, 21 and/or 22 of the nucleotide sequence of any one of SEQ ID NOs: 1-3, 145, 146, or 199-202. In some embodiments, the substitution that is detected at position 11 of the nucleotide sequence of any one of SEQ ID NOs: 1-3, 145, 146, or 199-202 may be from G>A. In some embodiments, the substitution that is detected at position 19 of the nucleotide sequence of any one of SEQ ID NOs: 1-3, 145, 146, or 199-202 may be from G>A or G>C. In some embodiments, the substitution that is detected at position that is detected at position 21 of the nucleotide sequence of any one of SEQ ID NOs: 1-3, 145, 146, or 199-202 may be from G>A or G>C. In some embodiments, the substitution that is detected at position 22 of the nucleotide sequence of any one of SEQ ID NOs: 1-3, 145, 146, or 199-202 may be from G>A or G>C.

In some embodiments, the present invention provides a method of detecting a mutation in an endogenous GRF gene, comprising detecting in the genome of a plant one or more of any one of the nucleotide sequences of SEQ ID NOs: 34-41.

In some embodiments, the present invention provides a method of producing a plant comprising a mutation in an endogenous GRF transcription factor gene and at least one polynucleotide of interest, the method comprising crossing a plant of the invention comprising at least one mutation in an endogenous GRF transcription factor gene (a first plant) with a second plant that comprises the at least one polynucleotide of interest to produce progeny plants; and selecting progeny plants comprising at least one mutation in the GRF transcription factor gene and the at least one polynucleotide of interest, thereby producing the plant comprising a mutation in an endogenous GRF transcription factor gene and at least one polynucleotide of interest.

The present invention further provides a method of producing a plant comprising a mutation in an endogenous GRF transcription factor gene and at least one polynucleotide of interest, the method comprising introducing at least one polynucleotide of interest into a plant of the present invention comprising at least one mutation in a GRF transcription factor gene, thereby producing a plant comprising at least one mutation in a GRF transcription factor gene and at least one polynucleotide of interest.

In some embodiments, the present invention provides a method of producing a plant comprising a mutation in an endogenous GRF transcription factor gene and at least one polynucleotide of interest, the method comprising introducing at least one polynucleotide of interest into a plant of the invention comprising at least one mutation in an endogenous GRF transcription factor gene, thereby producing a plant comprising at least one mutation in a GRF transcription factor gene and at least one polynucleotide of interest.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

In some embodiments, a method of producing a plant comprising a mutation in an endogenous GRF transcription factor gene and having a dwarf or short stature phenotype is provided, the method comprising crossing a plant of the invention (a first plant) having at least one mutation in an endogenous GRF transcription factor gene with a second plant that comprises the dwarf or short stature phenotype to produce progeny plants; and selecting progeny plants comprising the at least one mutation in the GRF transcription factor gene and the dwarf or short stature phenotype, thereby producing the plant having a dwarf or short stature and comprising at least one mutation in an endogenous GRF transcription factor gene.

The present invention further provides a method of controlling weeds in a container (e.g., pot, or seed tray and the like), a growth chamber, a greenhouse, a field (e.g., a cultivated field), a recreational area, a lawn, and/or a roadside, comprising applying an herbicide to one or more (a plurality) plants of the present invention growing in the container, growth chamber, field or greenhouse, thereby controlling the weeds in the container, growth chamber, greenhouse, field, recreational area, a lawn, and/or a roadside in which the one or more plants are growing.

In some embodiments, a method of reducing insect predation on a plant (or a plurality of plants) is provided, comprising applying an insecticide to one or more (a plurality) plants of the present invention, thereby reducing the insect predation on the one or more (a plurality) plants. In some embodiments the one or more plants may be growing in a container, a growth chamber, a field, a recreational area (e.g., playing field, golf course), a lawn, roadside, or a greenhouse.

In some embodiments, the present invention provides a method of reducing fungal disease on a plant, comprising applying a fungicide to one or more (a plurality) plants of the present invention, thereby reducing fungal disease on the on the one or more (a plurality) plants. In some embodiments the one or more plants may be growing in a container, a growth chamber, a field, a recreational area (e.g., playing field, golf course), a lawn, a roadside, or a greenhouse.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), Cannabis (e.g., *Cannabis sativa, Cannabis* indica, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleraceae, B. rapa, B. juncea*, and/or *B. nigra.*

In some embodiments, a plant that may be modified as described herein is corn (i.e., maize, *Zea mays*, optionally wherein the corn plant comprises a short stature/semi-dwarf phenotype.

In some embodiments, a plant that may be modified as described herein is wheat (e.g., *Triticum aestivum, T. durum*, and/or *T. compactum*). In some embodiments, a wheat plant may comprise at least one non-natural mutation in an endogenous Growth Regulating Factor (GRF) transcription factor in its A genome, in its B genome, and/or in its D genome.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1

Modification of Endogenous Maize GRF Transcription Factor Family with Base Editing This example demonstrates the use of DNA base-editing to modify maize GRF transcription factors resulting in an increase in plant height and ear length.

Figure 9:
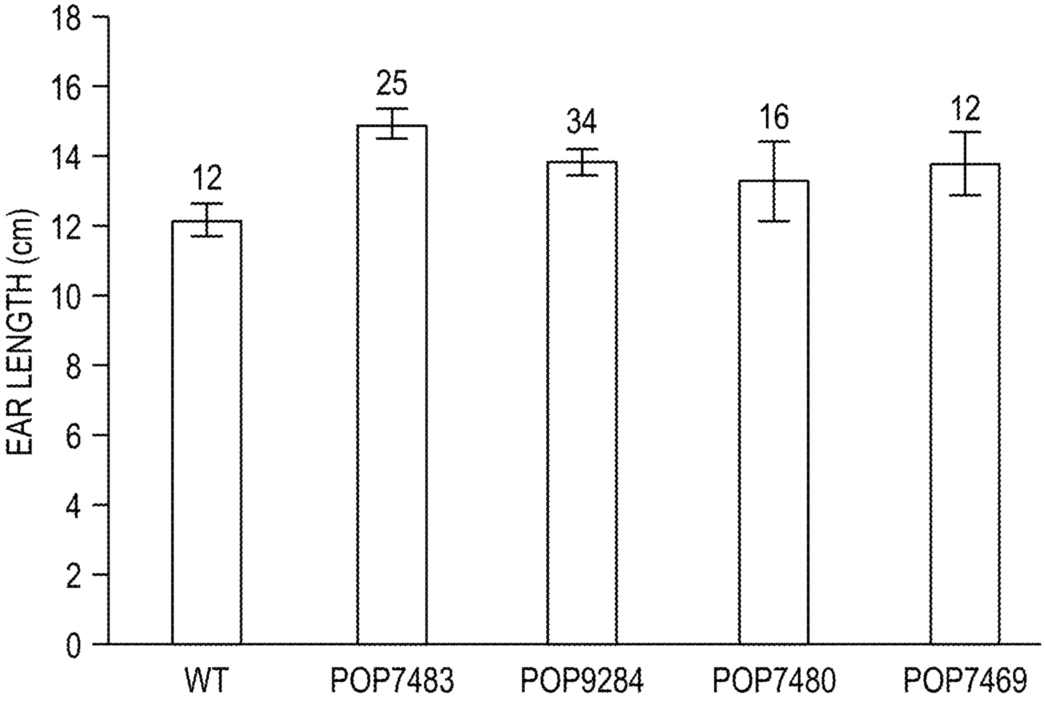
FIG. 9 provides a plot showing average ear length measurements from progeny of GRF4 family edits. X axis labels indicate the family of plants represented by the bar, WT indicating wild-type unedited lines, Population (Pop) 7483, Pop 9284, Pop 7480, Pop 7469 each indicating a family of progeny derived from an edited parent. Bars represent means, error bars represent 95% confidence interval around means, labels above error bars indicate number of measured samples for each family.
Figure 10:
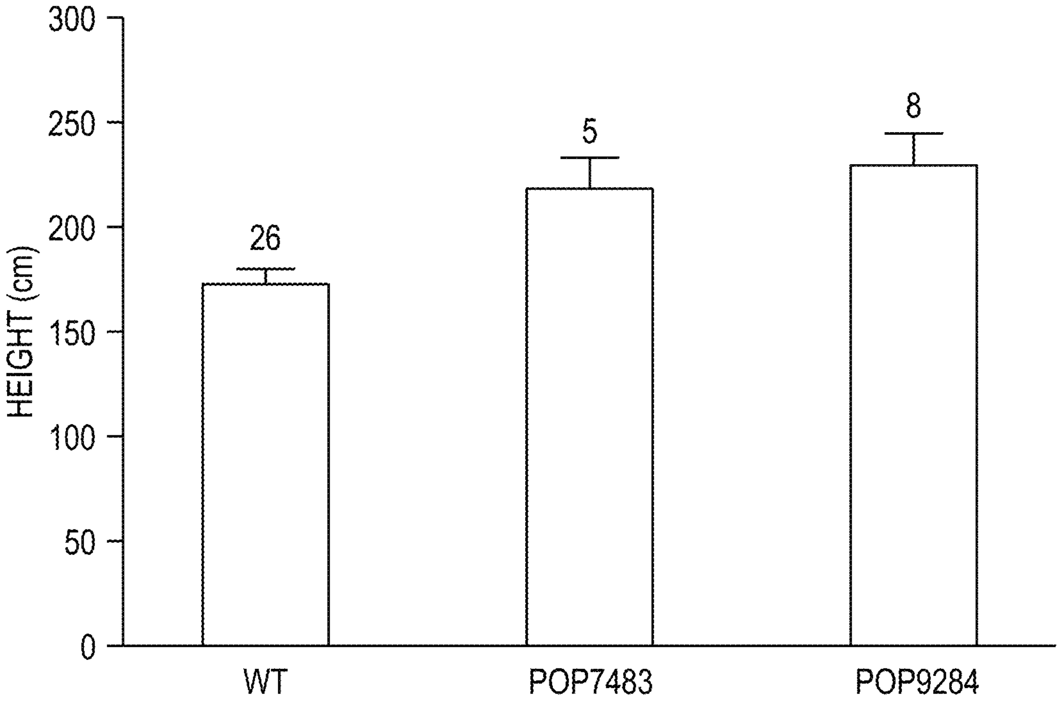
FIG. 10 provides a plot showing the average height from progeny of GRF4 family edits. X axis labels indicate the family of plants represented by the bar, WT indicating wild-type unedited lines, Pop 7483 and Pop 9284 each indicating a family of progeny derived from an edited parent. Bars represent means, error bars represent 95% confidence interval around means, labels above error bars indicate number of measured samples for each family.

The spacer sequence comprising SEQ ID NO:58 was selected for use in a Cas9 base editing approach targeting the conserved miR396 region of several maize GRF transcription factors. GRF6 and four other GRF loci were targeted with 100% match to the spacer sequence, FIG. 7. A vector encoding the spacer as well as a mutated Cas9 effector fused to a cytosine deaminase were introduced into maize dry-excised embryos (DEEs) using *Agrobacterium*. After transformation, we assayed regenerating plants (E0 generation) for edits at the GRF6 locus with standard next-gen-sequencing (NGS) methods and identified several families with base-edit mutations in the miR396 targets site, FIG. 8. We grew four different populations for trait testing in the next generation, three derived from selfed E0 plants that showed editing at GRF6 (Population 7483, 7480, 7469), and a fourth with seed derived from a backcross of plant 7469 to the transformation germplasm (Population 9284). These four populations were grown in controlled environment and transgene-free plants were selfed and subjected to trait testing. Our results show the progeny of E0 base-edited plants have increased ear length FIG. 9, and plant height FIG. 10. These results show that base editing within the miRNA396 target site of one of these GRF transcription factors results in increased maize plant growth.

Example 2

Increasing the mRNA Level of Maize GRF6 Transcription Factor with Cpf1 in-Frame Deletion Gene Editing.

This example demonstrates the modification of an endogenous maize GRF6 transcription factor, GRMZM2G034876 (GRF6) to disrupt miRNA396 action and increase GRF6 mRNA levels using a Cpf1 cutting nuclease.

Figure 12:
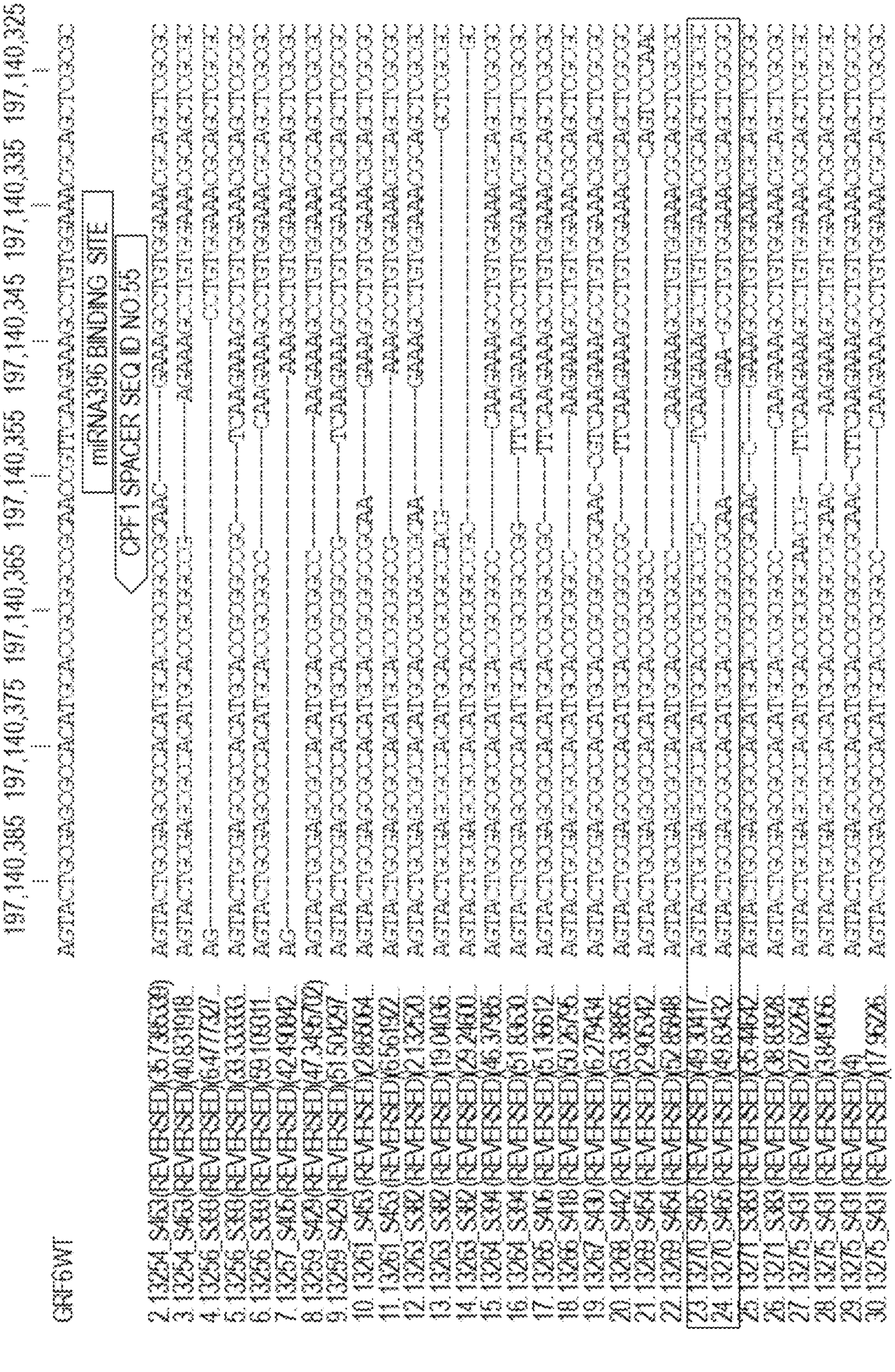
FIG. 12 shows edits achieved in maize GRF6 in E0 plants from Cpf1-based deletion construct. The top sequence is the wildtype GRF6 sequence. Also shown are the miR396 target sequence and the Cpf1 spacer (SEQ ID NO:55) positions. Individual reads from E0 plants are below. The boxed reads show the 6 bp and 9 bp deletions recovered from E0 plant 13270 which is used for subsequent analyses. Numbers next to each read name are the % NGS reads recovered. From top to bottom: SEQ ID NOs: 275, 276, 277, 278, 279, 280, 281, 282, 283, 284, 285, 286, 287, 288, 289, 290, 290, 291, 292, 293, 294, 295, 296, 297, 298, 299, 300, 301, 302, and 303.
Figure 13:
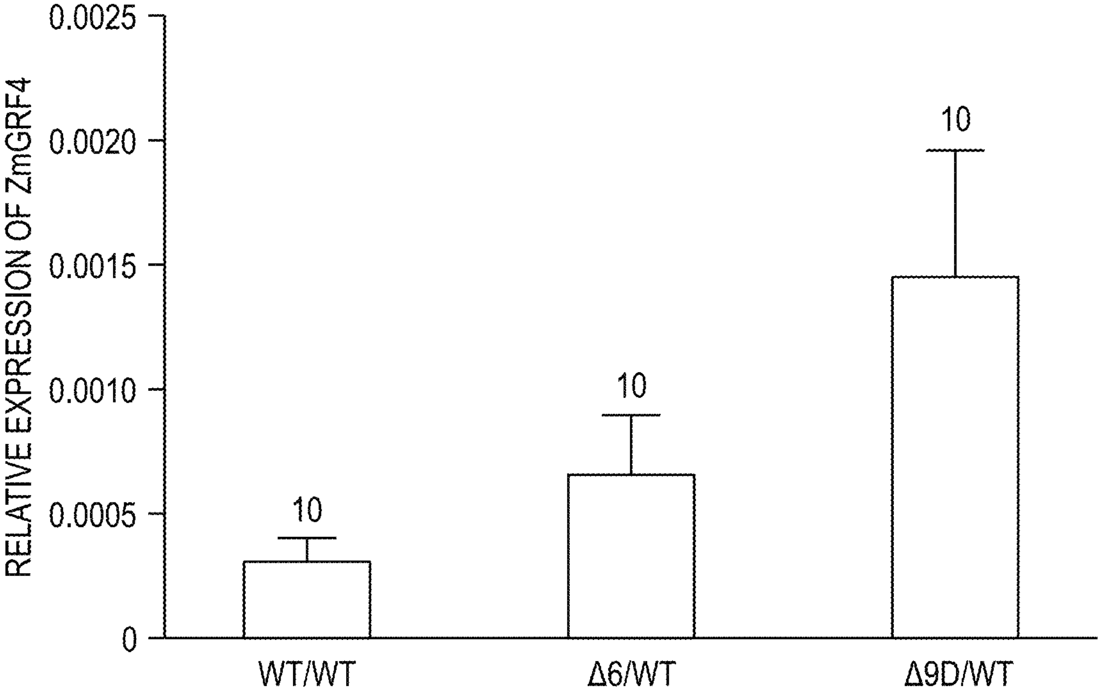
FIG. 13 provides a plot showing the average expression level of GRF4 in edited corn genotypes. X axis labels indicate the genotype of plants represented by the bar, WT/WT indicating wild-type unedited lines, Δ6/WT indicating lines heterozygous for a 6 bp deletion, and Δ9/WT indicating lines heterozygous for a 9 bp deletion. Y axis indicates expression of ZmGRF4 relative to endogenous control genes EF1α and Tubulin. Bars represent means, error bars represent 95% confidence interval around means, labels above error bars indicate number of measured samples for each family.

A spacer sequence comprising SEQ ID NO:55 with high specificity to the GRF6 target locus was designed. In this case only GRF6 was targeted with 100% specificity (FIG. 11). A vector encoding the spacer and a Cpf1-based nuclease were introduced into maize dry-excised embryos (DEEs) using *Agrobacterium*. After transformation, we assayed regenerating plants (E0 generation) for edits at the GRF6 locus with standard NGS methods and identified several families with in-frame deletions in the miR396 targets site, FIG. 12. Plant 13270 had ~50% reads for a 6 bp in-frame deletion and ~50% reads 9 bp in-frame deletion and was selected for further analysis. Plant 13270 was selfed and the progeny grown another generation (E1). In E1, a transgene-free plant containing both 6 bp and 9 bp deletions was backcrossed to the transformation germplasm (01DKD2). The progeny from this cross were grown, assayed for edits at GRF6, and subjected to trait testing. The GRF6 mRNA levels in leaf tissue of heterozygous 6 bp deletion, heterozygous 9 bp deletion, and a wildtype control plants were compared using standard quantitative PCR (qPCR) methods and we observed an increase in GRF6 mRNA levels in both heterozygous edit populations, FIG. 13. This example shows that in-frame deletion within the maize GRF6 miRNA396 target site using gene editing can increase GRF6 mRNA levels, even when the edit is in the heterozygous state. No statistical differences in plant phenotypes were observed, including, for example, plant height, ear length and 100 kernel weight. These results suggest it is one of the other GRFs and not GRF6 that explain the increased plant height and ear length resulting from the base edits in Example 1.

Example 3

Increasing the mRNA Level of Soy GRF Transcription Factor with Cpf1 in-Frame Deletion Gene Editing.

Figure 14:
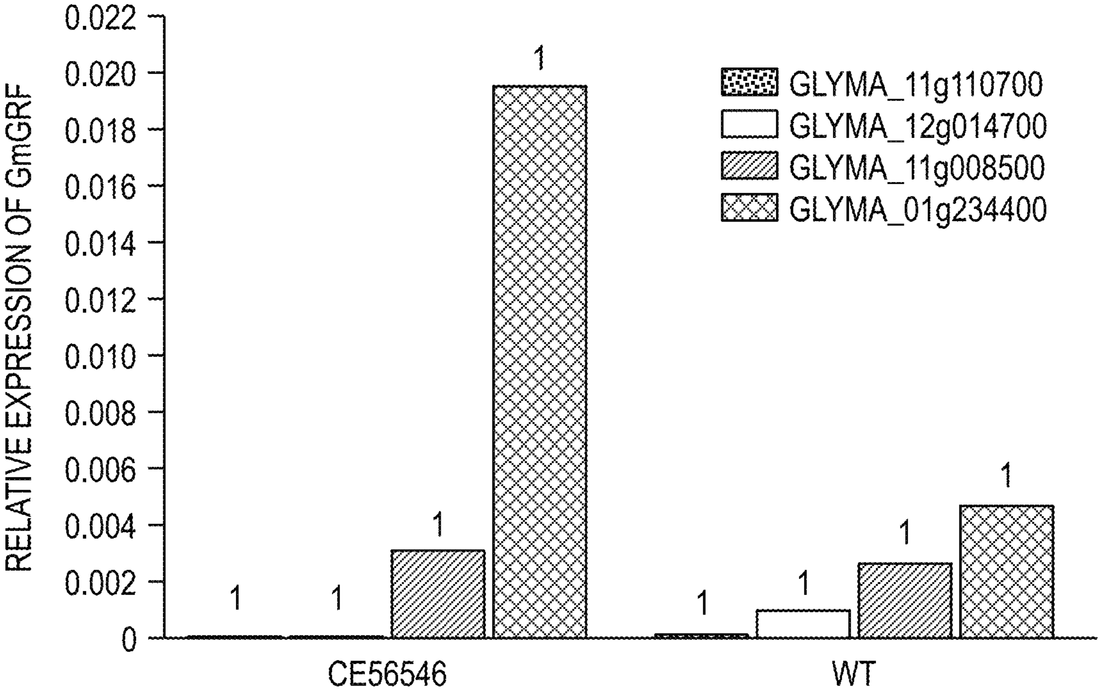
FIG. 14 provides a plot showing the expression level of a GRF in edited soybean plant compared to wild type. X axis labels indicate genotype of GRF family member (GLYMA_12g014700) allele. Y axis indicates expression of GmGRF relative to endogenous control gene ActII. Labels above bars indicate the number of samples included for each genotype.

This example demonstrates the modification of an endogenous soy GRF transcription factor (GLYMA_01g234400) to disrupt miRNA396 action and increase GRF mRNA levels. A spacer simultaneously targeting four different GRF transcription factors (GLYMA_01g234400 SEQ ID NO:97, GLYMA_11g008500 SEQ ID NO:110, GLYMA_12g014700 SEQ ID NO:108, GLYMA_11g110700 SEQ ID NO:112) was designed (TGATTCCACAGGCTTTCTTGAAC (SEQ ID NO:251)). A vector expressing the spacer and a Cpf1-based nuclease was transformed into Soy dry-excised embryos (DEEs) using *Agrobacterium*. Regenerating plants were assayed for deletions at all four target loci using standard NGS methods. A plant (CE56546) was identified with a 6 bp in-frame deletion in the miR396 target site in locus GLYMA_01g234400 at high % reads. Leaf tissue was sampled from this plant and the mRNA level of all four GRF loci were compared to wildtype controls using standard qPCR methods (FIG. 14). Only GLYMA_01g234400 showed an increase in mRNA levels consistent with the high % editing of this locus. The other GRFs assayed showed relatively low % edit and no increase in mRNA levels. These results show that in-frame deletions within the miR396 target of Soy GRFs can also increase mRNA levels in this species.

TABLE 1

Maize GRF transcription factor gene names as provided in the V1-V4 B73 corn strain gene models along with corresponding GRF name as use herein. Also provided are the chromosome positions of the GRF genes and miRNA binding sites (based on B73 RefGen v3)

| v1_gene_model | v2_gene_model | v3_gene_model | v4_gene_model | GRF Name | Chromosome | v3_Coordinates | v3_Binding Site Start Position |
|---|---|---|---|---|---|---|---|
| GRMZM2G178261 | GRMZM2G178261 | GRMZM2G178261 | Zm00001d033876 | GRF1 | 1 | 1:272414778 . . . 272420567 | |
| GRMZM2G119359 | GRMZM2G119359 | GRMZM2G119359 | Zm00001d045533 | GRF2 | 9 | 9:25722859 . . . 25725873 | 25723800 |
| GRMZM2G048993 | GRMZM5G893117 | GRMZM5G893117 | Zm00001d018260 | GRF3 | 5 | 5:211773221 . . . 211774543 | 211773927 |
| GRMZM2G018414 | GRMZM2G018414 | GRMZM2G018414 | Zm00001d033396 | GRF4 | 1 | 1:257245490 . . . 257249295 | 257247255 |
| GRMZM2G129147 | GRMZM2G129147 | GRMZM2G129147 | Zm00001d026240 | GRF5 | 10 | 10:140393394 . . . 140398705 | 140396302 |
| GRMZM2G034876 | GRMZM2G034876 | GRMZM2G034876 | Zm00001d017742 | GRF6 | 5 | 5:200344009 . . . 200348833 | 200346641 |
| GRMZM2G098594 | GRMZM2G098594 | GRMZM2G098594 | Zm00001d035965 | GRF7 | 6 | 6:60351912 . . . 60356302 | 60354519 |
| GRMZM2G041223 | GRMZM2G041223 | GRMZM2G041223 | Zm00001d002429 | GRF8 | 2 | 2:12201898 . . . 12208052 | 12204629 |
| GRMZM2G124566 | GRMZM2G124566 | GRMZM2G124566 | Zm00001d051456 | GRF9 | 4 | 4:155831622 . . . 155833517 | 155832779 |
| GRMZM2G105335 | GRMZM2G105335 | GRMZM2G105335 | Zm00001d052112 | GRF10 | 4 | 4:177151736 . . . 177154443 | 177152834 |
| | GRMZM5G850129 | GRMZM5G850129 | Zm00001d037117 | GRF11 | 6 | 6:108477686 . . . 108480099 | 108478777 |
| GRMZM2G067743 | GRMZM2G067743 | GRMZM2G067743 | Zm00001d000238 | GRF12 | 9 | 9:9818327 . . . 9820186 | 9819254 |
| GRMZM2G033612 | GRMZM2G033612 | GRMZM2G033612 | Zm00001d013555 | GRF13 | 5 | 5:13817620 . . . 13822440 | 13819823 |
| | GRMZM5G853392 | GRMZM5G853392 | Zm00001d013346 | GRF14 | 5 | 5:8708791 . . . 8711617 | |
| GRMZM2G099862 | GRMZM2G099862 | GRMZM2G099862 | Zm00001d007465 | GRF15 | 2 | 2:225827712 . . . 225832487 | 225830129 |

The foregoing is illustrative of the present invention and is not to be construed as limiting thereof. The invention is defined by the following claims, with equivalents of the claims to be included therein.

What is claimed is:

1. A corn plant or plant part thereof comprising a mutated gene encoding a Growth Regulating Factor (GRF) transcription factor that comprises the nucleic acid sequence of any one of SEQ ID NOs: 34-41 or 276-303, wherein the mutated gene comprises at least one non-natural mutation compared to an endogenous gene that encodes an endogenous GRF transcription factor and that comprises the sequence of (a) SEQ ID NO:254 when the mutated gene has the sequence of any one of SEQ ID NOs: 34-41 or (b) SEQ ID NO:275 when the mutated gene has the sequence of any one of SEQ ID NOs: 276-303, and wherein the corn plant or plant part thereof has increased levels of mRNA encoding the GRF transcription factor compared to a control corn plant or plant part thereof that is devoid of the mutated gene.

2. The corn plant or plant part thereof of claim 1, wherein the endogenous gene encoding the endogenous GRF transcription factor comprises a sequence having at least 90% sequence identity to the nucleotide sequence of SEQ ID NO:304.

3. The corn plant or plant part thereof of claim 1, wherein the at least one non-natural mutation is located in a region of the endogenous gene encoding the endogenous GRF transcription factor, the region comprising the sequence of SEQ ID NO:275 and the at least one non-natural mutation provides the nucleic acid sequence of any one of SEQ ID NOs: 276-303.

4. The corn plant or plant part thereof of claim 1, wherein the at least one non-natural mutation is located in a region of the endogenous gene encoding the endogenous GRF transcription factor, the region comprising the sequence of SEQ ID NO:254 and the at least one non-natural mutation provides the nucleic acid sequence of any one of SEQ ID NOs: 34-41.

5. The corn plant or plant part thereof of claim 1, wherein the mutated gene encodes the amino acid sequence of one of SEQ ID NOs: 43-47, 255, and 256.

6. The corn plant or plant part thereof of claim 1, wherein the mutated gene produces an mRNA having reduced miR396 binding compared to a control mRNA produced from a gene comprising the sequence of one of SEQ ID NOs: 1-3.

7. A corn plant, plant part thereof, or cell thereof comprising a guide nucleic acid that binds to a target site in a Growth Regulating Factor (GRF) transcription factor gene, wherein the guide nucleic acid comprises a spacer having the nucleotide sequence of any one of SEQ ID NOs: 48-71.

8. The corn plant, plant part thereof, or cell thereof of claim 7, further comprising a CRISPR-Cas effector protein that associates with the guide nucleic acid.

* * * * *

SEQUENCE LISTING

```
Sequence total quantity: 304
SEQ ID NO: 1            moltype = DNA  length = 22
FEATURE                 Location/Qualifiers
source                  1..22
                        mol_type = genomic DNA
                        organism = Zea mays
SEQUENCE: 1
ccgttcaaga aagcctgtgg aa                                            22

SEQ ID NO: 2            moltype = DNA  length = 22
FEATURE                 Location/Qualifiers
source                  1..22
                        mol_type = genomic DNA
                        organism = Zea mays
SEQUENCE: 2
tcgttcaaga aagcatgtgg aa                                            22

SEQ ID NO: 3            moltype = DNA  length = 22
FEATURE                 Location/Qualifiers
source                  1..22
                        mol_type = genomic DNA
                        organism = Zea mays
SEQUENCE: 3
ccgttcaaga aagcatgtgg aa                                            22

SEQ ID NO: 4            moltype = DNA  length = 62
FEATURE                 Location/Qualifiers
source                  1..62
                        mol_type = other DNA
                        organism = Zea mays
SEQUENCE: 4
cacatgcacc gcggccgcaa ccgttcaaga aagcctgtgg aaacgcagct cgcgccccag  60
tc                                                                  62

SEQ ID NO: 5            moltype = DNA  length = 62
FEATURE                 Location/Qualifiers
source                  1..62
                        mol_type = other DNA
                        organism = Zea mays
SEQUENCE: 5
cacatgcacc gtggccgcaa ccgttcaaga aagcctgtgg aatccaagac cgcctcctcg  60
cc                                                                  62

SEQ ID NO: 6            moltype = DNA  length = 62
FEATURE                 Location/Qualifiers
source                  1..62
                        mol_type = other DNA
                        organism = Zea mays
SEQUENCE: 6
cacatgaacc ggggacgcca tcgttcaaga aagcatgtgg aaggccagcc tggccatgcc  60
gc                                                                  62

SEQ ID NO: 7            moltype = DNA  length = 62
FEATURE                 Location/Qualifiers
source                  1..62
                        mol_type = other DNA
                        organism = Zea mays
SEQUENCE: 7
cacatgaacc ggggacgcca tcgttcaaga aagcatgtgg aagaccagcc tggccatgcc  60
gc                                                                  62

SEQ ID NO: 8            moltype = DNA  length = 62
FEATURE                 Location/Qualifiers
source                  1..62
                        mol_type = other DNA
                        organism = Zea mays
SEQUENCE: 8
cacataaaac gtggttgcca ccgttcaaga aagcatgtgg aaggccgaaa ggcaacaccg  60
ac                                                                  62

SEQ ID NO: 9            moltype = DNA  length = 62
FEATURE                 Location/Qualifiers
```

```
source                  1..62
                        mol_type = other DNA
                        organism = Zea mays
SEQUENCE: 9
cacatgcacc gcggccgcaa ccgttcaaga aagcctgtgg aagcgcagct cgtgcccccg  60
cc                                                                 62

SEQ ID NO: 10           moltype = DNA  length = 62
FEATURE                 Location/Qualifiers
source                  1..62
                        mol_type = other DNA
                        organism = Zea mays
SEQUENCE: 10
cacatcaata ggaaccgcca ccgttcaaga aagcctgtgg aaaaccaacc tagaaaggcc  60
ac                                                                 62

SEQ ID NO: 11           moltype = DNA  length = 62
FEATURE                 Location/Qualifiers
source                  1..62
                        mol_type = other DNA
                        organism = Zea mays
SEQUENCE: 11
cacatccacc gcgggaagag ccgttcaaga aagcctgtgg aagtgacctc ccccgccgcc  60
ta                                                                 62

SEQ ID NO: 12           moltype = DNA  length = 62
FEATURE                 Location/Qualifiers
source                  1..62
                        mol_type = other DNA
                        organism = Zea mays
SEQUENCE: 12
cacatgcacc ggggcaagaa ccgttcaaga aagcctgtgg aaatgtcctt ggccacgccg  60
gc                                                                 62

SEQ ID NO: 13           moltype = DNA  length = 62
FEATURE                 Location/Qualifiers
source                  1..62
                        mol_type = other DNA
                        organism = Zea mays
SEQUENCE: 13
cacattcacc gcgggaagag ccgttcaaga aagcctgtgg aagtgacctc ctcccccgcc  60
gc                                                                 62

SEQ ID NO: 14           moltype = DNA  length = 62
FEATURE                 Location/Qualifiers
source                  1..62
                        mol_type = other DNA
                        organism = Zea mays
SEQUENCE: 14
cacatgcacc gcggccgcaa ccgttcaaga aagcctgtgg aagcgcagct cgcgcccccg  60
cc                                                                 62

SEQ ID NO: 15           moltype = DNA  length = 62
FEATURE                 Location/Qualifiers
source                  1..62
                        mol_type = other DNA
                        organism = Zea mays
SEQUENCE: 15
cacatgcacc ggggcaagaa ccgttcaaga aagcctgtgg aaatgtcctt ggccacgccg  60
gc                                                                 62

SEQ ID NO: 16           moltype = DNA  length = 62
FEATURE                 Location/Qualifiers
source                  1..62
                        mol_type = other DNA
                        organism = Zea mays
SEQUENCE: 16
cacgtccacc gcggccgcgg ccgttcaaga aagcctgtgg aagccgccgc ggcaccggcg  60
gc                                                                 62

SEQ ID NO: 17           moltype = DNA  length = 62
FEATURE                 Location/Qualifiers
source                  1..62
                        mol_type = other DNA
                        organism = Zea mays
SEQUENCE: 17
cacatcaaca gaaaccgtca ccgttcaaga aagcctgtgg aaaatcaacc taagaagacc  60
ac                                                                 62
```

-continued

```
SEQ ID NO: 18          moltype = DNA  length = 62
FEATURE                Location/Qualifiers
source                 1..62
                       mol_type = other DNA
                       organism = Zea mays
SEQUENCE: 18
cacatgcacc gtggccgcaa ccgttcaaga aagcctgtgg aatccaagac cgcctcgtcg  60
tc                                                                 62

SEQ ID NO: 19          moltype = DNA  length = 1646
FEATURE                Location/Qualifiers
source                 1..1646
                       mol_type = other DNA
                       organism = Zea mays
SEQUENCE: 19
gagcgaagca aagcacatca cgagcccagc ctgcgcctgc ggagggaggg ggctcattaa  60
agaggggggcg cgagcgcgac cggccgcggg gagcaagcag cgcgcgagag agacaggttg  120
agatggcgat gccgtatgcc tctctttccc cggcaggcgc cgccgaccac cgctcctcca  180
cagccacggc gtccctcgtc cccttctgcc gctccactcc gctctccgcg ggcggcgggc  240
tgggcgagga ggacgcccag gcgagcgcga ggtggccggc cgcgaggccg gtggtgccgt  300
tcacgccggc gcagtaccag gagctggagc agcaggcgct catatacaag tacctggtgg  360
cgggcgtgcc cgttccgccg gatctcgtgg ttccaatccg ccgcggcctc gactccctcg  420
caacccgctt ctacggccaa cccacactcg ggtacggacc gtacctgggg aggaaactgg  480
atccggagcc cggccggtgc cggcgaacgg acggcaagaa gtggcggtgc tccaaggagg  540
ccgcccccgga ctccaagtac tgcgagcgcc acatgcaccg cggccgcaac cgttcaagaa  600
agcctgtgga aacgcagctc gcgccccagt cccaaccgcc cgccgccgca gccgtctccg  660
ccgctccgcc cctggcagcc gccgccgccg ccaccaccaa cggcagcggc ttccagaacc  720
actctctcta cccggccatc gccggcagca ctggtggtgg aggaggagtt ggcgggtccg  780
gcaatatctc ctccccgttc tcctcgtcga tggggggatc gtctcagctg cacatggaca  840
gtgctgccag ctactcctac gcagctcttg gtggtggaac tgcaaaggat ctcaggtaca  900
acgcttacgg aataagatct ctggcggacg agcacaacca gctgatcgca gaagccatcg  960
actcgtcgat agagagccag tggcgcctcc ccagctcgtc gttcccgctc tcgagctacc  1020
cacatctcgg ggcgctgggc gacctgggcg gccagaacag cacggtgagc tcgctgccga  1080
agatggagaa gcagcagccg ccctcgtcct tcctagggaa cgacaccggg gccggcatgg  1140
ccatgggctc cgcctccgcg aagcaggagg gccagacgct gcggcacttc ttcgacgagt  1200
ggcccaaggc gcgggactcc tggccgggcc tctccgacga gaccgccagc ctcgcctcgt  1260
tccccccggc gacccagctg tcgatgtcca tacccatggc gtcctccgac ttctccgtgg  1320
ccagctccca gtcgcccaac gatgactaat ggtgcgtgga tcgtcgcgtt ctggcccttt  1380
gtctgtcttc cctccagtcc tccacccacc gcgcagtagt agctgcggaa acagcccatg  1440
ctcctgtata tttgtcggtc attttccgtg tcagatctgt gtaccaaacc aagcggcggc  1500
ggccgtcgtc tctccccgcc tccgcctcgc ctcatgtggg tgggtgaaca tgagaccgtt  1560
ttgcttaggc tcaaagcttt gtgtgacccc actgatcggt tgtctgcgta ctacctgaaa  1620
gcctgctgct tttgtagcat tactgt                                       1646

SEQ ID NO: 20          moltype = DNA  length = 1718
FEATURE                Location/Qualifiers
source                 1..1718
                       mol_type = other DNA
                       organism = Zea mays
SEQUENCE: 20
aacccccacc tgaccttctc ttcctccctc ccccgaccgc ctgtctgtcc tccgcgcatc  60
cgttctctat cgaaagggag gaggaggagc gcgcgggagt gggctggggg cccaccgatg  120
ctgagctcgg cgtcctcggc cggggcggcc atggggatgg gcggcgggta ccaacaccag  180
ccgctgccac tgccgcagcg cggggcggcg gccgcggtct tcaccgccgc gcagtgggcg  240
gagctggagc agcaggcgct catctacaag tacctcatgg ccggcgtccc cgtcccgccc  300
gatctcctcc gccccgcccc ccacgccgcc gccttctcct tcgccagccc cgccgcgtcg  360
cccttctacc atcaccacca ccaccacccg tccctgagtt actacgccta ctacgggaag  420
aagctggacc cggagccgtg gcggtgccgc cgcaccgacg gcaagaagtg gcggtgctcc  480
aaggaggcgc accccgactc caagtactgc gagcgccaca tgcaccgtgg ccgcaaccgt  540
tcaagaaagc ctgtggaatc caagaccgcc tcctcgccgc cccagctgtc caccgtcgtc  600
accaccacca ccacccggga ggccgccgcc gcgacgcccc ttgagtccct cgcgggggcg  660
gggggtaagg ctcacggcct gtccctcggc ggcggggctg gctcgtcgca cctcagcgtc  720
gacgcttcga acgctcactt tcgctatggc agcaagtacc ctcttggagc taaatccgat  780
gctggcgagc tgagcttctt ctcaggagca ccagggaact ccaggggctt caccattgat  840
tctccagcag ataactcttg gcactccctg ccatccaacg tgccccccgtt tacactgtcc  900
aagggcagag actctggcct cctgcccggt gcctactcct actcccacat tgaaccaccg  960
caggtgctcg gccaggtcac catcgcctcg ctgtcacagg accaggagcg ccaccagtcg  1020
tcgttcagca gcggcggggc cggcgctggt ggattgctgg ggagcgtgaa gcaggagaac  1080
cagccgctga ggcccttctt cgacgagtgg cctgggacgc gggactcgtg gtcggagatg  1140
gacgacgcga ggtccagtag gacctccttc tcgacgaccc agctctccat ctccattccg  1200
atgcccagat gtgattgaga acgaagctcg tgcgcggcca gtaggtggcg ttgtcgcatg  1260
acgcgcaccc agcatcgcgc tcgctgctag cgagccaccg tcacccggtg attgatgccc  1320
tcatcctagc tatttgtttc gctgaatcgc attaagaaca gaactctatg taagagcagg  1380
atccttcctc atgtatcaat gggggcaatg aactccattc tgtttctatg gttgtagtac  1440
cgaccatgct ttgtatttgt tgtacccaga ccgagaatga aaaccgccca gtcgtcaggc  1500
gttgtcgtcg ctgcatcaga tgatccaagt gtattgtgtg ctttccaggc tgtgtaagat  1560
ctgatggcga atctgttact gcagtgtagg tgtgtagcat ctgtggtatg gtaccttttg  1620
ttgtgctact ggatctggat tgatgcaaaa tctggtgctg ccgtaggccc ctcttccttt  1680
tctctactgc tataataata atacatcttt tttttatg                          1718
```

```
SEQ ID NO: 21           moltype = DNA  length = 3536
FEATURE                 Location/Qualifiers
source                  1..3536
                        mol_type = other DNA
                        organism = Zea mays
SEQUENCE: 21
accgagcaca catacacact caccagcagg cagcagcagc tagccaagct ataccactag  60
aaccagagca caactcaaag caatgccgcc gcctcctcct cctccgcccc actcccacgc  120
ttcccatccc gcgccgcatg gacgcgagca gcactagcgc gggggcacac agcacggcga  180
gcgggcgggg gcgcgacgat ggacctgggc gggtcggtgg tgatggacgc gggcgcctcg  240
gagctgggcc tgctcggcgg cggatctagc aggctgctca agcacgggcg ggggcccaat  300
gcggcggggg gagacgacga cgtgtggggc ggcggcaggg ccaagcagcc caggacaggg  360
acagcgcccg tcgtcgccgg ggacgtggcg gctgccacca aggcggcggc ggcgccgttc  420
ctgctgggct cgtgcagtcc cggccacggc ggggagcaga tgctcagctt ctcgtccgcc  480
gccgccgccg ccgcggcctc gtgcgcctcc tccaccgctg cggctgatgg cggcggggcc  540
atgccgctgt actacgggac cccggcctct tgctcaggtg agcgcgagca cggcgacggc  600
gtacccgtgc tactgcttgt tgtggcggtg ccgcttgctg ctgcaaagct tacttctttt  660
tttcccgttg cttgttgatt ggattttggt gattgaaaag cttgctatcc acttcttctc  720
cagtattatt gcttttcggt tcgattcgat tcaccctgct ttctctcttt gctcttggtc  780
tcgtagctac agatttattt atttttactt ggttatgtct actgactgac tactgcttat  840
ccttaagctg atctgtgccc tcttccgttt cttctcctct tcttctttct tctagcttca  900
gttatttagt gcatctactc tagattcatg gggttttcat gaccagtgtt gactctttta  960
acctgccaat gatctttgta tggggttttc ctctctcttt tcgtcttctg gagatttaga  1020
ttagtgacga ctgtaaaagt tcttccacct ctggaaaaaa gaaatggttt taaatagtat  1080
tttaaaaaaa gctttattga atcatccgtg atatgtatcg acataagttt gcacttcttt  1140
ttgctgacat ccgccaacgc ttttcttgtc ctcaacggcg ccgcgatcgt gtggattcct  1200
ttttgtcacg ccgcctgctg ataatacgac tactagttct tattagagga agaatgaaaa  1260
agaatggcgt gatctacctc ggacctatac cttcacccct ttctcactca gaaacctaaa  1320
aaccaagaaa cagctaaaag agcatgaatg cacgcaagaa agtctcaaga atacaatgga  1380
gcctcgcgat tcaagttcac tgtcgggacc caacagtgtg gtccttggtc ggcttgctat  1440
ggacatcacc tataaatctg tgctgcttat caggtttctg atccttgcat gcaggcgctc  1500
cgttccaggt ttttgtgtct ttttttgctt gccttttatc ctgccctagg atcgtgttta  1560
ggaaacgctt gcatctcggc ggtcatctct atgaagcagt acacatgttt ttggctgcgc  1620
cttgttggct tccaccgttt tgctgctcat ctctcctaac tatgcctgcc tgtttgctcc  1680
ccgcaggatt gagctcggtg agcttgagca ccagcatgca gggggcaatg gccagggtga  1740
gggccccatt cacgccgtcc cagtggatcg agctcgaaca ccaggccctg atctacaagt  1800
acctggccgc gaacagcccc atacctcaca gcctcctcat ccccatcagg aggagcctcg  1860
cagcgtctcc ctacccgcct tcatacttcg gcacgagcac attggggtgg ggctctttcc  1920
agctgggcta ctccggcaat gcggatctgg agcctgggcg gtgccgccgg acggacggca  1980
agaaatggcg gtgctccagg gacgcggtcg ccgaccagaa gtactgcgag cgacacatga  2040
accggggacg ccatcgttca agaaagcatg tggaaggcca gcctggccat gccgcgaaag  2100
ccatgtccgc ggtggcggcg gcggctgctg ctgctgccca gcctgctgct ctggccggcg  2160
ccggagctcc tgctgctggc ctcactgtca atcagcacca gctgccggcg aagagctacg  2220
ccacgggtgc gactgaccct tgctctctgc aatataacag ggaactggtg aacaaacaga  2280
atgagagcga aaacatgcag gactccgaca acctctcgat gctgacttcc atgaacacag  2340
gaaacacagg cagcgtgttc ccattctcga aacaaaacac caatcctttt gaagtgacca  2400
gctcaaggct agagttcggc ctcgtttcat cggattcact gatgagttcc cctcacagtt  2460
ccttggagaa cgtcaacctg ctcggctcac agagtatgaa cgaacaccag aacccagcct  2520
ccctgcaaca cttcgtggac tggcccagga cgcctgccca gggaggcctt tcatggcccg  2580
aagctgaaga catgcaggct cagaggtcac agctctccat atctgctccc atggcatcct  2640
ccgagctatc gtcggcctcc acatccccca tccacgagaa gctgatgctg tcgcctctga  2700
agctgagccg cgagtacagc ccgactggtc tcggcattgc ggcgaacaga gacgaggcta  2760
gccagctaga agcaacctgg gcgacgatgt tccgtgactc ttcgatgggc ggtccgttgg  2820
gggaggttct ggccaagaac ggcaacgtgg aagcgagaaa ttacctgtcg gcgcctctga  2880
accttctcac cgactactgg gattcaagcc acgggatgga gtcctcccct gtgggcgttc  2940
tgcagaagac gaccgccttc ggatcggtct ccagcagtac agggagcagc cctagggttg  3000
agaaccacgg cgcctacgac ggtttcggca acctgcggga tgatctcggc tcaattgtag  3060
tgcgccatcc aagcatccgc cttgtgtgag ctttctgagt tctgaccatg gaaaactgca  3120
acaagacggc ggcccgcagc catagaagtg ggcatatggg ctactatgct aatcctcaaa  3180
gcgtgagggg ggggcattta cctcgtagtt tgtcatttga gactgatctc ctgtttttttg  3240
tcacttcagt tcttctttttg cttccctttt taacttggct ttgtaacttt caccttcctt  3300
ggatcgtgaa aagcgctgtg gtgtgtggtg tggatggatt tggtgcgccg ctgatgcata  3360
tcatcatgtg atagaagaag ccagtatccg tcgaggatta ctgcgagtat cgcctgtttg  3420
ttgttcatac gtcatactgc tgcactgcac ttcactgttt gtgtgcccgt tgttgcattg  3480
tatggttcgg ttatattaat ttacaaacag gtcgtgaggc tgcacattta gattcg      3536

SEQ ID NO: 22           moltype = DNA  length = 2086
FEATURE                 Location/Qualifiers
source                  1..2086
                        mol_type = other DNA
                        organism = Zea mays
SEQUENCE: 22
cgagcaccgc gcgcgcacag acacacactc accagcaggc agcagctagc tagctctcta  60
gcaacgagca caaaacgagc aatgccgcta gttccgtccc actccctcgc ttcccatccc  120
gcaccccatg gaagggagca gcactagcta gcgtgggaca gggcggggtg gtgtcgtggt  180
gatggaagcg ggcggcggcg cctcggaact cggcctgctc ggcgccggat ctggcaggct  240
gctcaagcac gggcggggcg acgcggcggg gggagaggac cacgggtggg tcgtcgtcgt  300
cggcggcggc ggcagggcca agcaggccag gaccgcgtcc gtcggcaccg gggacgcggc  360
```

```
ggccacggcg gccgtgccgt tcctgctggg ctcctgcggc ggccccggcc acggcgggga  420
acggatgctc agcttctcgt ccgccgccgc cgccgccccg gatgatggcg gtgccatgcc  480
gccgctgtac tacgggaccc cggcctcttg ctcaggattg atgagctcgg cgagggtgag  540
aggccccttc acgccgccgc agtggatcga gctggagcac caggccctga tctacaagta  600
cctgtccgcg aacagccccg tacctcacag cctcctcgtc cccatcagga ggagcgggag  660
cctcgcatcg tctccctacc cgcctcccta cttcggcacg agcacattcg ggtggggctc  720
cttccagctg ggctactccg gcaatgcgga tctggagcct gggcggtgcc gccggacgga  780
cggcaagaag tggcggtgct ccagggacgc ggtcgccgac cagaagtact gcgagcgaca  840
catgaaccgg ggacgccatc gttcaagaaa gcatgtggaa gaccagcctg gccatgccgc  900
gaaagccatg tccgcggtgg ccgtggcggc tgctgctgct gctgctaccc agcatgctgc  960
tgctctggcc ggcgccggag ctactgctgc tgctggcctc gctgtcaatc ggcaccggca  1020
gccggggaag agctatgcca cgggtgcgac tgatccatgc tctctgcaat atagcaggga  1080
actggcgaac aaactgtcga acgagagcga aaacatgcag gactctgaca atgtctcgat  1140
gctgacttcc atgaacacag gaaacactgc aggcagcgtg tttccgttct cgaaacagaa  1200
cactgctctt ttcgaagtga gcagctcaag gccagagttt ggccttgttc catcggattc  1260
actgacgagt tcacctcata gttccttgaa gagtgtcaaa aatctgctca gctcacggag  1320
tctgagtgag caccagagct ccgcctccct gcaacacttt gtggactggc ccaggacgcc  1380
acctgcccag ggaggtcttt catggcccga ggcagaggac atgcccagag ctcagaggtc  1440
ccagctctca gtatccgctc caatggcatc ctccgagcta tcatcggcct ccacatctcc  1500
catccacgac cacgagaagc tgattctgtc acctctcaag ctgggccgcg agtataccoc  1560
atctggcgtc gtcagcgctg cagcgaacag atacgaggtt agccagctag aagcgacctg  1620
ggcgacgatg ttccgcgact cttcgacggg cggcccgttg ggggaggttc tggccaagaa  1680
caacagcaac gcggaagcaa gaggttgccc gtcggcggcg ccacctctaa ccgactacta  1740
ctgctgggat tcaggccacg gcatgcagtc gtcccccgtg ggagttctgc agaggacgac  1800
cgccttcgga tcggtctcca gcagcacggg cagcagccct agggtcgaga accacggcgc  1860
ctgctgcgat ggtaccagca acctgatgga tgatctcggt tcagttgtag tgagacatcc  1920
cagcatccgc ctcttgtgag cccgctgggt tctggccatg gaaaaagcgt gagggggagc  1980
atttaccacg tagtttgtca tttgagactg atctcctgtt tctgtcacct gagttcttct  2040
tttgttgccc ttatacctgg ctttgtaact ctcaccttcg ttggat                 2086

SEQ ID NO: 23           moltype = DNA  length = 2328
FEATURE                 Location/Qualifiers
source                  1..2328
                        mol_type = other DNA
                        organism = Zea mays
SEQUENCE: 23
aggggcaagc tataattttg ttctgttgtc cagaacagcc aacaggtgtg ggctgtggg   60
cattcaattg cttttgcttc ctccgttccc ccatctggcc atctcccctt cccctgctcc  120
cccgaagcag caagccagcc tgcccacccg cagccatcac ctccgccgct ctccaccatg  180
aatcccatcc accagcacgg catcgtaccc aatccttcgt gactgttgcc tccgcgcatc  240
tccgggagca atggaaggag gccgagatgt gttcttaggt gcggcggcaa gggcgccgcc  300
gccgccgccg tcttgcccgt ttcacggatc cgctaccgcc acccgctccg gtggagcgca  360
gatgctcagc ttctcctcca atggcgtagc agggttgggt ctgtgctcag gtgccagcaa  420
gatgcagggt gtgttgtcga gggtgaggag gcccttcact ccgacgcagt ggatggagct  480
ggagcaccag gccctgatct acaagcactt cgctgtgaat gcccctgtgc cgtccagctt  540
gctcctccct atcaaaagaa gcctcaatcc atggagcagc cttggctcca gctcattggg  600
atgggcacca tttcgttccg gctctgctga tgcagaacca ggaagatgcc gccgcacaga  660
tggcaagaag tggcggtgct ctagagatgc tgtcggggac caaaaatact gtgagcgaca  720
cataaaacgt ggttgccacc gttcaagaaa gcatgtggaa ggccgaaagg caacaccgac  780
cactgcagat ccaaccatgg ctgtttctgg tggttcattg ttgcacagcc atgctgttgc  840
ttggcagcag cagggcaaaa gctcagctgc taatgtgact gatccattct cactagggtc  900
caacaggtga agtcacctga tcgtctgatc ctgcattgtt atactcattt ctgccactta  960
agtttgtgaa tttttatttt ctcaacattt ttttctcgaa cacgcaggag aactgtgcat  1020
catatattaa aagaagtaaa aaagtctaaa gaagaccaaa atctgccata agaggcagaa  1080
agagatagga agtgggaggg gcaccagcac actatatttt ctcaacataa atgacaatct  1140
atggttgata catgtgccag tctagcagtc agggttcagg acgtaccaaa acattgaaaa  1200
tgttatatcc tttagacatt gaaattttgt ccatagccat tcatagttga aaattttgtt  1260
cttgatttct ttcaactggt cagtgatttc ttcatgtaac ctgtcattga tgcattccat  1320
cttttgcccc gtgcccattc ctatatataa gattttatta ttatgtttgt ttgttcaaac  1380
aattatggta agcatgtgca aagaaaggca gtaggaagca ctataaataa ctgaaatgat  1440
atggtactta tgtcagtaca aactttagag ataggtgaat tctgttcatg atgacccttt  1500
caaattttga cgacttacta tagtcagcag tgaaagaaaa acaggacagt gtttcctttt  1560
ccttccatga acttgaaatg ttgactctgg tttgcaggaa tttgctggat aagcagaatc  1620
taggtgacca gttctctgta tccacttcca tggactcctt tgacttctca tcatcacatt  1680
cttccccaaa ccaagccaaa gttgcatttt caccggtggc catgcagcac gaacatgatc  1740
agctgtatct tgtgcatgga gccggcagct cagcagaaaa cgttaacaag tctcaggatg  1800
gtcagctgct agtctcgagg gaaacaattg acgacggacc tctgggcgag gtgttcaagg  1860
gcaagagttg ccagtcagca tccgcagaca tcttaactga ccattggact tcgactcgtg  1920
acttgcgtcc tccaaccgga gtcctacaaa tgtctagcag caacacagtg ccagcagaga  1980
atcacacgag taacagtagc tatctcatgg cgaggatggc gaattctcag accgtcccaa  2040
cactccactg agtgttcatc aggctggtct ttgttgggac cacaaaataa ctgaagccat  2100
gttgatgtcc tgagtttgct gatactaggt tttcagtcga gtcttgtaac tcctgtttta  2160
gagctgttat atgttcacgt catgtcgcct ttcattttcg gttcattcag atgggtgttc  2220
taataatttc tttccttctt acctgtgaag gatttgagtt ccaatctgag acgtgggttt  2280
gttctaactt ggaggtattt atgaatatta ggcacttctg atttccat               2328

SEQ ID NO: 24           moltype = DNA  length = 2279
FEATURE                 Location/Qualifiers
source                  1..2279
```

```
                        mol_type = other DNA
                        organism = Zea mays
SEQUENCE: 24
gagagagaga gaactagaag catatatggc gatgcccttt gcctccctgt ctccggcagc  60
cgaccaccgc ccctcctccc tcctccccta ctgccgcgcc gcccctctct ccgcggtggg  120
agaggacgcc gccgcgcagg cgcaacagca gcagcagcac gctatgagcg gcaggtgggc  180
agcgaggccg ccggcgctct tcaccgcggc gcagtacgag gagctggagc accaggcgct  240
tatatacaag tacctcgtcg ccggcgtgcc cgtcccgccg gacctcctcc tcccccctacg  300
ccgaggcttc gtctaccacc aacccgcccg taagcaagca cggcccccgc gccgcctccg  360
cacccccttca cactcacacg cacgtttaac cgcttttgca ctgcacaacc ccggccgccc  420
ggcggcggcg tccgtgcctt gatctggttg tttactcgga tcgagggatt cagatgtcct  480
ctccgtccgt ttgttaatcg gctccggtca tttcttaatc tcgtcctgga ttcggtcacg  540
aaaagctaga ggtcaagatt ttgctctcga ttactatatc cttgcctcat gttctaatgg  600
agtttatttt attggtctga tgtgattaga taggatgcta gccaggcttg tctccggcca  660
aaagcggcgg tttagtttat tgatgattgc ttctttcctt gggggattta ttcctgtctg  720
gttgttggga gcctaaccac gctcctattg ctgctgcggt ttactaacca tctgcgccag  780
tacacctact ccatggaccc caaaatacag ttcttccaac cattcccccc ctccatctgc  840
tttctcgcgg gcaaataaaa acgtgtagaa cgacggtgta gtaggcagat ctactccttg  900
tgccgctacg ctagcccgct accgaagatc gggcccgttt caaccggttc gttggtctga  960
gcggagctaa gatggggcgc atttcatttt ttggtccttt cgtctgattg gagaagtgcc  1020
cattccggta tcgctccccg gcctccaaat acgcaccgac acagaacgtg ttcgtacgca  1080
cgtacacatg gtatgcgcac cgtgctgctg gccatagccg ttgactcacc gggattcact  1140
cctctctcgc gtgtgtgtgt gtggcttcct tgcagttggg tacgggccct acttcggcaa  1200
gaaggtggac ccggagcccg ggcggtgccg gcgtacggac ggcaagaagt ggcggtgctc  1260
caaggaggcc gccccggact ccaagtactg cgagcgccac atgcaccgcg gccgcaaccg  1320
ttcaagaaag cctgtggaag cgcagctcgt gcccccgccg cacgcccagc agcagcagca  1380
gcagcaggcc cccgcgccca ccgctggctt ccagagccac cccatgtacc catccatcct  1440
cgccggcaac ggcggcggcg gcggcggggt aggtggtggt gctggtggcg gtggcacgtt  1500
cggcctgggg cccacctctc agctgcacat ggacagtgcc gctgcttacg cgactgctgc  1560
tggtggaggg agcaaagatc tcaggtactc tgcctacggg gtgaagtctc tgtcggacga  1620
gcacagccag ctcttgtccg gcggcggcgg catggacgcg tcaatggaca actcgtggcg  1680
cctgttgccg tcccaaaccg ccgccacgtt ccaggccaca agctaccctc tgttcggcgc  1740
gctgagcggt ctggacgaga gcaccatcgc ctcgctgccc aagacgcaga gggagcccct  1800
ctccttcttc gggagcgact tcgtgacccc gaagcaggag aaccagacgc tgcgcccctt  1860
cttcgacgag tggcccaagt cgagggactc gtggccggag ctgaacgagg acaacagcct  1920
cggctcctcg gccacccagc tctccatctc catccccatg gcgccctccg acttcaacac  1980
cagctccaga tcgccgaatg gaataccgtc aagatgaacc tgagtaacca tgcggacccc  2040
aacatctcag agctgacgac tctttgctgc tggcctggcc tcatcgtacc ttgaggcgtc  2100
aaggaatact tcattaccac tagtatcatg ctcctggatt ttcgaacaat atatatatgc  2160
ttatgtaccg ctatttctct catcttttac acttctttac ccgtttggaa ttgtatgttc  2220
tgcgtggcac ggttgttcat ttgacctttt tggatttgat tgaaagctcc gtttcttgc   2279

SEQ ID NO: 25           moltype = DNA  length = 1790
FEATURE                 Location/Qualifiers
source                  1..1790
                        mol_type = other DNA
                        organism = Zea mays
SEQUENCE: 25
ccaccacaca aacggacaaa cccctgcctc ccaccagaaa agcaagcaga ccacacccac  60
ccgcctctaa accaaccagc ctgtccccat tccccgtccc cggcgatgca cgccagcatc  120
cactccctcc cgtcagcctc ttcttctccc cctgatgagc gctgagttct gtgctgccgc  180
tgctggtgct gtggccatgg agctcggagt cggggatgtg atggggctgc agcaaggcat  240
cgccgccgcc accgggccat cgtccggaga cagcgacctg ggtcttctca agcgagcagg  300
cctcgcccag gcagccacct cctacccctc ccctttcctc gaccaacaga agatgctcag  360
gttctccaag gcggcggcgg ctcacacgtc gccctcaggc ctagacttcg gaggaggccc  420
gagcgagcag gctttcctgc tgtccaggac caagcggccg ttcactccgt cgcagtggat  480
ggagctggag caccaggctc tcatatacaa gtatctcaat gccaaggccc ccataccttc  540
cagcctgctc gtttccatca gcaagagctt caggtcatcc aacagagagc ttgacagact  600
ctctaacgca gtgagctgga ggcctcttta ccaaggctac gcaaacgcag actccgaccc  660
agaacctggg aggtgccggc ggacagacgg aaagaagtgg cggtgctcca aggaggcgat  720
gcctgatcac aagtactgcg agcgccacat caataggaac cgccaccgtt caagaaagcc  780
tgtggaaaac caacctagaa aggccaccaa ggaggtgact accgctgctg ctggctcgtt  840
gccgtgtgcc gggccacaag gtagcttgaa gaaggcaaaa gttaatgact ccaagccagg  900
cactggcagc tattggacag atagcttaaa caggacaatg ctgagcagag agaaggcaaa  960
caaaccgacg gacgacgagt ctttgctgct tagttcgacg aagaacagtc agcccacctt  1020
gtccctgctc actcaactga agcagcagaa caaaccagat aagttaggtc ccacaccgga  1080
aaatgagccg aactcggaca cgatgttgaa agcctggggt ggcagccacc acaagagcat  1140
ttcctccaca cagcgccatg acgctgaatc cctccaatca gtcctccaaa atttcagcct  1200
agcccagaat gacaggttgg agtcagaaaa gaacagatat tctgattccg tgctagtctc  1260
atcggctttc tattctgcag acggtccaca aactacctgc cttacaccta acatgacaca  1320
agtgcagcag gactgcatat caagctcctg ggagatgcct caaggtggac ctctaggcga  1380
gatcttaacg aactccaaga ttagtgagga cttaagcaag tgtggatcta ggtcatatgg  1440
ttggctattg aatcttgacc atgcaccatg attcctcaat ccatggagag cttgacatag  1500
atatctcacc acggatgcaa acaatgagtc aggaaaaaag aaggtccaaa tgaccgtact  1560
gtttacccca tgcatgctcg ttatctacat ttgtacttct atttttgtag tattcagctg  1620
ttgaattatc agttcttctg aatctggctg tatcttaaac aaattctagt ttccgtcaaa  1680
tgatatcttg cttgctagat gcttaatgtt tccttttcag cagaaacttc agtggtccat  1740
tttaatcaaa agaaaactgt ttcaagatca agctctagta agcaaagttc             1790
```

```
SEQ ID NO: 26           moltype = DNA  length = 1725
FEATURE                 Location/Qualifiers
source                  1..1725
                        mol_type = other DNA
                        organism = Zea mays
SEQUENCE: 26
gccgactgca ccccacacca cccccccacc tcagctcacc ttgcgctgcc cctgtgcctg  60
ctgcatgcct gacaccggcg ccatatgcat gatagcggat gatgatacta gcacgtcttc  120
ccgttcccga gctgcctctg acaccagcac aaacctggag actactacta gtattggagt  180
cccctccatt tccacctccc ttgccactga agcgagagct ctcggagccg tcgtcctctg  240
tctctcatcc ttcttcgttg ttgagcaaag cgggctcgag gaggagatga tgctgagcgg  300
gcacggcggc gggaggcgcc tgttcacggc gtcgcagtgg caggagctgg agcaccaggc  360
gctcatcttc aaatacatgg cctccggcgc gcccgtgccg cacgacctcg tcctgccgct  420
ccgcctcgcc accggcgtcg acaccgcgcc ctccctcgcc ttcccgcccc agccttcgcc  480
gtcgctggcg tactggggct gctatggcgc gggggcgccg ttcggccgca aggcggagga  540
cccggagccc gggcggtgcc ggcggacgga cggcaagaag tggcgatgct ccagggaggc  600
ccacggagac tccaagtact gcgagaagca catccaccgc gggaagagcc gttcaagaaa  660
gcctgtggaa gtgacctccc ccgccgccta ccgcccgtcc gcgttctcca tctcgccgcc  720
tcgcgcggcc gacgcgccgc cgccgccgcc gggcctcggc cacccgcagc agcagcatct  780
ccgccacggc gctctctctc cagcaggccg cgcccacgcc gctggcgctc tccagctcca  840
cctcgactcg agcctgcacg cggcgtcgcc gccgccgtcc taccacaggt acgcccactc  900
ccacgctcac tacacgccgc cgccgccgcc gtcgctctac gactacgggc agtccaagga  960
gcttcgggag gcggcggagc tcaggcggcg gcacttccac gcgctcgggg ccgacctgag  1020
cctcgacaag ccgctggccg acgccggggc cgcggagaag cccctgcggc gtttcttcga  1080
cgagtggccg cgggagagag gcgacacgag gccgtcgtgg gcgggggcgg aggacgcgac  1140
gcagctctcc atctccatcc ccgcggcttc gccctcctct gaccacgctg cctctgccgc  1200
cgcgcgatgc cacaacgatg ggagtgatcg gtgcatctcc tagctgcaac tgcaatgcaa  1260
gcctgcaacc gcgtggattg ttgttgattg gtgtagtttc ctagctgcaa ttcaagcctg  1320
caacagcgag cagtgagcag caaatgcgtg ggagggcac gcagctcagg ctgatgcgca  1380
aaatccgaag cgagtcaagc agcaatagga ctctaggtct atgatttgat cttcctttgt  1440
agcagtacgt taccaaaatg ttagctcgtt gttgttcggt gtgacatttt cgttcaggtt  1500
gctcctattg gctgctgcaa ctgcaacgct agctctgtgg cttttgtgtg ctttcagtct  1560
gcggtgcgag ccttgtcagc tcttttccgg tgacccacgc ctttgattcc tttctctgat  1620
tcctctgcgg gctctgtcat tttgatcgtt tgtcacatcc gtggattctt cctcgcggga  1680
ctactcccgt cacgaaatat aaacaaacgc acatggcttt ctttc                  1725

SEQ ID NO: 27           moltype = DNA  length = 2475
FEATURE                 Location/Qualifiers
source                  1..2475
                        mol_type = other DNA
                        organism = Zea mays
SEQUENCE: 27
cacaatcaca cgcgacgcgg caggcgtacg ccgtcgccgc gtctccgtcc gtacccgccg  60
ctggtctcgt ggaccgtgcg gtgggcgggt gcgacgcgac tgtgagagca gcgggggccc  120
ggtcggctct cgtcgcgcgg ctgcagccag cactgcatgc aggcacagca gcagccgcgg  180
acacggcaga ttctgcagcg cgcaccctgc atgctgtcac ggctgtgaat ggcctgcgca  240
gcgctggcag cctgtgccgc cggagaactg tcccagacac tgaccggtac atgtggagaa  300
tcacgtccaa ggcactgacc ggtcgcgctg ccgcgcgtgc cctccttgct tcgctcacct  360
cacacacgtc gtacgcccca cccgcatgct gcacggcacg tcccgtctgc tcctgccagg  420
ctcccatgat gacaccgagc gagcggtacg gaacacagcc tactacagtg tctgacgcct  480
gacggacggg ttagcgtaag cagccagatt cgcgtcccgg agctctcgcc tttgttgacg  540
aggtgagggg ggactgggca cggctgctgc tcggtcgtgc tgcccgttac agtagttgga  600
ggaacgcagc agggccgttg ggtcggagca ccggtgcccg tcgttcgtgt ggtcgatcca  660
atggcccaaa tctcttccgc ggcccaacaa acccacacac gcaggcgcct gcgaggcttg  720
ctcgtgcgac ccacagcagc ctgctgccgg gcgccgccca ctacaaataa aacccccttcc  780
ccatggacgt cgcccaagag actcactgct actcgcgctc ttgccaccgt ctactctcca  840
acccttctgc catccctcgg caccagctcg ctgacgctac cgccacccct accgccaggc  900
cgcatagccg tgctccgctc accttctctc gcgctacagt ctcaagggta gctagccaag  960
ctaccaagct cgtcaggagc gagagaaaga ggccgccggc ggtgcgcggg gatgatgatg  1020
atgagcagcg gccgggcggg cggcggggcc accgcggggc ggtacccgtt cacggcgtcg  1080
cagtggcagg agctggagca ccaggcgctc atctacaagt gcctggcgtc cggcaagccc  1140
atcccttcct acctcatgcc gccgctccgc cgcatcctcg actccgccct cgccacgtcg  1200
ccgtccctcg cctacccgcc gcaaccctca ctgggctggg gctgcttcgg gatgggcttc  1260
acccggaagg ccgacgagga cccggagccc gggcggtgcc ggcgcacgga cggcaagaag  1320
tggcgctgct ccaaggaggc gtacccggac tccaagtact gcgagaagca catgcaccgg  1380
ggcaagaacc gttcaagaaa gcctgtggaa atgtccttgg ccacgccggc cccggcgccg  1440
gcccccgccg ccgccacaac cgccaccgcc acctcatccc cggcgccgtc ctaccaccgc  1500
ccggcccacg acgccacgcc gtctccgtac cacgcgctgt atggaggcgg cggcggcggc  1560
ggcggtagcc cttactcggc gtcggcacgc ccaggagcaa ccggaggcgg cggcgcgtac  1620
caccacgcgc agcatgtgag ccccttccac ctccacctcg agaccaccca cccgcacccg  1680
ccgccgccct acaactactc cgccgaccag agggactacg cgtacgggca cgcggccgcc  1740
aaggaggtcg gcgagcacgc cttcttctcg gacggcgcgg gcgagcgggt cgaccggcag  1800
gccgcggcgg ggcagtggca gttcaggcag ctcggggtgg agacgaagcc gggccccacg  1860
ccgctgttcc ccgtcgccgg gtacgggcac ggcgcggcgt cgccgtacgg cgtggagatg  1920
ggcaaggacg acgacgagca ggaggagagg cgccgccagc actgcttcgt tcttggagcc  1980
gacctgcggc tggagcggcc gtcgtcgggc catggccatg gccatgacca tgacgacgcc  2040
gccgccgcgc agaagccgct ccggcccttc ttcgacgagt ggccgcacca gaagggggac  2100
aaggccgggt cgtggatggg gctcgacggc gagacgcagc tctccatgtc catccccatg  2160
gccgccaccg acctccccgt cacctcccgc ttccgtaacg gtgggcacta cgagtgatgc  2220
```

```
cacatcaaac ctggcgctgg aaactcggaa cgtatggtgc tgatgctgac catgagatgt  2280
accgtttcgc tcaaggccgg ccgtcatcac cacggccaca tcaaaccggt ttgaagaact  2340
tgggaaggcc gaatgaaacc tccagaagaa tgatctgtcc tctttttctc cattttcttt  2400
tttcttttag tattactctg tattgcttcg cgtgtaatat gttttcctgt aatatcaagt  2460
gagggcgttt ctgaa                                                   2475

SEQ ID NO: 28          moltype = DNA  length = 1539
FEATURE                Location/Qualifiers
source                 1..1539
                       mol_type = other DNA
                       organism = Zea mays
SEQUENCE: 28
atgatgctga gcgggcacgg cggcgggagg cgcctgttca cggcgtcgca gtggcaggag  60
ctcgagcacc aggcgctcat cttcaagtac atggcctcgg gcgcgcccgt gccgcacgac  120
ctcgtcctac cgctccgcct cgccaccggc gtcgacaccg cgccctccct cgccttcccg  180
ccgcagcctt cgccgtcgcg tacgacctgc gcgcttctct cctcccgacc cgacctcccc  240
cgtcctcgcc tcatgtttca ctctgatcat cgacagccat cagcccatca catcatcgct  300
gatgactttg tacgtgtgac cgtgcatgca gtggcgtact ggggctgcta cggcgcgggg  360
gcgccgttcg gccgcaaggc ggcggaggac acggagccgg ggcggtgccg gcggacggac  420
ggcaagaagt ggcggtgctc cagggaggcc cacggcgact ccaagtactg cgagaagcac  480
attcaccgcg ggaagagccg ttcaagaaag cctgtggaag tgacctcctc cccgccgcc  540
ggccccgctg cggcgtaccg accgtccgcg atctccacca tctcgccgcc ccgcgcggcc  600
gacgcgccgc cgccgagcct cgcctacccg cagcagcatc tcctccacgg cgcctcctcc  660
gcagcaggag cagcagcccg cgtccccgct ggcgctctcc agctccacct cgacgcgagc  720
ctgcacgcgg cggcggcggc ggcgtcgcca tcgccgccgc cgtcctacca caggtacgcc  780
cactacacac cgccagcgtc gtcgctcttc ccgggcggcg gctacggcta cgactacgac  840
tacgggcagt ccaaggagct caggcgacgg cacttccacg cgctcggggc cgacctgagc  900
ctcgacaagc cgctgcccga gcccgacacc ggctccgacg agaagcagcc cctgcggcgt  960
ttcttcgacg agtggccgcg ggagagcggc gacatggccg cggacgacgc gacgcagctt  1020
tccatctcca tccccgcggc ttcgccctcc gacctcgctg ctacctccgc ctccgccgcc  1080
gccgcgcgat tccacaacgg ggagtgatcg gtccatctcc tagctgcagc cctgcaacag  1140
cgtggattga ccgctgcatt tcctggctgc aatgcaagcc tgcaacagcg agcagtaagc  1200
cagtgacgtg gatgcatctc gtagcggcaa accctgcttc tgcctctgcg gtctgcgctg  1260
ctttgcgcgg gacggctcag gggctgaggc tcaaaaaagt ctgaaccgag tcaagcagta  1320
ctagggactc tatgacttgg tcttttgttc ttttgtagca gtacgttact cgtaccaaat  1380
gttgtttatt ttttgtgtga cattttcatt tcttccagtt ccagtctgtg atgcaagctt  1440
tgtcgctttt gtcagctctt tttcggtgac ccacgccggc cttcgtgatc gattccctta  1500
tacttatacc tgattcctct gccatattga tcgtttgtc                         1539

SEQ ID NO: 29          moltype = DNA  length = 1619
FEATURE                Location/Qualifiers
source                 1..1619
                       mol_type = other DNA
                       organism = Zea mays
SEQUENCE: 29
ggaaccctcc cgtgtcgacc tcaccccacc gcgcagccct gcacggccgc ggtcgcctat  60
aaggctagcc cagccagtgg tagcacgcac agcacagcag ccgccctgct cggcgtagga  120
gcagcccaga gcgagcgaga cagagggaaa gagacacggc cagccaggta aggcaaaaga  180
gagagggcgg aagcagcggc agagcggaga gggagagaga agagcatata tgggcatggc  240
gatgcccttt gcctccccgt ctccggcagc cgaccaccgc ccctcctccc tcctcccctt  300
ctgccgcgcc gcccctctct ccgcggcggg ggaggacgcc gcgcagcagc acgcgatgag  360
cggcaggtgg gccgcgaggc cggcgctctt caccgcggcg cagtacgagg agctggagca  420
ccaggcgctc atatacaagt acctcgtcgc cggcgtgccc gtcccgccgg acctcctcct  480
ccccctgcgc cgaggcttcg tcttccacca gccacccgcc cttgggtacg ggccctactt  540
cggcaagaag gtggacccgg agcccgggcg gtgccggcgt acggacggca agaagtggcg  600
gtgctccaag gaggccgccc cggactccaa gtactgcgag cgccacatgc accgcggccg  660
caaccgttca agaaagcctg tggaagcgca gctcgcgccc ccgccgcacg cccagccgca  720
gcagcagcag caggccccg cgcccgctgc tggcttccag aaccactcgc tgtacccgtc  780
gatcctcacc ggcaacggcg gcggcggggt aggtgctggt gctggtggtg gcacgttcgg  840
cctggggccc acctctcagc tgcacatgga cagtgccgct gcctacgcga ctgctgccgg  900
tggagggagc aaatatctca ggtactctgc atacggggtg aaatctctgt cggacgagca  960
cagcacgctc ttgtcgggcg gcatggatcc gtcgatgatg gacaactcgt ggcgcctgct  1020
gccatcccaa accaacacat tccaagccac aagctaccct gtgttcggca cgctgagtgg  1080
gctagacgag agcaccatcg cgtcgctgcc gaagacccag agggagcccc tctctttctt  1140
cggcagcgac ttcgtaaccg ccgccaagca ggagaaccag acgctgcgcc ctttcttcga  1200
cgagtggccc aagtcgaggg actcgtggcc ggagctgggc gaggacagca gcctcggctt  1260
ctcggccacc cagctctcca tctccattcc catggcgacc tccgacttct ccaacaccag  1320
ctccagatcg ccgggtggaa taccgtcgag atgaacgagt accgtgcatg tggatcccag  1380
cgtcttaggg ttgacgactc ttcggtgctg gcctcgtcgt atcatgctcc taaattttcg  1440
aacgatatat gccttatgta acgctatttc tctcattgtt acaacaccct ttacccgttt  1500
ggaattgtgt tgaagtggat ggtctgcgtt gctcggttgt tcattcgacc ttttttcaat  1560
ttggaaactc cgtttctttg tactcagtga tctgtgcaag tgcaatgatt cggtccatg   1619

SEQ ID NO: 30          moltype = DNA  length = 1750
FEATURE                Location/Qualifiers
source                 1..1750
                       mol_type = other DNA
                       organism = Zea mays
SEQUENCE: 30
```

```
cgcgatccaa gcctgccact acaaataaaa ctcccttccc catgaagctc acctaagtgc  60
ttcactcact cctgtcctct cctctcgacc agctgacctc gctgacggag cacacagcca  120
cgccgcagcg ccgcgtgggt gtctgtctat agccttgtag gtcgttcgca ggtaggtaac  180
cgtaacctag ctagctcgtc gggatgatga tgatgagcgg tcgagcggcc accgcggggc  240
ggtacccgtt cacggcgtcg cagtggcagg agctggagca ccaggcgctc atctacaagt  300
gcctggcgtc cggcaagccc atcccgtcct acctcatgcc accgctccgc cgcatcctcg  360
actccgccct cgccacgtcg ccgtcgctcg ccgccttccc gccgcaaccc tcgctggggt  420
ggggggggctg cttcgggatg ggcttcagca ggaagcccgc cgacgaggac ccggagcccg  480
ggcggtgccg gcgcacggac ggcaagaagt ggcgctgctc caaggaggcg tacccggact  540
ccaagtactg cgagaagcac atgcaccggg gcaagaaccg ttcaagaaag cctgtggaaa  600
tgtccttggc cacgccggcg ccggcctcct ccgccacaag cgccgccgcc gccgccacct  660
cctcgtccca ggcgccgtcc taccacagcc cggcccccgc cgtgccgtac cacgcgccct  720
acggcgccgc gtaccatcac acgcagacgc aggtgacgat gagccccttc cacctcctcc  780
acctcgagac cacccacccg cacccgccgc cgccgccgcc gccgccctac tactacgcgg  840
accagaggga ctacgcctac ggcaaggagg tcggcgagcg cgccttcttc tccgacggcg  900
cgggcgagag ggaccggcag cagcaggccg cggggcagtg gcagttcaag cagctcggga  960
cgatggaggc gacgaagcag ccgtgcacca cgccgctgct cgtccccgcc gccgggtacg  1020
gccacggcgc ggcgtcgccg tacggcgtcg gtcaggccaa ggaagacgag gaggaggagg  1080
aaacgcggcg gcagcagcag cactgcttcg ttcttggcgc cgacctgcgg ctggcggagc  1140
ggccgtcggg ggcacatgac gccgccgcgc agaagccgct ccggcatttc atcgacgagt  1200
ggccgcacga gaaggggagc aataaggcgg ggtcgtggat ggggggggctc gacggcgaga  1260
cgacgcagct ctccatgtct atcccgatgg cggccgctgc cgacctcccc gtcacctccc  1320
gctaccgtac gtgatggcgg cgcgcactat gagtgattgc cagcaagaaa tgttttgtgg  1380
ttgctgcgac ctcgaggtgg cgaggccaca tgaaaaaaaa atactggagc tggaacacga  1440
gtggttcttt cctgtgccgt tttgctcagg gccggtcggc acggtttgaa gaagttggga  1500
agagaagtaa aataaacctc cttgggagtg ttacgtttcc tgtaattgct tgcttccttt  1560
gctgtacctg tgagacgacg cttagtgcta gaagtgaggg cctttcctga tctcagctct  1620
ggtctggatt tgcctttttcc cgctgtcgga ttcctctgcc tgtctgtgat ggtttgtctg  1680
tgatggtttg tgctcagagc ctgcagcgaa tactaaaccg cagtaattaa tcaccatgct  1740
tcacccgaca                                                          1750
```

```
SEQ ID NO: 31          moltype = DNA  length = 852
FEATURE                Location/Qualifiers
source                 1..852
                       mol_type = other DNA
                       organism = Zea mays
SEQUENCE: 31
cttcttccct cctctcgaga agctgcctgc tacccgcgcg ctgcctctcc cttccactcc  60
ataccatacc gccacgacaa cgtcgacaag cgcaataccg gagccctccg aaatggccga  120
ggacaaggag accgactcgc cgcagccgcc ggccaagctg ccccgcctct cccgcgccga  180
cacgagcgcc ggagaggtga ccatggcggc ctcgtcgccg ctggttcttg ggctggggct  240
gggcctcggc gggcgcggcg gcggcggcga gcgagacgcg gatgtgtccc ccgcgacggt  300
gactcccaag aggccgtcgg cgctgacgtt catgcagcag caggagctgg agcaccaggt  360
gctcatctac cgctacttcg ccgcgggcgc gccggtgccg gtgcacctgg tgctccccat  420
ctggaagagc gtcgccgcgt cctccttcgg cccgcagcgc tttccctcgc tgatgggcct  480
gggcagcctg tgcttcgact accgcagcag catggagccg gagcccgggc ggtgccggcg  540
cacggacggc aagaagtggc ggtgctcccg cgacgtggtg ccgggccaca agtactgcga  600
gcggcacgtc caccgcggcc gcggccgttc aagaaagcct gtggaagccg ccgcggcacc  660
ggcggcggcg gccggcggca gcagccccgt cctccgggtc gccgcgcccc agcacgtgct  720
cggcctctcc tcgcccacca gcgtcctcct cgcccacggc gccgcgcgtg ccacgtgagt  780
agcgcgccgc cgcgggccga ccgatggtgc cgtggtctac tggtcttggg cctcggaatc  840
acgaggggca aa                                                       852
```

```
SEQ ID NO: 32          moltype = DNA  length = 1725
FEATURE                Location/Qualifiers
source                 1..1725
                       mol_type = other DNA
                       organism = Zea mays
SEQUENCE: 32
gccgcccagc gcccacccac acccctgcct cccaggctcc cactacctgt ccccaacaat  60
gcacaccaac atccactctc tcgtcaggct cctctccccc aaaaatgagc gctgagttct  120
gcgctgctgc cggtgtcgtg gccatggagc tcggagtcgg agatgtgctg gggctgcagc  180
aaggcatcgc aatcaccgcg ccatcgccca gggacagcga cctgggtctt ctcaagcgag  240
caggcctcac ccaggctgcg gctgctgccc cctacccctc cccttccctt gacgaggaga  300
agatgctcag gttctccaag gcggctcaca cattgcactc aggcttggat tttggaggcc  360
caggtgagca ggctttcctg ctgtccagga ccaagatgcc atttactccc tcgcagtgga  420
tggagctgga gcaccaggct ctgatataca agtacctcaa tgcaaaggcc cccccatacc  480
ttccagcctg ctcatttcaa tcagcaagag cttcagatca tccaatagag agcttgacag  540
acttctctaa cgcagtgagc tggaggcctc tgtatcaagg ctacacaaat gcagactctg  600
acccagaacc tgggagatgc cgacgaacgg atggaaagaa gtggcggtgc tccaaggaag  660
caatggctga tcacaagtac tgtgagcggc acatcaacag aaaccgtcac cgttcaagaa  720
agcctgtgga aaatcaacct aagaagacca ccaaggaggt gcctgctgct gctggctcat  780
tgccatgtgc tgggccacaa ggtagcttga agaaggcaaa agttaatgac tccaagccag  840
gcactgtcag ctattgggca gatagtttaa acaggacaat gttgagcaga gagaaagcaa  900
acaaaccgac ggaagatagc tctttgctgc ttacttctac gaacagccaa cccaccttgt  960
ccctgctctc tcagctgaag cagcaaaaca aaccagataa gttaggcccc acactggaaa  1020
atgagtcaaa cccagacaca atattgaaag cctggggtgg caaccagcct agccacaaga  1080
gcatttcctc tacagagcgc catgatgctg aatccctcca atcagtcctt caaaatttca  1140
gcctagccca gaatgagaag atggagtcag aaaagaacaa atattctgat tccgtgctag  1200
```

```
tttcgtcgac tttctattct gcagacggtc caagagctac ctgccttaca cctaacatga  1260
cacaggtgaa gcaggattgc atatcaagct cttgggagat gcctcaaggt ggacctctag  1320
gcgaaatctt aacgaactcc aagaatagca aggacttaag caagtgtaaa ccaaggtcat  1380
atggttggtt gttgaatctt gaccatgcac catgattcct caatccatga agagcttgac  1440
atagatatcc catcatgtag gcaaacaatg gtcagaaaaa ggttatgacc acattgcttg  1500
ccccatgcat gcttgctatc tacatttgta tttctgttac gtagcattta gctagttgaa  1560
ttatcagttc ttctggatac ggctgtatct taaacaagtt ctagtttgtg tcagatgata  1620
tcttgcttgc tagatgtttc atgttccact ttcaacagga acttcagaca accactttga  1680
ttgacagaaa actgtttgaa gaaccagctc tagtaaacaa ggttc                  1725

SEQ ID NO: 33           moltype = DNA  length = 1668
FEATURE                 Location/Qualifiers
source                  1..1668
                        mol_type = other DNA
                        organism = Zea mays
SEQUENCE: 33
aaatccaaag cgagcagatc ccccgcccct aaccgactcc cctcgcttcc attccattaa  60
tggccgccac caagagccct ccaacacaca cctgacctcc ccttcccccc tctctccgcc  120
gcccgttccc cgcgcctccg cccgtacgtc ccgttcccgg tcggccggcc ggtccaaagg  180
gaggggagga ggaggaacgc gggagtcggg gcccgcaccg atgctgagct cggcatcctc  240
ggccgcggga gcggccatgg ggatgggcgg cggcgggtac gcgcaccagc ccccgccaca  300
gcgcacggtc ttcaccgccg cgcagtgggc ggagctggag cagcaggcgc tcatctacaa  360
gtacctcatg gccggcgtcc ccgtcccgcc cgacctcctc ctccccgtcc gccccggccc  420
cgccgccgcc ttctccttcg ccggccccgc cgccgcgtcg cccttctacc accaacacca  480
cccgtccctg agctactacg cctactacgg caagaaactg gacccggagc cgtggcggtg  540
ccgccgcacc gacggcaaga agtggcggtg ctccaaggag gcgcaccccg actccaagta  600
ctgcgagcgc cacatgcacc gtggccgcaa ccgttcaaga aagcctgtgg aatccaagac  660
cgcctcgtcg tcgtcgcccg cgcacccgtc gccgccccag ctgtccaccg tcaccaccac  720
cgcgcctctc gagccccttg cagcggcggg gggcaaggtc cacggcctgt ccctcggcgg  780
cggcgctgct ggctcgtcgc acctcggcgt cgatgcttcg aatgctcact atcgttatgg  840
tagcaacagg taccctctcg gagctaaacc ggacggcggc gagttgagct tcttctcagg  900
agcgtcatcg gggaacaact cgaggggcgg cttcaccatc gactctccat cagataacaa  960
ctcgtggcac tccgccctgg cgtccagcgt gcccccgttc acgctgtcga cgaagagcgg  1020
ggactccggc ctcctgcccg gcgcctacgc ctcctactcc cagtcccact cccacatgga  1080
gccgccgcgg gagctcgggc aggtcaccat cgcctcgctg gcgcaggagc aggagcgcca  1140
gcagccgttc agtggtggga tgctcgggaa cgtgaagcag gagaaccaga accagccgct  1200
gcggcccttc ttcgacgagt ggcccgggac gcgggcggac tcgtggccgc cggagatgga  1260
cggcgcgccg cgggccggca ggacctcctt ctcctcctcc accacccagc tctccatctc  1320
catcccgatg cccagatgcg actgacgagg aaccgtcgat cgggcggcca ctagacggtg  1380
gacgctcacg ctcactagtg cgctgtcgcc tggagtggag atcgatcgtc acgccgccgc  1440
cgcctacgcc ctcgtcctac ctatttgttt tgccgtagtg tattgtaccg acctcattaa  1500
gaacagaaca gaacagaagt ctctgtgtaa gagccggctc cttcctgttc ctatggtttg  1560
tactagtagc gtgctttgta tttgttgtac ccctcaagac cgagaatgaa acccgcccgc  1620
cgtcagtctg tctttgcgtt ttagtagatg atgcgagtgt ttcgtgtg               1668

SEQ ID NO: 34           moltype = DNA  length = 27
FEATURE                 Location/Qualifiers
misc_feature            1..27
                        note = Synthetic binding site of GRF5
source                  1..27
                        mol_type = other DNA
                        organism = synthetic construct
SEQUENCE: 34
aaccgttcaa gaaagcctgt aaaaacg                                      27

SEQ ID NO: 35           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 35
aaccgttcaa gaaagcctat aaaaacg                                      27

SEQ ID NO: 36           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 36
aaccgttcaa gaaagcctgt caaaacg                                      27

SEQ ID NO: 37           moltype = DNA  length = 27
FEATURE                 Location/Qualifiers
misc_feature            1..27
                        note = Synthetic binding site of GRF6
```

```
source                  1..27
                        mol_type = other DNA
                        organism = synthetic construct
SEQUENCE: 37
aaccgttcaa aaaagcctat aaaaacg                                        27

SEQ ID NO: 38           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 38
aaccgttcaa gaaagcctct caaaacg                                        27

SEQ ID NO: 39           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 39
aaccgttcaa gaaagcctgt acaaacg                                        27

SEQ ID NO: 40           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 40
aaccgttcaa aaaagcctgt ggaaacg                                        27

SEQ ID NO: 41           moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 41
aaccgttcaa aaaagcctgt aaaaacg                                        27

SEQ ID NO: 42           moltype = AA  length = 9
FEATURE                 Location/Qualifiers
source                  1..9
                        mol_type = protein
                        organism = Zea mays
SEQUENCE: 42
NRSRKPVET                                                            9

SEQ ID NO: 43           moltype = AA  length = 9
FEATURE                 Location/Qualifiers
REGION                  1..9
                        note = Mutant GRF miRNA binding site
source                  1..9
                        mol_type = protein
                        organism = synthetic construct
SEQUENCE: 43
NRSRKPVKT                                                            9

SEQ ID NO: 44           moltype = AA  length = 9
FEATURE                 Location/Qualifiers
REGION                  1..9
                        note = Mutant GRF miRNA binding site
source                  1..9
                        mol_type = protein
                        organism = synthetic construct
SEQUENCE: 44
NRSRKPIKT                                                            9

SEQ ID NO: 45           moltype = AA  length = 9
FEATURE                 Location/Qualifiers
REGION                  1..9
                        note = Mutant GRF miRNA binding site
source                  1..9
```

```
                        mol_type = protein
                        organism = synthetic construct
SEQUENCE: 45
NRSKKPIKT                                                     9

SEQ ID NO: 46           moltype = AA  length = 9
FEATURE                 Location/Qualifiers
REGION                  1..9
                        note = Mutant GRF miRNA binding site
source                  1..9
                        mol_type = protein
                        organism = synthetic construct
SEQUENCE: 46
NRSRKPVQT                                                     9

SEQ ID NO: 47           moltype = AA  length = 9
FEATURE                 Location/Qualifiers
REGION                  1..9
                        note = Mutant GRF miRNA binding site
source                  1..9
                        mol_type = protein
                        organism = synthetic construct
SEQUENCE: 47
NRSKKPVKT                                                     9

SEQ ID NO: 48           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 48
caaccgttca agaaagcctg                                         20

SEQ ID NO: 49           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 49
aaccgttcaa gaaagcctgt                                         20

SEQ ID NO: 50           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 50
cgcaaccgtt caagaaagcc                                         20

SEQ ID NO: 51           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 51
ctttcttgaa cggttgcggc                                         20

SEQ ID NO: 52           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 52
ttcttgaacg gttgcggccg                                         20

SEQ ID NO: 53           moltype = DNA  length = 20
FEATURE                 Location/Qualifiers
misc_feature            1..20
                        note = Synthetic spacer
```

```
source                  1..20
                        mol_type = other DNA
                        organism = synthetic construct
SEQUENCE: 53
tcttgaacgg ttgcggccgc                                              20

SEQ ID NO: 54           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 54
ttgaacggtt gcggccgcgg                                              20

SEQ ID NO: 55           moltype = DNA  length = 23
FEATURE                 Location/Qualifiers
misc_feature            1..23
                        note = Synthetic spacer
source                  1..23
                        mol_type = other DNA
                        organism = synthetic construct
SEQUENCE: 55
cacaggcttt cttgaacggt tgc                                          23

SEQ ID NO: 56           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 56
ttgaacggtt gcggccgcgg                                              20

SEQ ID NO: 57           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 57
cacaggcttt cttgaacggt                                              20

SEQ ID NO: 58           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 58
tttccacagg ctttcttgaa                                              20

SEQ ID NO: 59           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 59
tgcgtttcca caggctttct                                              20

SEQ ID NO: 60           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 60
ttcaagaaag cctgtggaaa                                              20

SEQ ID NO: 61           moltype = DNA  length = 20
FEATURE                 Location/Qualifiers
misc_feature            1..20
```

```
                        note = Synthetic spacer
source                  1..20
                        mol_type = other DNA
                        organism = synthetic construct
SEQUENCE: 61
aacggttgcg gccgcggtgc                                          20

SEQ ID NO: 62           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 62
aagaaagcct gtggaaacgc                                          20

SEQ ID NO: 63           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 63
tgaacggttg cggccgcggt                                          20

SEQ ID NO: 64           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 64
ttgaacggtt gcggccgcgg                                          20

SEQ ID NO: 65           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 65
acaggctttc ttgaacggtt                                          20

SEQ ID NO: 66           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 66
cacaggcttt cttgaacggt                                          20

SEQ ID NO: 67           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 67
agaaagcctg tggaaacgca                                          20

SEQ ID NO: 68           moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 68
gaaacgcagc tcgcgcccca                                          20

SEQ ID NO: 69           moltype = DNA  length = 20
FEATURE                 Location/Qualifiers
```

```
misc_feature           1..20
                       note = Synthetic spacer
source                 1..20
                       mol_type = other DNA
                       organism = synthetic construct
SEQUENCE: 69
caggctttct tgaacggttg                                              20

SEQ ID NO: 70          moltype = DNA  length = 20
FEATURE                Location/Qualifiers
misc_feature           1..20
                       note = Synthetic spacer
source                 1..20
                       mol_type = other DNA
                       organism = synthetic construct
SEQUENCE: 70
acaggctttc ttgaacggtt                                              20

SEQ ID NO: 71          moltype = DNA  length = 20
FEATURE                Location/Qualifiers
misc_feature           1..20
                       note = Synthetic spacer
source                 1..20
                       mol_type = other DNA
                       organism = synthetic construct
SEQUENCE: 71
agaaagcctg tggaaacgca                                              20

SEQ ID NO: 72          moltype = AA  length = 166
FEATURE                Location/Qualifiers
source                 1..166
                       mol_type = protein
                       organism = Escherichia coli
SEQUENCE: 72
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTD                 166

SEQ ID NO: 73          moltype = AA  length = 166
FEATURE                Location/Qualifiers
REGION                 1..166
                       note = Synthetic tRNA-specific adenosine deaminase Tad
source                 1..166
                       mol_type = protein
                       organism = synthetic construct
SEQUENCE: 73
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                 166

SEQ ID NO: 74          moltype = AA  length = 166
FEATURE                Location/Qualifiers
REGION                 1..166
                       note = Synthetic tRNA-specific adenosine deaminase Tad
source                 1..166
                       mol_type = protein
                       organism = synthetic construct
SEQUENCE: 74
SEVEFSHEYW MRHALTLAKR AWDEREVPVG AVLVLNNRVI GEGWNRSIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                 166

SEQ ID NO: 75          moltype = AA  length = 166
FEATURE                Location/Qualifiers
REGION                 1..166
                       note = Synthetic tRNA-specific adenosine deaminase Tad
source                 1..166
                       mol_type = protein
                       organism = synthetic construct
SEQUENCE: 75
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                 166

SEQ ID NO: 76          moltype = AA  length = 166
FEATURE                Location/Qualifiers
REGION                 1..166
                       note = Synthetic tRNA-specific adenosine deaminase Tad
source                 1..166
```

```
                        mol_type = protein
                        organism = synthetic construct
SEQUENCE: 76
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM PRQVFNAQKK AQSSTD                 166

SEQ ID NO: 77           moltype = AA  length = 228
FEATURE                 Location/Qualifiers
source                  1..228
                        mol_type = protein
                        organism = Rattus norvegicus
SEQUENCE: 77
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK               228

SEQ ID NO: 78           moltype = AA  length = 199
FEATURE                 Location/Qualifiers
source                  1..199
                        mol_type = protein
                        organism = Homo sapiens
SEQUENCE: 78
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 79           moltype = DNA  length = 621
FEATURE                 Location/Qualifiers
source                  1..621
                        mol_type = other DNA
                        organism = Petromyzon marinus
SEQUENCE: 79
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                            621

SEQ ID NO: 80           moltype = AA  length = 160
FEATURE                 Location/Qualifiers
REGION                  1..160
                        note = Synthetic polypeptide
source                  1..160
                        mol_type = protein
                        organism = synthetic construct
SEQUENCE: 80
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                       160

SEQ ID NO: 81           moltype = AA  length = 83
FEATURE                 Location/Qualifiers
source                  1..83
                        mol_type = protein
                        note = Bacillus phage AR9
                        organism = unidentified
SEQUENCE: 81
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 82           moltype = DNA  length = 1592
FEATURE                 Location/Qualifiers
source                  1..1592
                        mol_type = genomic DNA
                        organism = Medicago truncatula
SEQUENCE: 82
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
```

```
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaaattta ttttaataat cacatgtact  600
attttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggtttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592
```

```
SEQ ID NO: 83           moltype = DNA  length = 2000
FEATURE                 Location/Qualifiers
source                  1..2000
                        mol_type = genomic DNA
                        organism = Zea mays
SEQUENCE: 83
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccottta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000
```

```
SEQ ID NO: 84           moltype = RNA  length = 22
FEATURE                 Location/Qualifiers
source                  1..22
                        mol_type = other RNA
                        organism = Zea mays
SEQUENCE: 84
ttccacaggc tttcttgaac tg                                           22
```

```
SEQ ID NO: 85           moltype = RNA  length = 21
FEATURE                 Location/Qualifiers
source                  1..21
                        mol_type = other RNA
                        organism = Zea mays
SEQUENCE: 85
```

```
ttccacagct ttcttgaact t                                              21

SEQ ID NO: 86          moltype = RNA  length = 21
FEATURE                Location/Qualifiers
source                 1..21
                       mol_type = other RNA
                       organism = Zea mays
SEQUENCE: 86
gttcaagaaa gctgtggaag a                                              21

SEQ ID NO: 87          moltype = RNA  length = 21
FEATURE                Location/Qualifiers
source                 1..21
                       mol_type = other RNA
                       organism = Zea mays
SEQUENCE: 87
gttcaataaa gctgtgggaa a                                              21

SEQ ID NO: 88          moltype = RNA  length = 21
FEATURE                Location/Qualifiers
source                 1..21
                       mol_type = other RNA
                       organism = Zea mays
SEQUENCE: 88
ttccacagct ttcttgaact g                                              21

SEQ ID NO: 89          moltype = RNA  length = 21
FEATURE                Location/Qualifiers
source                 1..21
                       mol_type = other RNA
                       organism = Zea mays
SEQUENCE: 89
ttccacagct ttcttgaact t                                              21

SEQ ID NO: 90          moltype = RNA  length = 21
FEATURE                Location/Qualifiers
source                 1..21
                       mol_type = other RNA
                       organism = Zea mays
SEQUENCE: 90
gttcaataaa gctgtgggaa a                                              21

SEQ ID NO: 91          moltype = RNA  length = 21
FEATURE                Location/Qualifiers
source                 1..21
                       mol_type = other RNA
                       organism = Zea mays
SEQUENCE: 91
tcccacagct ttattgaact g                                              21

SEQ ID NO: 92          moltype = RNA  length = 21
FEATURE                Location/Qualifiers
source                 1..21
                       mol_type = other RNA
                       organism = Zea mays
SEQUENCE: 92
ggtcaagaaa gctgtgggaa g                                              21

SEQ ID NO: 93          moltype = RNA  length = 21
FEATURE                Location/Qualifiers
source                 1..21
                       mol_type = other RNA
                       organism = Zea mays
SEQUENCE: 93
tcccacagct ttattgaact g                                              21

SEQ ID NO: 94          moltype = RNA  length = 21
FEATURE                Location/Qualifiers
source                 1..21
                       mol_type = other RNA
                       organism = Zea mays
SEQUENCE: 94
ggtcaagaaa gccgtgggaa g                                              21

SEQ ID NO: 95          moltype = RNA  length = 21
FEATURE                Location/Qualifiers
source                 1..21
                       mol_type = other RNA
                       organism = Zea mays
```

```
SEQUENCE: 95
ttccacagct ttcttgaact g                                           21

SEQ ID NO: 96          moltype = RNA  length = 22
FEATURE                Location/Qualifiers
source                 1..22
                       mol_type = other RNA
                       organism = Zea mays
SEQUENCE: 96
ttccacaggc tttcttgaac tg                                          22

SEQ ID NO: 97          moltype = DNA  length = 957
FEATURE                Location/Qualifiers
source                 1..957
                       mol_type = other DNA
                       organism = Glycine max
SEQUENCE: 97
atgaataaga gtgggggagg agagatgagt aagtggccgt tcacaatgtc tcagtggcag  60
gaactggaac atcaagcttt gatttacaaa tacatggtgg ctggtcttcc tgtccctcct  120
gatctagtcc ttcccattca gaacagcttc cactccattt cccaaacctt cttgcaccat  180
ccctctacca ccatgagtta ttgttccttc tatgggaaga aggtggaccc ggagccagga  240
cgatgcagga ggactgatgg gaaaaagtgg aggtgctcca aggaagccta cccagactcc  300
aagtactgtg agcgacacat gcaccgtggc cgcaaccgtt caagaaagcc tgtggaatca  360
caaactatga ctcagtcatc atctaatgtg tcatcattga ctgtaactgc tggcagcagc  420
agcagtgcaa ctggaaattt ccataacctt accaccacaa atgcatatgg taatccccaa  480
gggactggtt ctggatcaga ccaaacccac tatcacatgg attccattcc ctatgggatc  540
ccaagtaaag aatacaggta ttttcaagga cctaaatctg agggaggtga acatagtttc  600
ttgtccaaaa ctttaggaag caacaaggtt cttcacatgg agtcacagat ggataacact  660
ttgatgccaa ccagtggagt tgcctcattc tctacattga gatcaaataa taattccatg  720
ttgcagggtg attatctgca gccttctttc ttatctagtg agtatgcctc agcagaaact  780
gtgaagcaag agggtcagtt ccttcgacct ttctttgatg aatggcctaa aaggagggac  840
tcatggtctg gtctggaaga tgagggatcc aaccacactc aactctcaat atccattcct  900
atgtcagcat caaatttctc tacaactagc tctcattccc cacatggtga gatttaa     957

SEQ ID NO: 98          moltype = DNA  length = 1377
FEATURE                Location/Qualifiers
source                 1..1377
                       mol_type = other DNA
                       organism = Glycine max
SEQUENCE: 98
atggaagcta agcctcttcg aactgttccc tcttcacaca acacttctgg aggtggaccc  60
cagaagaaga ttgacatggg acacaagatg gtaggtgatg ttggtgttgt tgttgttgat  120
gaaagaaaga gggttgttgt ggtcaaggaa gagaaagaga acacttcttc ctacagtgtt  180
gaacttcatc tcggggttga tgcttctcat tctgctccac aagaaataaa ccatgtgatc  240
actgaagctc agaggcgtga gcttcaccat caagttttca tcttcaacca tttggcatat  300
aatcttcctc ctccttatca ccttgtgcaa ttcccgagca acatgtcaga atacagtttc  360
ctgggttttg atcatgggag tatggtggat ccagagcctc ataggtgtag aagaactgat  420
ggaaagaaat ggaggtgtgg taagaatgtg gtgcctaacc agaagtactg tgaaagacac  480
atgcatagag gtcgaaatcg ttcaagaaag cctgtggaaa catctcaaat taactctcat  540
ctggcaacaa agccatctag caagtcacac aacaaacccg cctcaaggac acaatttgaa  600
atttcaaatc caaaccttat ggccattcga catagtgaca catcaagtac cccatcaagg  660
agtctcagtg ttgccaattg ctcttctgct aataataggt ggaaaaatag tgcaagttat  720
gctgactacc tcacatcgtt ttcttctgcg tctgcagtgt cccctggatc cactcttgcc  780
actccagttg ctcctaagat ggccaccttc agcagtgtga catccattgc ttcagataga  840
ggaagttgcc taaatatatg ccagaaagat aacaagtcca agagctgtat cagcaacaac  900
atcagtgtta aaagtggtgg gaaaggaaga attgttggtg acactaatgg catttctact  960
ggaataggct tctccccaac gagtgttctt caagtttctg gttgcaaccc ttcatacctg  1020
aatgacagaa ccaacataga atctgcatcc ggtaggtgcc ggagaacaga tggtaagaag  1080
tggcaatgca agagtgctgt tcttccgggt cagaagtact gtgccacaca catgcacaga  1140
ggtgctaaaa agcggctcac aagccatgaa ccggcagtta ccattgcgcg gttgcctaac  1200
tcttcagtca caaccaaaat gcagaaagcg cattgtgcaa ttccaaacac aaatctttcc  1260
atgtcagtcc cagcaagtga accattcata caatgtaatg agaaaagtca aagtaccagt  1320
gacactgata ccaccatcag tgacaccttg aatgagtgta gctatgcttc tttctga     1377

SEQ ID NO: 99          moltype = DNA  length = 1008
FEATURE                Location/Qualifiers
source                 1..1008
                       mol_type = other DNA
                       organism = Glycine max
SEQUENCE: 99
atgagcgttc ctccgccgta tgcggcggcg atgtggacgc cgttcacggc ggcacagtgg  60
cacgagctgg agcaccaggc cctcatcttc aagtacctca aggcgggtct ctcggttccc  120
cctgacctcc ttctccccat tcgcaagagc ctccagttga tgtctcatcc atctctgggg  180
ttttatggga agaagataga ccctgaaccg ggtcggtgca ggagaaccga tgggaaaaag  240
tggaggtgtt cgagggatgc gcaccctgac tccaagtact gcgaccgcca tatgatacgg  300
cggcgttacc gttcaagaaa gcctgtggaa tcatctcaaa ctcactcttc ttcttcttct  360
tcttcttctt cttctgctac tgctgcttct tcaaattcaa atcctgttgc tggtggtggt  420
ggtggttctg ttgctaatgt ttctggaact gcaactgctg caaaaaccct tcacaccctt  480
cccttgcaca ccaatggtgc aagggaaggt ttcactttca cccttgggaa caacaccaac  540
```

```
accaccctcc cacaccttca catgaacccc ctcactcttt cagctgacaa taccaagaaa  600
acttacaggt ttggactgaa ctcagaagca gatgagcaca acgtcttaca gaaagatctg  660
ggaagtgtga ggtatcaagg ttatgacttt acctcagatg ccatgtggtc tcaaatgtct  720
cacattccat caaatactgt ttcggaatca agaagtggtt ctactatgct gggcaactgc  780
ttccaacatc aaacaatgcg agatgctgag ctgttgaacc tggaaacggc aaggaccaaa  840
gatcttgtct ttagtggcca gttaagttca gctgggggtt tgaaacagga atatcagtct  900
ccccagtctc tcttcagtga ctgggactgg aagaaggatt taagttcctc tgcccttgag  960
tataagccta acaaggattt taactgcaac ccagatgcca atgtttga              1008

SEQ ID NO: 100         moltype = DNA  length = 1155
FEATURE                Location/Qualifiers
source                 1..1155
                       mol_type = other DNA
                       organism = Glycine max
SEQUENCE: 100
atgaatggaa ggaacgttaa cacaaacagg ttccctttca ctccttccca gtggcaagag  60
cttgaacacc aagctctcat ctacaaatac atggcttcag gtatctccat ccccccctgac  120
cttctcttca ccatcaaaag aacaacccac ttggactcct caagactatt gcctcaccac  180
cctcaacact ttggatggaa ctatttgcca atggggttgg ggaggaaaat agacccggag  240
ccagggaggt gtagaagaac agatggaaag aaatggaggt gctcaaagga ggcgtatcca  300
gattcaaagt actgtgagag gcacatgcac agagggaaaa atcgttcaag aaagcctgtg  360
gaagttttga aacaacaccc aacgacagca gcagtggcaa caaacacaga tgcctcaacc  420
ccaacaacaa tcttatcaat caccaaaaac agtcctgcac atgcactctc cccaaccact  480
cattctctct ctcatgacac ttaccatcat catcatcatc accctcaccc tcagcaacat  540
tcctcccact ccttcctcta tcatcattct tcgaggccct cttccggtgc tgctttgtca  600
tttcaagaca acagtgcccc cttgtttctc gacactgctt cttgctctca gaataacaac  660
aacactgact gcaggaacag gtatgtgtat ggactgaagg aggaggtgga cgagcatgcc  720
ttcttcacag aaccttctgg aactatgaga agcttctctg cttcctcaat ggaagattca  780
tggcaactca caccactgac tataagctcc tcttcctctt cgaaacagag gaactgctct  840
ggtttatcca atgacaacaa cgagtactcc tacttgcaac ttcagagcct caatggcaac  900
aactcaaaac agccacaaca agatcaaggt tgctacatat caggcagtga tgtcaagtgc  960
gaaacattca tgaaacttgg gaaagaagaa cctcagaaaa ccgttcatcg cttcttcgat  1020
gaatggcccc ctaaaagcag aggatcgtgg cttgatttgg atgataaatc atccaccacc  1080
cagctttcaa tttccattcc aacttctact catgattttg caactttcaa ttcaacaacc  1140
caacgagatg gttga                                                   1155

SEQ ID NO: 101         moltype = DNA  length = 1098
FEATURE                Location/Qualifiers
source                 1..1098
                       mol_type = other DNA
                       organism = Glycine max
SEQUENCE: 101
atgatgaatg gaagaaacag gtttcccttt accccatcac agtggcaaga gcttgaacac  60
caagctctca tctacaagta catggcttca ggcatttcca ttccccctga tcttctcttc  120
accataaaaa ggagctattt tgattcccct ctctcctcaa ggcttttgcc taaccagcca  180
caacactttg gatggaacta ccttcagatg ggtttgggaa gaaaaataga ccctgagcca  240
ggtaggtgta gaagaactga tggcaagaaa tggagatgct caaaagaagc atacccagat  300
tctaagtact gtgagaggca catgcacaga gggaagaatc gttcaagaaa gcctgtggaa  360
gttttgaaaa caacaacacc atcatcaaca atgacaacaa caaacacaaa ctcaaatgct  420
tcttcaacac aacaagcaat ctcatcaatc accaaaaatta atactctttc acctcttgct  480
tcatctgaga ctcaccaaca ccaccctcaa cactatggct cctttctcta tcatcatcac  540
cctccttcaa ggtcctctgg cattggcttg tcctttgaag ataatagggc tcccttgttt  600
cttgacactg gctcttgctc tcagtccaac acagactgca ggagtaggta tgtttatgga  660
gagaaagagg aggtggatga gcatgctttc ttcacagaac cttgtggtgt tatgaaaagc  720
ttctctgctt cctctatgga tgactcatgg caactcacac cattgactat gagttcctca  780
tcttcttctt ccaaacagag gagttccttt ggcttgtcca gtgattactc ttgcttgcaa  840
cttcagagcc actcaaagca gcagcaacaa gagcatcatc aagatcaggg ttgctacatg  900
tttggtggtg gtcaagttgt gaaagaagaa cctcagaaaa cggttcatcg cttctttgat  960
gaatggcccc acaaaggaag agaagggtct tggcttgatt tggatgacaa atcttccaca  1020
acccaacttt caatttccat ccccacatgt tctcatgatt ttccaacttt cagttctaga  1080
aaccaccacg atggttga                                                1098

SEQ ID NO: 102         moltype = DNA  length = 1014
FEATURE                Location/Qualifiers
source                 1..1014
                       mol_type = other DNA
                       organism = Glycine max
SEQUENCE: 102
atgagcgttc ctccgccgtc tacggcggcg atgtggacgc cgttcacggc agcgcagtgg  60
cacgagctgg agcaccaggc cctcatcttc aagtacctca aggcgggtct ctcggttccc  120
cctgacctcc ttctccccat tcgcaagagc ctccaattga tatcgtctca cccatcgatg  180
gggtattatg ggaagaagat agaccctgaa ccgggtcggt gcaggagaac cgatgggaaa  240
aagtggaggt gttcgaggga tgcacaccct gactccaagt actgcgaccg ccatatgata  300
cgacgtcgtt accgttcaag aaagcctgtg gaatcatctc aaactcactc ttcttcttct  360
gcttctgctg cttcttcaaa ttcaaaccct gttgctgctg gtggtggtgg tggttctgtt  420
gctaatgttt ctgcaactgc tgcaaaaaac cttcacacac ttcccttgca catcaatggc  480
gcaagggaag gtttcacttt caccccttggg aacaacacca gcaccaacac caacaccaac  540
accaacaccc tccctcacct tcacatgaac cccctcactc tttcagctga caataccaag  600
aaaacttaca ggtttggact gaactcagaa gcagatgagc acaacgtctt acagaaagat  660
```

```
ctgggaagtg tgaggtatca aggttatgac tttacctcag atgccatgtg gtctcaaatg  720
tctcacattc catcaaatac tgtttcggaa tcgagaatcg gttctactat gctgggcaac  780
tgcttccagc atcaaacaat gcgagatgct gagctgttga atctggaaac ggcgaggacc  840
aaagaccttg tctttagtgg ccagctaagt tctgcagggg gtatgaaaca ggaatatcag  900
tctccccagt ctctcttcag tgactgggac tggaagaagg atttaagttc ctctgccctt  960
gagtataggc ccaacaagga ttttaactgc aacccagatg tcaatgttga ttaa        1014

SEQ ID NO: 103         moltype = DNA  length = 1803
FEATURE                Location/Qualifiers
source                 1..1803
                       mol_type = other DNA
                       organism = Glycine max
SEQUENCE: 103
atggatcttg ggtggtgggg tttggagggg gtggtgggtt cagaaagtgg ttgtgtgttt  60
ggttcttctc ttgtttcaga tcctgagaca aagcacaagt ggtacggatc tggtttgctc  120
aagcaagaga gatctgccat agctactgaa gatgatgagt ggagaatttc caaagttgct  180
aaaactgatc atgacatgtc ttcagcctcc aaagcaatgc tctttcagca aagaaacaac  240
tctttgttga gatctaataa tgcaactctc ttctctgatg gtcatcacca atcacaaatg  300
ttgagcttct cttctccaaa gtcagattct ttgttgatag ataaggcttc ctcaaatgcc  360
acattgcctt tttcttccca ccaattgtct agctacacca gaaatacagg ttacaattca  420
ggaagcataa gcatgcatgg ggctttggct agtgtgagag ggccattcac tccatcacag  480
tggatggagc ttgaacacca agccttgatc tacaagtaca tcacagcaaa tgttcctgtg  540
ccaactcatc ttctcattcc catcagaaaa gcacttgatt ctgttggctt ctgcaacttc  600
tcagccggac tcctcagacc caactcattg ggatggggag gtttccatct aggattctcg  660
aacaatacag accctgagcc agggaggtgt aggagaacag atggaaagaa atggcgatgt  720
tcaagagatg ccgtagtaga tcagaagtat tgcgagcggc acatgaaccg aggacgccat  780
cgttcaagaa agcctgtgga aggccaatca ggccatgccc tcaccaccac caccagtaat  840
acacctaatg cttcctccaa ctctgtggtg cctggcaaca acaacaacac ctttgcacac  900
aacaatgtgc accaccctat tcctcctcat tcctctccgg tcaacaccat cactaggatg  960
tttacaagca acaaagagaa taataacagt accagtgaga ggatgcagga ccctgcactt  1020
cccatgcttc ctcccactct tgagctgaaa ccaaaggaga acaatccttt catgattcat  1080
aaacaccaaa tcccatctga tgaatactca agtaggaaca acaatgagtt tgggcttgtc  1140
acttctgatt ctttgcttaa cccctcagag aaaagaagct ttacttcttc acaaaagaat  1200
gattcttctg agtcccaaca acaacattcc ctcaggcact tcattgatga ctctcccaaa  1260
ccacagtcta atcatcatca tcgttcgtcg tctatatggc ctgaacttga caacatgcag  1320
tcagacagga ctcagttatc aatctccata ccaatatctt cctcagatca cttcatgtca  1380
ttcactactt ccttgccctc gaacgagaaa ctcacgttgt caccacttag gctttcaagg  1440
gagttagacc ccattcaaat ggggttggga gtgggaagtg cccccaatga agcaaacact  1500
aggcaagcca attggattcc aatcacttgg gagagttcaa tgggtggtcc tcttggagag  1560
gttttgaacc ttagtaacaa taacaacagc aatgctagtg atcaatgtgg caagaacaac  1620
aacaacactt cagctctcaa cctcatgaaa gatggatggg acaataatcc tccatcaggg  1680
tcatccccaa ctggggtgct tcaaaaatct gcatttggat cactttccaa tagcagtgct  1740
gggagcagtc caagggggc agagaacaac aaagaaggtg ccaccttgtg caatgccttg  1800
taa                                                                1803

SEQ ID NO: 104         moltype = DNA  length = 1134
FEATURE                Location/Qualifiers
source                 1..1134
                       mol_type = other DNA
                       organism = Glycine max
SEQUENCE: 104
atgatgaatg gaaggaacgt tgacacaaac aggttcccct tcactccttc ccagtggcaa  60
gagcttgaac accaagccct catctacaaa tacatggctt caggtatttc catcccccct  120
gaccttctct tcaccatcaa aagaacaacc cacttggact cctcaagact cttgcctcaa  180
cactttgggt ggaattattt gccaatggga ttggggagaa aaatagaccc agagccaggg  240
aggtgtagaa gaacagatgg gaaaaaatgg aggtgctcaa aggaggcgta tccagattca  300
aagtactgtg agaggcacat gcacagaggg aaaaaccgtt caagaaagcc tgtggaagtt  360
ttgaaaacaa caccaatgac agcagcaaca aacacagatg cctcaacccc aacaacaatc  420
ttatcaatca ccaaaaacag tcctgtactc ttcccaacca ctcattctct gtctcatgac  480
acttaccatc atcatcacca tcatcactct caccctcagc aacattcctc ccactccttc  540
ctctatcatt cttcgaggcc ctcttccggt ggtgtttctt tgtcatttca agacaacagt  600
gccccttgt ttctcgacac tgcttcatgc tctcagaata acaacaacac tgactgcagg  660
tatgtgtatg gactaaaaga ggaggtggat gagcatgcct ttttcacaga accttctgga  720
actatgagaa gcttctctgc ttcctcaatg gaagattcat ggcaactcac accactgact  780
ataagctcct cttcctcttc aaaacagagg agttgctctg gtttatccaa tgacagcaat  840
gagtactcct acttgcaact tcagagcctc agtggcaaca actcaaagca tccacagcaa  900
gatcaaggtt gctacatatc aggcagtgat atcaagtgcg aaacattcat gaaacttggg  960
aaagaagaac ctcagaaaac cgttcatcgc ttcttcgatg aatggcctcc caaaagcaga  1020
ggatcatggc ttgatttgga tgataaatca tccacaaccc agctttcaat ttccattccc  1080
acttctactc atgattttgc aactttcagt tcaacaaccc aacgagatgg ttga        1134

SEQ ID NO: 105         moltype = DNA  length = 1830
FEATURE                Location/Qualifiers
source                 1..1830
                       mol_type = other DNA
                       organism = Glycine max
SEQUENCE: 105
atggatcttg ggtggtgggg tttggagggg gtggtgggtt cagaaagtgg ttgtgtgttt  60
ggttcttctc ttgcttcaga tcctgagaca aagcacaagt ggtacggatc tggtttgctc  120
```

```
aagcaagaga gatctgccat agctactgaa gatgatgagt ggagaatttc caaagttgct  180
aaaactgatc atgacatgtc ttcagcctcc aaagcaatgt tctttcagca aagaaacaac  240
tctttgttga gatctaataa tgcaactctt ttctctgatg gtcatcacca atcacaaatg  300
ttgaacttct cttctccaaa gtcagagact ttattggtag ataaggcttt ctcaaatgcc  360
acattgcctt tttcttatca tcaattgtct agttacagca gaaatacagg ttacaattcg  420
ggaagcataa gcatgcatgg ggctttggct agtgtgagag ggccattcac tccatcacag  480
tggatggagc ttgaacacca agccttgatc tacaagtaca tcacagcaaa tgttcctgtg  540
ccaactcatc ttctcattcc catcagaaaa gcacttgatt ccgttggctt ctgcaacttc  600
tcatctggac tcctcagatc caactcgttg ggatggggag gcttccattt gggattctcc  660
aacagcacag accctgagcc agggaggtgt aggagaacag atgggaaaaa atggcgatgc  720
tcaagagatg ctgtagtaga tcagaagtat tgcgaacggc acatgaaccg aggacgccat  780
cgttcaagaa agcctgtgga aggccaatca ggccatgccc tcaccaccac taacacacct  840
aatgcttcct caaactcaac cgtggtgccc ggcaaccaca acaacaacac ctttgcacac  900
atcaatgtgc accaccctct tcctcctcat tcctctccag ccaataccat caataggatg  960
tttatgagta ataataaaga gaacaacaac acgagtgaga ggatgaagga tggccttgcc  1020
cttcccatgc tacctcctac tcttgagctg aaaccaaagg acaacaacaa ctctttcatg  1080
gttcataaac accaagaacc atatgatgaa tcctcaagga acaagaatga gtttggactc  1140
gtcacttctg attccttgct taacccttca cagaaaagaa gctttgattc ttcttcttct  1200
tcttcacaaa aggatgattc ttctgagtcc caacaacaac attccctcag gcacttcatt  1260
gatgactctc ccaaaccaca gtctcatcat aatcataacc atcgttcgtc gtcatctatt  1320
tggcctgaac tcgacaacat gcagtcagac aggactcagt tatcaatctc cataccaata  1380
tcttcctcag atcacttcat gtcatttgca acttcctcgc cctcgaatga aaaactcaca  1440
ttgtcgccac taaggctttc gagggagttc gaccccattc aaatgggatt aggagtggga  1500
agtgcctcca atgaagcaaa cactaggcaa gccaattgga ttccaatcac ttgggagagt  1560
tcaatgggtg gtcctcttgg agaggttttg aaccttagta acaataataa taacagcaat  1620
gcaagtgatc aatgtggcaa gaacaacaac aacacttcag ctctcaacct catgaaagat  1680
gatgacgatg atgatgggtg ggacaatagt cctcctccaa tagggtcatc accaactggg  1740
gtgcttcaaa aaacagcatt tggatcactt tccaacagca gtgctgggag cagtccaaga  1800
ggggcaccag agaacaacaa caaagaatag                                  1830

SEQ ID NO: 106          moltype = DNA  length = 1800
FEATURE                 Location/Qualifiers
source                  1..1800
                        mol_type = other DNA
                        organism = Glycine max
SEQUENCE: 106
atggatcttg ggtggtgggg tttggagggg gtggtgggtt cagaaagttg ttgtgtgttt  60
ggttcctctc ttgcttcaga tcctgagaca aagcacaaat ggtacggatc tggtgtgctc  120
aagcaagaga gatctgccat agcaagtgaa gatgatgagt ggagaacttc taaagtggcc  180
aaaactgatc atgacatgtc ttctgcctcc aaagcaatgc tctttcagca aagaaacaac  240
tctttgttga gatctaatgc taccctttttc tctgatggcc atcatcacca atcacaaatg  300
ttgagcttct cttctccaaa gtcagagtct ttgttggtag ataaggcttc ctcaaatgcc  360
acattgcctt tttcttacca ccaattgtct agcaacacca gaaatgcagg ttacagttca  420
ggaagcataa gcatgcatgg ggctttggct ggtgtgagag ggccattcac tccgtcacag  480
tggatggagc ttgaacacca agccttgatc tacaaataca tcacttcaaa cgtgcctgtg  540
ccaacccatc tcatacccat tagaaaagca cttgattctt tgggcttctg caacttttca  600
actggactcc taaggcccaa cgcattggga tggggaggtt tccatctggg attctcgaac  660
aacacagacc ctgagccagg caggtgtagg agaacagatg gaaaaaaatg gcgatgctcg  720
agagatgccg tagtggatca aaagtattgc gagcggcaca tgaatagagg acgccatcgt  780
tcaagaaagc ctgtggaagg ccaattaggc catgccctca ccaccaccac caccaccaat  840
acacctaatg cttcctccaa ctctaccgtg gtgccccgca acaccaccac caccaccacc  900
tttgcacaca acaatgtgca ccaccctctt ccacctcatt cgtctcaggc caacaccatc  960
aataggatgt ttacaagcaa caaagagaat aacagtacca gtgagaggct gcaggaccct  1020
gctcttccca tgctgcctcc cactcttgag ctgaaaccaa aggagaacaa tcctttcatg  1080
attcataaac accacatccc agctgatgaa tactcaagga acagcaatga gtttggactc  1140
gtcacttctg attccttgct taaccctaca cagaaaagaa gctttacttc ttcacaaaag  1200
gatgattctg agtcccaaca acaacattcc ctcaggcact tcattgatga ctctcccaaa  1260
ccacagtctc ataatcatca ccaccatcat cattcgtcgt ctatttggcc cgaactggac  1320
agcatgcaat cagacaggac tcagttatca atctccatac cgatatcttc ctcagatttt  1380
atgtcattca ctacttcctc accctccaac gagaaactca cgttgtcacc attggggcat  1440
tcgagggagt tagaccccat tcaaatggag ttgggaatgg gaagtggtgc ctccaatgaa  1500
gcaaacacca ggcaagccaa ttggattcca atcacttggg agagttcaat gggtggtcct  1560
cttggagagg tattgaacct tagcaataac agcaatgcaa gtgatcaatg tggcaagaac  1620
aacaacactt cagctctcaa cctcatgaaa gatgggtggg acaataatcc tccactaggg  1680
tcatccccaa ctggggtgct tcaaaaatca gcatttggat cactttccaa tagcagtgct  1740
gggagcagtc caagggcaga aaacaacaaa gaaggtgcca ccttgtgcaa tgccttgtaa  1800

SEQ ID NO: 107          moltype = DNA  length = 1785
FEATURE                 Location/Qualifiers
source                  1..1785
                        mol_type = other DNA
                        organism = Glycine max
SEQUENCE: 107
atggatcttg ggtagtgggg tttggagggg gtggtgggtt cagaaagtgg ttgcgtgttt  60
ggttcctctc ttgcttcaga tcctgagaca aagcacaagt ggtacggatc tggtgtgctc  120
aagcaagaga gatctgccat agcaagtgaa gatgatgagt ggggaactta taaagtggcc  180
aaaattgatc atgacatgtc ttctgcccct aaagcaatga tctttcagca aagaaacaac  240
tctttgttga gatctaataa tgctactctt ttttctgacg gccatcacca atctcaaatg  300
ttgagtttct cttctccaaa gtcagagact ttgttggtag atacagcttc ctcaaatgcc  360
```

```
acattgcctt tttcttacca tcaattgtct agttacagca gaaatacagg ttacagttca  420
ggaagcataa gcatgcatgg ggctttggct ggtgtgagag ggccattcac tccatcacag  480
tggatggagc ttgaacacca agccttgatc tacaaataca tcactgcaaa catgcctgtg  540
ccaactcatc ttctcatacc catcagaaaa gcacttgatt ctgttggctt ctgcaacttc  600
tcaactggac tcctcagatc caactcattg ggatggggag gtttccatct gggattctcg  660
aacagcacgg accctgagcc agggaggtgc aggagaacag atggaaagaa atggcgatgc  720
tcaagagatg ccgtagtaga tcagaagtat tgtgagcggc acatgaacag aggacgccat  780
cgttcaagaa agcctgtgga aggccaatca ggccatgccc tcaccaccac caccaccact  840
actaacacac ttaatgcttc ctcaaactca accgtggtgc ccggcaacaa cacctttgca  900
cacaacaaag tgcaccaccc tcttccacct aattcctctc cagccaatac catcaatagg  960
atgtttatga ataataaaga gaataacagc acgagtgaga ggatggagga ttgctctgcc  1020
cttcccatgc tacctcccac tcttgagctg aaaccgaagg agaaaaacaa tttcatgatt  1080
cataaacacc aagaccccta tgatgaatcc tcaaggaaca acaatgagtt tggactcgtc  1140
acttctgatt ccttgcttaa ccctacacag aaaagaagct ttgattcttc ttcttcacaa  1200
aaggatgatt ctgagtccca acaacaacat tccctcaggc acttcattga tgactctccc  1260
aaaccaccat ctcataatca tcatcgttcg tcgtccattt ggcccgaact cgacaacata  1320
cagtcagata ggactcagtt atcaatctcc ataccaatat cttcctcaga cttcatgtca  1380
ttcactactt cctcaccctc caacgagaaa ctcacgttgt cgccacttag gctttcgagg  1440
gcgttagacc ccattcaaat ggggttggga gtgggaagcg gtgcctccaa tgaagcaaat  1500
cctaggcaag ccaattggat tccaatcact tgggagagtt caatgggtgg ccctcttgga  1560
gaggttttga accttagcaa taacagcaat gcaagtgatc aatgtggcaa gaacaacact  1620
tcagctctca acctcatgaa agatgatgat gatgatgggt gggacaatag tcctccacta  1680
gggtcatcac caactggggt gttgcaaaaa acagcatttg gatcactctc caacagcagt  1740
gctgggagca gtccaagggg ggcaccagag aacaacaaag aatag                 1785

SEQ ID NO: 108          moltype = DNA  length = 1002
FEATURE                 Location/Qualifiers
source                  1..1002
                        mol_type = other DNA
                        organism = Glycine max
SEQUENCE: 108
atgaacatca gtggcggagg aggaactgtg atgggtttca gtagtaatgg gaggtcccca  60
ttcacagtgt ctcagtggca ggaactggag caccaagctt tgattttcaa gtacatggtt  120
gcgggtcttc ctgtgcctcc cgatctcgtc ctccccattc agaagagctt cgactctact  180
ctctctcacg ctttctttca ccatcccaca ctgagttatt gttccttcta tgggaagaag  240
gtggaccctg agccaggacg atgcaggagg actgatggaa aaaagtggag gtgctccaag  300
gaagcatacc cagactccaa gtactgcgag cgccacatgc accgtggccg caaccgttca  360
agaaagcctg tggaatcaca aactatgact cactcgtctt caactgtcac atcactcact  420
gtgactggtg gtggtgacag taatggaact gtaaacttcc aaaaccttcc cacaaatgcc  480
tttggtaatc tccagggtac tgattctgga actgaccgca cgaattatca tctagattcc  540
attccctatg cgattccaag taaagaatac aggtgtcttc aaggacttaa atctgagggt  600
ggtgaacact gcttcttttc tgaagcttct ggaagcaaca aggttctcca aatggagtca  660
cagctggaaa acacatggcc ttcgatgtca accagagttg cctctttttc tacatcaaaa  720
tcaagtactg attccctgtt gcatagtgat tatccccaac attcgttttt atctggtgaa  780
tatgcatcgg gagaacacgt gaaggaggag ggccagcctc ttcgaccttt ttctaatgaa  840
tggcctaaaa gcagggagtc atggtctggt ctggaagatg atatatccaa ccaaacagcc  900
ttctccacaa ctcaactctc aatatccatt cctatgtctt ccgatttctc tgcaacgagc  960
tctcagtccc cacatggtga gaatgagatt caatttaggt aa                    1002

SEQ ID NO: 109          moltype = DNA  length = 1737
FEATURE                 Location/Qualifiers
source                  1..1737
                        mol_type = other DNA
                        organism = Glycine max
SEQUENCE: 109
atgggtgaat tatttggcgt tggaaaaaga aggaacatca gcagcagcaa caacaacaac  60
aacagttcta gtagtagcgt tcttgggttg gatgtgaagg tgcaacagag ccctgaagca  120
ttattccata ataggatgat gatgatggcg catcataatc atcaccaccg tccattgtca  180
tcacccttg ataataatgg tgatggcgat ggtcccacga cttacatgtc ttttactaat  240
catataaacc ttgttagtgg tgcttcttct gttcttggtc ctgctattga tgctggctgt  300
ggtgctgctc ctcctgcacc tgtaagaact ttgcagcctt ttgacatttc ttcttatact  360
tcttctccca ccaccactac cacaaccttc aacttcaaac ccccttcagc aggtgtgatg  420
gcggcttcgt tggggtttcc tttcacaagt gcacaatgga gggagcttga aagacaagct  480
atgatataca agtacatgat ggcttctgtt cctgttccac atgatctcct cacaccctct  540
tctcgctctt cctgcatgga tggtggtttc aatctgaggt tggcaaatag cactgaccct  600
gagccaggta ggtgtagaag aacagatggt aaaaaatgga gatgttcaag agatgtggct  660
cctaaccaca agtactgtga gcgccatatg catagaggcc gtccccgttc aagaaagcct  720
gtggaagtta acaccaacag caccaccact cccactagcg tcaacaataa caaccatcaa  780
atcaaaaagg ctcgccatga gtgtaataat aatccttttg ctacacctga cgttactgcg  840
gctatttcca accccacatc cagaaaaaat ggatcttctc cccattttct tgggtctact  900
accactcagc cataccttga ttcttccctc tcccttgata actttggtct aaaagctgct  960
agttttgact ccgtggcttc tgtttctgct aataaggaac ccaggggttt agagtggatg  1020
ctgaatggag atcctatttc cctgggtgct tctgactcac aatggcagtc tctgatgcac  1080
aataaagatg gaatgaccag tgttagttcc tgtaacacca ccgagtctca gtatctgaat  1140
tcattagcac tatataactc tggactagaa caacagaata gacgccatcc tttgttcctg  1200
aaccctcttg ttgttcccat ggaaaatctc caaccggaga aaccaagggg ttttattgat  1260
gcttggtcta acgctgaaag caatgccaac accaacacca ccaacaagaa ctctgctgca  1320
tcaattggta aattatccct ttcttctctt gatctatcaa tggggggtgc tgctgtgaat  1380
gaagatgtgg gtaatgttaa catgggtttg ggcctaatgg agcctaatgg aaaaacgcac  1440
```

```
actggtacta aaatttctct ctccaattgg caaaacccag caccttgggt ggcttcatca  1500
cttgggggtc cactagctga agttctaagg tcaagcacag tcactgccac caccaccacc  1560
aatgaagcaa cctccaacac accctcgcca gccaccacta cacatgctga atctccatct  1620
ggggtgttgc agaaaacgct tgtttcattg tctgatagca gtaacaatag cagcccaagg  1680
gttgcatcat caagggccaa ttctgagatg gccttgctaa ggtttcaatc aaattaa     1737

SEQ ID NO: 110          moltype = DNA  length = 927
FEATURE                 Location/Qualifiers
source                  1..927
                        mol_type = other DNA
                        organism = Glycine max
SEQUENCE: 110
atgagtaagt ggcctttcac aatatctcag tggcaggaac tggaacatca agctttaatt  60
tacaaataca tggtggctgg tcttcctgtg cctcctgatc tagtcattcc cattcagaac  120
agcttccact ccatttccca aaccttcttg caccatccct ctaccaccat gagttattgt  180
tccttctatg ggaagaaggt ggacccggag ccaggacgat gcaggaggac tgatgggaaa  240
aagtggaggt gctccaagga agcctaccca gactccaagt actgtgagcg acacatgcac  300
cgtggccgca accgttcaag aaagcctgtg gaatcacaaa ctatgacaca gtcatcatcc  360
aatgtgtcat cattgactgt aactgctggc agcagcacca gtgcaactgg aaatttccag  420
aacctttcca ccacaaatgc atatggtaat ccccaaggga ctgcttctgg aacagaccaa  480
acccactatc acatggattc cattccctat gggatcccaa gtaaagaata caggtatttt  540
caaggatcta aatctgagga acatagtttc ttgtccaaaa ctttaggaag caacagggtt  600
ctacacatgg agccacagat ggacaacact ttgatgccaa ccggtggagt tgcctcattc  660
tctacattga gatcaaataa taattccatg ttgcagggtg attatctgca gccttctttc  720
ttatctagtg aatatgcctc ggcagaaact gtgaagcaag agggtcagtc ccttcgaccg  780
ttctttgatg aatggcctaa aagcagggac tcatggtctg gtctggaaga tgagagatcc  840
aatcacactc aactctcaat atccattcct atgtcatcgt caaatttctc tgcaactagc  900
tctcattccc cacatggtga gatttaa                                     927

SEQ ID NO: 111          moltype = DNA  length = 1008
FEATURE                 Location/Qualifiers
source                  1..1008
                        mol_type = other DNA
                        organism = Glycine max
SEQUENCE: 111
atggacttgc agttgaagca atggagtaac cggcatgagt cagaacaaga acattattcc  60
ccaaacatgc caaaatttct ccctcaacac cacccaccac catctccctc tgcactccct  120
ctctttgtac ctgaacaacc caacaccaaa gtctgcaccc tgtcagcatt ttctgattcc  180
acactacctt ctgctcccag attttccagg atggagagtt gcttcagctt tgcacagtgg  240
caagagcttg agttgcaggc tctgatattc aggtacatgc tggccggtgc tcctgttcct  300
cctgagctcc ttctaccaat caagaaaagc ttccttcaac tttataaccc tcctttgttg  360
gaatcagggt actactgggg aagagcagcg ctggatccgg agccggggcg gtgccggagg  420
accgacggca agaagtggcg gtgctcgaag gacgcggtgg cgggtcagaa gtactgcgac  480
cgccacatgc atcgtggccg aaaccgttca agaaagcctg tggaacaacg tgatggatct  540
ctttctgcta tagcctccgt ttcttcttca ccctcttctt catttaatct ccttcacctc  600
agtgaaagtt cctctggggc caagagtgac aacaagagct tctttgaaaa ccatgatcat  660
gtggatgggg atggaaattc agccaaatct gatggccatg tcttgaggca tttctttgat  720
gattggccaa ggacactgca agagcctgac aatggtgaaa gcaatggttg ccagaacaac  780
aactcaggaa catgtctttc tatgtcaaca ccaggaatca cttcctcgga tgtgtcgttg  840
aaattgtcca ctggccatgg agaggatgcg tgccacgcgg cctcaatggg aggaccactt  900
gcagaggcat taagatcatc caccaccagc tccacttctt caccaaccag tgttctgctt  960
cagttgcctc ctagttctgc ttctgaggct agtttcatta gcacctaa              1008

SEQ ID NO: 112          moltype = DNA  length = 1026
FEATURE                 Location/Qualifiers
source                  1..1026
                        mol_type = other DNA
                        organism = Glycine max
SEQUENCE: 112
atgaacaaca gcagtggcgg aggaggacga ggaactttga tgggtttgag taatgggtat  60
tgtgggaggt cgccattcac agtgtctcag tggcaggaac tggagcacca agctttgatc  120
ttcaagtaca tgcttgcggg tcttcctgtt cctctcgatc tcgtgttccc cattcagaac  180
agcttccact ctactatctc gctctcgcac gctttctttc accatcccac gttgagttac  240
tgttccttct atgggaagaa ggtggaccct gagccaggac gatgcaggag gactgatgga  300
aaaaagtgga ggtgctccaa ggaagcatac ccagactcca agtactgcga gcgccacatg  360
caccgtggcc gcaaccgttc aagaaagcct gtggaatcac aaactatgac tcactcatct  420
tcaactgtca catcactcac tgtcactggg ggtagtggtg ccagcaaagg aactgtaaat  480
ttccaaaacc tttctacaaa tacctttggt aatctccagg gtaccgattc tggaactgac  540
cacaccaatt atcatctaga ttccattccc tatgcgattc caagtaaaga atacaggtat  600
gttcaaggac ttaaatctga gggtggtgag cactgctttt tttctgaagc ttctggaagc  660
aacaaggttc tccaaatgga gtcacagctg gaaaacacat ggcctttgat gtcaaccaga  720
gttgcctctt tttctacgtc aaaatcaagt aatgattccc tgttgcatag tgattatccc  780
cggcattcgt ttttatctgg tgaatatgtg tcgggagaac acgtaaagga ggagggccag  840
cctcttcgac cttttttttaa tgaatggcct aaaagcaggg agtcatggtc tggtctagaa  900
gatgagagat ccaaccaaac agccttctcc acaactcaac tctcaatatc cattcctatg  960
tcttccaatt tctctgcaac gagctctcag tccccacatg gtgaagatga gattcaattt  1020
aggtaa                                                            1026

SEQ ID NO: 113          moltype = DNA  length = 1155
```

```
FEATURE                Location/Qualifiers
source                 1..1155
                       mol_type = other DNA
                       organism = Glycine max
SEQUENCE: 113
atggacttcc atctgaagca atggagaaac cagcacgagt cagaggaaca acattctaca  60
aagatgccaa aacttctccc tgaatcccat caacaacaac agccatcagc ctctgcactc  120
cctttgtttg tacctgaacc caacagcagc aaagtcagca ccctgtcaga ttcaacatta  180
gcttctgcta caatgacttc taccaccact aacagattat ttcccaggat ggggagctac  240
ttcagcttgt ctcagtggca ggagcttgag ttgcaggctt tgatattcag gtacatgttg  300
gctggtgctg ctgttcctcc tgaactcctt caaccaatca agaaaagcct tcttcattct  360
ccacactatt acctccatca ccctctccaa cattaccaac cttctgcttt gttgcaatca  420
gggtattggg gtagaggagc gatggatccg gagccagggc ggtgccggag aaccgacggc  480
aagaagtggc gctgttcgag ggacgtggtg gctgggcaaa agtactgtga gcgccacatg  540
caccgtggaa gaaaccgttc aagaaagcct gtggaactac ccacaccaac tagtgctatt  600
aacaattgtg gtgtaactgg agttggatcc ctaggaccag gtgcttcatc atcttccatt  660
tgttcaccac ccttagcttc tgcttcattc aaatctcctt ttgatcttca tcttgatgaa  720
cgttcctctg ggaccaagaa tgaagacgaa gatcatgtgg gtggggatgg cagatcaggt  780
ggaggtggtg gccatatgct gaggcatttc ttcgatgatt ggccacgatc actccaagac  840
tctgacaacg ttgaaaacaa tgctgctgct ggccgtagcc tctctatttc aatgcccggt  900
gcttcctcgg atgtgtcatt gaaattgtcc acgggctatg gagaggactc gggcccagga  960
aatgagaatg taagcctcga gccagagcag ctgcagttga attgggccgg aggatgggcc  1020
tcgtctaatc aagtggcttc gatgggaggt ccacttgctg aggcactcag atcatctact  1080
tcaacctcat ctcccactag tgttttgcat cgtcacttgc ctcgtggatc tgagaccagc  1140
tttattagca cctga                                                   1155

SEQ ID NO: 114         moltype = DNA  length = 1407
FEATURE                Location/Qualifiers
source                 1..1407
                       mol_type = other DNA
                       organism = Glycine max
SEQUENCE: 114
atggaagcta agcctcttcg aactgttccc tcttcacaca acacttctgg ggtaggaggt  60
ggaccccaga agaagattgg catggaacac aagatggaaa gtcgtgttgt tgatgagagg  120
aagagggttg ttatggtcaa ggaagagaac agcacttctt ctcccaacag tgttgaactt  180
catctcgggt ttgatgcttc tcattcgact ccacaagaaa taaaccatgt gatcactgaa  240
gctcagaggc gtgagcttca ccatcaagtt ttcatcttca accatttggc ttataatctt  300
cctcctcctt atcaccttgt gcaattccct agcaacatgt cagaatacag tttcctgggt  360
tttgatcatg ggattatggt ggatccagaa cctcataggt gtagaagaac tgatggaaag  420
aaatggaggt gtggtaagaa tgtggtgcct aaccagaagt actgtgaaag gcacatgcac  480
agaggtcgaa atcgttcaag aaagcctgtg gaaacatctc aagttaactc tcctttggca  540
acaaagcctt gtagcaagtc acacaccaaa ccatcctcaa agacacaatt tgaaatttca  600
agtccaaacc ttatcgccat tccacatatt gacacatcaa gtaccccatc aaggagcctc  660
agtgtcacca attgctcttc tgctaataat aggtcgaaaa atagggcagg ttatgctgac  720
tacctcatgt cgttttcttc cgcgtccaca gtgtcccctg gaaccactct tgccactcca  780
gttgccccta agatagctgc cttcagcagt gcgacatccg ttgttgcttc agatagcaaa  840
agttgcctaa agatatgcca gaaagataac cagtccaaga gctgtatcag caacaacatc  900
ggtgttaaaa gcggtgggaa aggaagcatt gttggtgata ctaatactaa tggcatctct  960
actggaataa gcttctcccc aacgagtgtt cttcaagttt cagtttctgg ttgcaaccct  1020
tcatacctga atgacggaac caacatagaa gctgcatccg gtaggtgccg gagaacagat  1080
ggtaagaagt ggcagtgcaa gagtgctgtt cttcctggtc agaaatactg tgccacacac  1140
atgcatagag gtgccaaaaa gcgtctcaca agccatgaac cagcagctac tgctaccagt  1200
tccgccgtta ccgttgcgcg gttgccttac tcttcagcca ctaccaacat acagaaagcg  1260
cattgtgcaa ttccaaacac aaatctttcc atgtcagtcc aagccaggga agcattcata  1320
caatgtaatg agaaaagtca aagtagcagt gacactgata ctactatcag tgacaccttg  1380
aatgagtata gctatgcttc tttctga                                      1407

SEQ ID NO: 115         moltype = DNA  length = 1083
FEATURE                Location/Qualifiers
source                 1..1083
                       mol_type = other DNA
                       organism = Glycine max
SEQUENCE: 115
atgatgagtg caagtgcagg tgcaagaaat aggtctccgt tcacacaaat tcagtggcaa  60
gagcttgagc aacaagctct tgtttttaag tacatggtta caggaacacc tatcccacca  120
gatctcatct actctattaa aagaagtcta gacacttcaa tttcttcaag gctcttccca  180
catcatccaa ttgggtgggg atgttttgaa atgggatttg gcagaaaagt agacccagag  240
ccagggaggt gcagaagaac agatggcaag aaatggagat gttcaaagga ggcatatcca  300
gactcaaagt actgtgaaag acacatgcac agaggcagaa accgttcaag aaagcctgtg  360
gaagtttctt cagcaacaag caccgccaca aacacctccc aaacaatccc atcatcttat  420
accagaaacc tttccttgac caataacagt aaccccaaca taacaccacc accaccaccc  480
tcttctttcc ctttctctca tttgccctct tctatgccta ttgatcagtc ccaacccttt  540
tcccaatcct accaaaactc ttctctcaat cccttcttct actcccaatc aacctcctct  600
agacccccag atgctgattt tccaccccaa gatgccacca cccaccacct attcatggac  660
tctgctggct cttattctca tgatgaaaag aattatagca ggcatgttca tggaataagg  720
gaagatgtgg atgagagagc tttcttccca gaagcatcag gatcagctag gagctataca  780
gactcgtacc aacaactatc aatgagctcc tacaagtcct attcaaactc caactttcag  840
aacattaata atgatgccac caccaaccca agacagcaag agcagcaact acaacaacaa  900
caacactgtt ttgttttagg gacagacttc aaatcaacaa ggccaagcaa agagaaagaa  960
```

```
gctgagacaa caacaggtca gagacccctt caccgtttct ttggggagtg gccaccaaag  1020
aacacaacaa cagattcctg gctagatctt gcttccaact ccagaatcca aaccgatgaa  1080
tga                                                                1083

SEQ ID NO: 116          moltype = DNA  length = 1098
FEATURE                 Location/Qualifiers
source                  1..1098
                        mol_type = other DNA
                        organism = Glycine max
SEQUENCE: 116
atgatgaatg gaaggaacag gttccccttt accccatcac agtggcaaga gcttgaacac  60
caagctctca tctacaagta catggcttca ggcatttcca ttccacctga tcttctcttc  120
accataaaaa ggagctattt tgattcccct ctgtcctcaa ggcttttgcc taaccagcca  180
cagcactttg gatggaacta ccttcagatg ggtttgggaa gaaaaataga ccctgagcca  240
ggtaggtgta gaagaactga tggcaagaaa tggagatgct ccaaagaagc atacccagat  300
tcaaagtact gtgagaggca catgcacaga gggaagaatc gttcaagaaa gcctgtggaa  360
gttttaaaat caacaacaac accatcatca tcaacaacaa actcaaatgc ttcttctaca  420
caacaagcaa tctcatcaat caccaaaatt aatagcactc tctcacctct tgcatcatct  480
gagactcacc aacaccacca ctatcctcaa cactatggct cctttctcta tcatcatcac  540
cctccttcaa ggtcctctgg cattggcttg tcttttgaag acaacagtgc tcccttgttt  600
cttgacactg gctcatgctc tcagtccaac acagactgca ggagtaggta tgtttatgga  660
gagaaagagg aggtggatga gcatgctttc ttcacagaac cttgtggtgt tatgaaaagc  720
ttctctgctt cctctatgga tgactcatgg caactcacac cattgactat gagctcctca  780
tcttcatctt ccaagcagag gagttccttt ggcttgtcca gtgattactc ttgcttgcaa  840
cttcagagcc actcaaagca gcagcagcaa gagcatcatc aagatcaggg ttgctacatg  900
tttggtgctg gtcaagttgt gaaagaagaa cctcagaaaa cggttcatcg cttctttgat  960
gaatggccac acaaaggaag agaaggctct tggcttgatt tggatgacaa atcttccaca  1020
acccaacttt caatttccat ccccacatct tctcatgatt tttcaacttt cagttccaga  1080
acccaccatg atggttga                                                1098

SEQ ID NO: 117          moltype = DNA  length = 1038
FEATURE                 Location/Qualifiers
source                  1..1038
                        mol_type = other DNA
                        organism = Glycine max
SEQUENCE: 117
atgatgagtg caagtgcaag aaataggtct cctttcacgc aaactcagtg gcaagagctt  60
gagcatcaag ctcttgtttt taagtacatg gttacaggaa cacccatccc accagatctc  120
atctactcta ttaaaagaag tctagacact tcaatttctt caaggctctt cccacatcat  180
ccaattgggt ggggatgttt tgaaatggga tttggcagaa aagtagaccc agagccaggg  240
aggtgcagaa gaacagatgg caagaaatgg agatgctcaa aggaggcata tccagactcc  300
aagtactgtg aaagacacat gcacagaggc agaaaccgtt caagaaagcc tgtggaagtt  360
tcttcagcaa taagcaccgc cacaaacacc tcccaaacaa tcccatcttc ttatacccga  420
aacctttcct tgaccaaccc caacatgaca ccaccctctt ccttcccttt ctctcctttg  480
ccctcttcta tgcctattga gtcccaaccc ttttcccaat cctaccaaaa ctcttctctc  540
aatcccttct tctactccca atcaacctcc tctagacccc cagatgctga ttttccaccc  600
caagatgcca ccacccacca gctattcatg gactctgggt cttattcgca tgatgaaaag  660
aattataggc atgttcatgg aataagagaa gatgtggatg agagagcttt cttcccagaa  720
gcatcaggat cagctaggag ctacactgaa tcataccagc aactatcaat gagctcctac  780
aagtcctatt caaactccaa ctttcagaac atcaatgatg ccaccaccaa cccaagacag  840
caagagcagc aacaacaaca acactgcttt gttttgggga cagacttcaa atcaacaaga  900
ccaactaaag agaaagaagc tgagacagct acgggtcaga gaccccttca ccgtttcttt  960
ggggagtggc caccaaagaa cacaacagat tcatggctag atcttgcttc caactccaga  1020
atccaaaccg atgaatga                                                1038

SEQ ID NO: 118          moltype = DNA  length = 1167
FEATURE                 Location/Qualifiers
source                  1..1167
                        mol_type = other DNA
                        organism = Glycine max
SEQUENCE: 118
atggacttcc atctgaagga atggagaaac cagcatgagt cagaggaaca acaacattct  60
acaaagatgc caaaacttct ccctgaatcc catcatcaac agccatctgc cactgcactc  120
cctttgtttg tacctgaacc caacagcagc agcaaagtca gcaccctgtc agattcaaca  180
ttagcagctg aaactgaaac aatgaccact acaaccacta acagattatt tcccaggatg  240
gggagctact tcagcttgtc tcagtggcag gagcttgagt tgcaggcttt gatattcagg  300
tacatgttgg ctggtgctgc tgttcctcct gaactccttc aaccaatcaa gaaaagcctt  360
cttcattccc ctcactattt cctccatcac cctctccaac attaccaacc tgctgctttg  420
ttgcaatcag ggtattgggg tagaggagcg atggatccgg agccagggcg gtgccggaga  480
accgacggca agaaatggcg gtgctcgagg gacgtggtgg ctgggcaaaa gtactgtgag  540
cgccacatgc atcgtggaag aaaccgttca agaaagcctg tggaactacc cacaccaact  600
agtgctaata attgtgatgg tggatctcta ggactaggtg cttcttcatc ttccatttct  660
tcaccacccc tagcttctgc ttcactcaaa tccccatttg atcttcttcg tcttaatgaa  720
cgttcctctg ggaccaagaa tgaagacgaa gaccatgtgg gtggggatgg cagatcaggt  780
ggagggggtg gccatatgct gaggcatttc ttcgatgatt ggccacgatc actgcaagac  840
tctgacaacg ttgaaaacaa tgctgctggc cctagcctct ctatttcaat gcccggaaat  900
gctgctgctg cttcctcgga tgtgtcattg aaattgtcca cgggctatgg agaggaccca  960
ggcccaagaa atgagaatgt gggcctcgtg gcagagcagc tgcagttgaa ttgggccgga  1020
ggatgggcct cgtctaatca agtggcttcc atgggaggac cactggccga ggcactcaga  1080
```

```
tcatctattt caacttcatc tcccactagt gttttgcatc acttgcctcg tggttctgga  1140
tctgagacca gcattattag cacctga                                      1167

SEQ ID NO: 119         moltype = DNA  length = 1782
FEATURE                Location/Qualifiers
source                 1..1782
                       mol_type = other DNA
                       organism = Glycine max
SEQUENCE: 119
atgggtgaat tatttggcgt tgggaaaaga agggacatca tcagcaacaa caacagtgct  60
agtagtagcg ttcttgggtt ggatgtgaag gtgcagagcc ctgaagtatt attccataat  120
aggatgacca tgatggggca tcataatcat cacctccatc cattgtcatc cccctttgat  180
aataataacg atatttcctg tgctgctggt gatggcgatg gtgatggtcc cacgacttac  240
atgtctctca ctaatcatat aaaccttgtt agtggtgctt ctgttcttgg tcctgctatt  300
gatggtggct gtggtgctgc tcctgctgca cctgtaagaa ctttgcagcc ttttcaaatt  360
tcttcttata cttctcccac caccactacc acagccttcg aaccctttttc aggtgtgatg  420
gcggcttcat tggggtttcc cttcacaagt gcacaatgga gggagcttga aaggcaggct  480
atgatataca agtacatgat ggcttcagtt cctgttccac ctgatctcct cattcctact  540
tcactcacat cctcttctcg ctcttcctgc atggatggtg gtttcaatct gaggttggca  600
aatagcactg accctgagcc aggtaggtgc agaagaacag atggaaaaaa atggagatgt  660
tcaagagacg tggctcctaa ccacaagtac tgcgagcgcc atatgcatag aggccgtccc  720
cgttcaagaa agcctgtgga agttaacacc aacaccactc ccactagcat caacaacaac  780
aataacaacc accaaatcaa aagggctcgc catgagtgta ataatccctt tgctacacct  840
gatgttgctg tggctatttc caatcccact tccagaaaag gtgaatcttc atcccatttt  900
cttgggtcta ctaccactca gccatacctt aaatctcccc tctgtcttgc taacttcggt  960
ctcaaagctg cgagttttga ctccgtggct tctgtttctg caaataagga acccaggggt  1020
ttggagtgga tgctgaatgg agatcctatt tccctggatg cttctaactc ccaatggcag  1080
tctctgatgc ataataaagt tggaatgagc agtgttagtt cctgtaatac caccgagtct  1140
cagtatctga attcatttgc actatatagc tctggactgg aacaacagaa cagacgccat  1200
cctttgttcc tgaatcctct tcttgttccc atgaaaaatc tccaaccaga gaaaccaagg  1260
ggtttcattg atgcttggtc taatgcagaa acagctcaaa gcaatgccaa caccaacaac  1320
aagaactctg ctgcatcaat tggtaaatta tccctctctt ctcttgatct atcaatgggg  1380
ggtggtgctg tgagtgaaga tgttgataat gttaacatgg gtttgggact aatggagact  1440
tatggaaaaa cacacactga tactaaaatc tctctctcaa attggcacaa cccggcacct  1500
tgggtggctt caagttcaac acttgggggt cctctagctg aagttctaag gtcaagcaca  1560
gtcactgcca cgaccaatga agcaacctcc aacgcaacct catcaccagc caccactaca  1620
catgctgaat ctaacagccc tctgggaaca atggtgtcat ctccatccgg ggtgttgcag  1680
aaaaccctta tttcattgtc tgatagcagt aacaatagca gccctacggt tgcatcatca  1740
agggccaatt ctgagatggc cttcctcagc tttaaattct ag                     1782

SEQ ID NO: 120         moltype = DNA  length = 1011
FEATURE                Location/Qualifiers
source                 1..1011
                       mol_type = other DNA
                       organism = Glycine max
SEQUENCE: 120
atggacttgc agttgaagca atggagaaac cagcatgagt cagagcaaga acaagaacat  60
tattccccaa acatggcaaa atttctatct caacaacaac acccaccacc atttccctct  120
gcactcccct tctttgtacc tgaacaaccc aacaccaaag tcagcacctt gtcagcattt  180
tctgattcca cattaccctc ttctcccaga tttcccagaa tggagagttg cttcagcttt  240
gcacaatggc aagagcttga gttgcaggct ctgatattca ggtacatgct ggccggtgct  300
cctgttcctc ctgagctcct tctaccaatc aagaaaagct tccttcaact ttatcaccct  360
cctaatttgt tggaatcagg gtactactgg cgaagagaag cactggatcc ggagccgggg  420
cggtgccgga ggaccgacgg caagaagtgg cggtgctcga aggacacggt ggcaggtcag  480
aagtactgcg accgccacat gcaccgtggc cggaaccgtt caagaaagcc tgtggaacaa  540
cgtgaaggat ctctttctgc tatagactct gtttcttctt cacactctgc ttcattcaat  600
ctccttcacc tcggtcaaag ttccgctgtg gccaagagtg acagcaagag cttgtctaga  660
aaccgtgatc atgtggatgg ggatggcaaa tcaaatggcc atgtcttgag gcatttcttt  720
gatgattggc caaggacact gcaagagcct gacaatggtg aaagcaatgg aagccagaac  780
aacaactcag gaaaatgtct ttctatgtca acaccaggaa tcgatccctc ggatgtgtcg  840
ttgaaattga ccactggcta tggagaggac gcgtgccagg cagcttcggt gggaggacca  900
cttgcagagg cattgagatc atccaccacc agctccactt cttcaccaac cagtgttctg  960
cttcagttgc ctcctagttc tgcttgtgag accagcttca ttagcaccta a           1011

SEQ ID NO: 121         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 121
cacatgcacc gtggccgcaa ccgttcaaga aagcctgtgg aatcacaaac tatgactcag  60
tc                                                                 62

SEQ ID NO: 122         moltype = DNA  length = 62
FEATURE                Location/Qualifiers
misc_feature           1..62
                       note = Synthetic GRF
```

```
source                  1..62
                        mol_type = other DNA
                        organism = synthetic construct
SEQUENCE: 122
catatgatac ggcggcgtta ccgttcaaga aagcctgtgg aatcatctca aactcactct  60
tc                                                                  62

SEQ ID NO: 123          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 123
cacatgcaca gagggaaaaa tcgttcaaga aagcctgtgg aagttttgaa aacaacacca  60
ac                                                                  62

SEQ ID NO: 124          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 124
cacatgcata gaggtcgaaa tcgttcaaga aagcctgtgg aaacatctca aattaactct  60
ca                                                                  62

SEQ ID NO: 125          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 125
cacatgcaca gagggaagaa tcgttcaaga aagcctgtgg aagttttgaa aacaacaaca  60
cc                                                                  62

SEQ ID NO: 126          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 126
catatgatac gacgtcgtta ccgttcaaga aagcctgtgg aatcatctca aactcactct  60
tc                                                                  62

SEQ ID NO: 127          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 127
cacatgaacc gaggacgcca tcgttcaaga aagcctgtgg aaggccaatc aggccatgcc  60
ct                                                                  62

SEQ ID NO: 128          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 128
cacatgcaca gagggaaaaa ccgttcaaga aagcctgtgg aagttttgaa aacaacacca  60
at                                                                  62

SEQ ID NO: 129          moltype = DNA  length = 62
FEATURE                 Location/Qualifiers
misc_feature            1..62
                        note = Synthetic GRF
source                  1..62
                        mol_type = other DNA
```

```
                         organism = synthetic construct
SEQUENCE: 129
cacatgaacc gaggacgcca tcgttcaaga aagcctgtgg aaggccaatc aggccatgcc  60
ct                                                                  62

SEQ ID NO: 130           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 130
cacatgaata gaggacgcca tcgttcaaga aagcctgtgg aaggccaatt aggccatgcc  60
ct                                                                  62

SEQ ID NO: 131           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 131
cacatgaaca gaggacgcca tcgttcaaga aagcctgtgg aaggccaatc aggccatgcc  60
ct                                                                  62

SEQ ID NO: 132           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 132
cacatgcacc gtggccgcaa ccgttcaaga aagcctgtgg aatcacaaac tatgactcac  60
tc                                                                  62

SEQ ID NO: 133           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 133
catatgcata gaggccgtcc ccgttcaaga aagcctgtgg aagttaacac caacagcacc  60
ac                                                                  62

SEQ ID NO: 134           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 134
cacatgcacc gtggccgcaa ccgttcaaga aagcctgtgg aatcacaaac tatgacacag  60
tc                                                                  62

SEQ ID NO: 135           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 135
cacatgcatc gtggccgaaa ccgttcaaga aagcctgtgg aacaacgtga tggatctctt  60
tc                                                                  62

SEQ ID NO: 136           moltype = DNA  length = 62
FEATURE                  Location/Qualifiers
misc_feature             1..62
                         note = Synthetic GRF
source                   1..62
                         mol_type = other DNA
                         organism = synthetic construct
SEQUENCE: 136
```

```
cacatgcacc gtggccgcaa ccgttcaaga aagcctgtgg aatcacaaac tatgactcac  60
tc                                                                 62

SEQ ID NO: 137         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 137
cacatgcacc gtggaagaaa ccgttcaaga aagcctgtgg aactacccac accaactagt  60
gc                                                                 62

SEQ ID NO: 138         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 138
cacatgcaca gaggtcgaaa tcgttcaaga aagcctgtgg aaacatctca agttaactct  60
cc                                                                 62

SEQ ID NO: 139         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 139
cacatgcaca gaggcagaaa ccgttcaaga aagcctgtgg aagtttcttc agcaacaagc  60
ac                                                                 62

SEQ ID NO: 140         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 140
cacatgcaca gagggaagaa tcgttcaaga aagcctgtgg aagttttaaa atcaacaaca  60
ac                                                                 62

SEQ ID NO: 141         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 141
cacatgcaca gaggcagaaa ccgttcaaga aagcctgtgg aagtttcttc agcaataagc  60
ac                                                                 62

SEQ ID NO: 142         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 142
cacatgcatc gtggaagaaa ccgttcaaga aagcctgtgg aactacccac accaactagt  60
gc                                                                 62

SEQ ID NO: 143         moltype = DNA  length = 62
FEATURE                Location/Qualifiers
misc_feature           1..62
                       note = Synthetic GRF
source                 1..62
                       mol_type = other DNA
                       organism = synthetic construct
SEQUENCE: 143
catatgcata gaggccgtcc ccgttcaaga aagcctgtgg aagttaacac caacaccact  60
cc                                                                 62
```

```
SEQ ID NO: 144          moltype = DNA  length = 62
FEATURE                 Location/Qualifiers
misc_feature            1..62
                        note = Synthetic GRF
source                  1..62
                        mol_type = other DNA
                        organism = synthetic construct
SEQUENCE: 144
cacatgcacc gtggccggaa ccgttcaaga aagcctgtgg aacaacgtga aggatctctt  60
tc                                                                 62

SEQ ID NO: 145          moltype = DNA  length = 22
FEATURE                 Location/Qualifiers
source                  1..22
                        mol_type = genomic DNA
                        organism = Glycine max
SEQUENCE: 145
ccgttcaaga aagcctgtgg aa                                           22

SEQ ID NO: 146          moltype = DNA  length = 22
FEATURE                 Location/Qualifiers
source                  1..22
                        mol_type = genomic DNA
                        organism = Glycine max
SEQUENCE: 146
tcgttcaaga aagcctgtgg aa                                           22

SEQ ID NO: 147          moltype = DNA  length = 1737
FEATURE                 Location/Qualifiers
source                  1..1737
                        mol_type = other DNA
                        organism = Triticum aestivum
SEQUENCE: 147
atggacctgg gcggggtgct gatggcggcc gcggacgcgg gggtgggcgg cggggacctc  60
ggcatgctcg gatctaggct gctcaagcac gggaggggca atgaggccga cgagcacggc  120
tggggcggcg gcaggccggc gtccaagcag gcccgggtcg ccggggacag cgacgcggtg  180
tccgaggccg tcaaggcggc cgcgccctac ctgctcggca cctgcagccc cgggcacggc  240
cgggagaaga tgctcagctt ctcctcctcg cagccggcct cctgcccctc cgccgctcag  300
gccgcgctgc cgctctacta cggcacgccc gcttcttgct cagggttgag ctcagtgagg  360
gggcccttca cgccgtcgca gtggatggag ctggagcacc aggccctgat ctacaagtac  420
ctggcggcca acatcgccgt gcctcacaac ctcgtcgtcc ccatccgccg gagcgtcacc  480
tcgctctacc cgtccgccta ctttggctcc tccacattgg ggtgggggcc tttccagctg  540
ggctactccg ggagcgcgga cctggagccc gggcggtgcc gccggacgga cggcaagaag  600
tggcggtgct ccagggacgc cgtcgccgac cagaagtact gcgagcggca tatgaaccgg  660
ggacgccatc gttcaagaaa gcatgtggaa ggccagcctg gccatgccgc gaaagcgatg  720
cctgcgacgg ccgctgctgc cgcccagccc ggtgctctcg ccaccggggg cggcggcgga  780
gctcccgccg gcgccgccat ctgccacgag cagcaaccgt tgaagaacta cgccgccagc  840
accattgatc cttgttcact gcaatataac agggaaatgg tgagcaagca gcaacacgag  900
tgcgagcaag tgcaggactc cgacaccctc tcgatgctga cctccatgag cgcgaggaac  960
accaatgcag gcagcatgtt cccgttctca aaggaacatc ataaccacaa tcctttcgag  1020
gtgacgagct cgaggccgga ctacgggctg gtttcatccg actcgctgat gagctcccct  1080
cacagctccc tggagaacgt caacctgctc acctcgcagc gagctctctc gagcgagcag  1140
cagagctcgc tctccctgca gcacttcgcg gactggccga ggacgccctc gcagcagggg  1200
cagggaggag gtctctcatg gccggacgcc gaggacatgc aagctcatca gaggacccag  1260
ctctcggtgt ccgccgttcc aatggcgtcc tctgacctgt cgtcggcctc cacgtccccg  1320
atccacgaga agctcatgct gtcgcccctc aagctgagcc gcgagtacag ccccatcggc  1380
ctcagcgtcg cggccacggc ggcggtggcg aaggacgagg gggaggcgaa ctggatgccc  1440
atgttccgcg actcgtccat gggcgggccg ctgggggagg ctctgaacaa gaacaatggc  1500
ggcaacatgg aggccaagag ctacctgtcg gcgtcgctga acctgatgac ggacgcctgg  1560
gactcgagcc cgctggagtc gtcgccggtg ggggtcctgc agaggaccgc cttcggatcg  1620
gtgtccagca gcaccggcag cagccccagg caggagtacc acggcgtgta tgatggtaac  1680
ccgcgggatg atctcggctc catcgtcgtg aatcacccca gcatccgcct gatgtga     1737

SEQ ID NO: 148          moltype = DNA  length = 678
FEATURE                 Location/Qualifiers
source                  1..678
                        mol_type = other DNA
                        organism = Triticum aestivum
SEQUENCE: 148
atgaccgagc gaaggcagga gcactcgccg ccgtccaaga tccccccgcct ctccggcgcc  60
gacgacgatg acggcgcagg gacggtgacc atggcggcgc cgtcgccgct ggttcttggg  120
ctgggtctcg gcgtaggcgg cagcagcagt gacagcggac gcggcgacgc ggaggcctct  180
gcggcgacgc ggccgtcggc gctgacgttc atgcagcggc aggagctgga gcaccaggtg  240
ctcatctacc gctacttcgc cgccaacgct cccgtgcccg tgcacctcgt gctccccatc  300
tggaagagcg tcgccgcttc ctcctccgcc ccgcagaggt ttccatccct ggcggggctg  360
gggagcatgt gctacgacca caggagcagc atggagccgg agccggaccg gtgccggcgc  420
acggacggca agaagtggcg gtgctcgcgc ggcgtggtgc cggggcacaa gtactgcgag  480
cgccacgtcc accgcggccg cagccgtgca agaaagcctg tggaagccgc ggcggccaca  540
```

```
tcagccgtcc cgatccgcgc gatgcacgcc gccgacgcgc agggcgccac cagtgcgcac  600
gcggcgccac cgcagcgcct cggcttctcc tcccccgccg gcgtctacct ggcgcacggc  660
accgcccgtg ccacctga                                                678

SEQ ID NO: 149          moltype = DNA  length = 1176
FEATURE                 Location/Qualifiers
source                  1..1176
                        mol_type = other DNA
                        organism = Triticum aestivum
SEQUENCE: 149
atggcgatgc cctttgcctc cctgtcgccg gcagccgacc accaccgctc ctcccccatc  60
ttccccttct gccgctcctc ccctctctac tcggcagggg aggaggcggc gcagcagcag  120
cagcagcacg cgatgagcgg cgcgaggtgg gcggcgatga ggccggcgac cttcacggcg  180
gcgcagtacc aggagctgga gcagcaggcg ctcatctaca agtacctcgt cgccggcgtg  240
cccgtcccgc cggatctcct cctccccatc cgccgcgact tcgactccct cgcctcgcgc  300
ttctaccacc accacgccct tgggtacggg tcctacttcg ggaagaagct ggatccggag  360
ccggggcggt gccggcggac ggacggcaag aagtggcggt gctccaagga ggccgcccag  420
gactccaagt actgcgagcg ccacatgcac cgcggccgca accgttcaag aaagcctgtg  480
gaaacgcagc tcgtcgccac gccccactcc cactcccact cccagcagct gcagcagcac  540
gcccccgccg ccaccgccgc cgcgttccac agccactcgc cgtacccggc gatcgccact  600
ggcggcggcg gcggcgcggc cggctccttc ggcctggggt ctgctcagct gcacatggac  660
aatgctgctg cgccttacgc gaccgctggt gcggccggaa acaaggattt caggtattct  720
gcctatgggt ttaggacttc ggcgctggag gagcacaacc agttcatcag cgcggccatg  780
gacaccgcca tggacaacta ctcatggcgc ctgatgccgg cccagaactc ggcgttctca  840
ctctcgagct accccatgct gggcaccctg ggcgacctgg accagagcgc gatctgctcg  900
ctggccaaga cggagaggga gccgctgtcc ttcggcggcg gcggcggctt cgaggacgac  960
gagtcggcgg tgaagcagga gaaccagacg ctgcggccct tcttcgacga gtggcccaag  1020
gacagggact cgtggccgga gctgcaggac catgactcca accacaacag caacgccttc  1080
tcggccacca agctgtccat ctccatcccg gtgaccagct ccgacttctc caccaccgcc  1140
ggctcccgct cgccccacgg tatatactcc cggtga                            1176

SEQ ID NO: 150          moltype = DNA  length = 1824
FEATURE                 Location/Qualifiers
source                  1..1824
                        mol_type = other DNA
                        organism = Triticum aestivum
SEQUENCE: 150
atggacctgg gcggggtgct gatggcggcc gcggacgcgg gggtgggcgg cggggagctc  60
ggcatgctcg gatctaggct gctcaagcac gggaggggca atgccgcggc ggcggaggcc  120
gacgagcgtc acgagcacgg gtggggcggc ggcaggccgg ccgccaagca ggcccgggtc  180
gccggggaca gcgacgccgt gtccgaggcc gtcaaggcgg ccgcgccata cctgctgggc  240
acctgcagcc ccgggcacgg ccgggagaag atgctcagct tctcctcctc gcagcagccg  300
ccctcctgcc cctccgccgc cgccgccgct caggccgcgc tgccgctcta ctacggcacg  360
cccgcttctt gcttagggtt gagctcggtg agcttgagcg ccagcatcca gggcgccatg  420
gccagggtga gggggccctt cacgccgtcg cagtggatgg agctggagca ccaggccctg  480
atctacaagt acctggcggc caacatcgcc gtgccgcaca gcctcctcgt ccccatccgc  540
cggagcgtca cctcgctcta cccgtccgcc tactttggct cctccacatt ggggtggggg  600
cctttccagc tgggctactc cgggagcgcg gacctggagc ccgggcggtg ccgccggacg  660
gacggcaaga agtggcggtg ctccagggac gccgtcgctg accagaagta ctgcgagcgg  720
catatgaacc ggggacgcca tcgttcaaga aagcatgtgg aaggccagcc tggccatgcc  780
gcgaaagcga tgcctgcgac ggtggcggct gctgccgccc agcccggtgc tctcgccacc  840
gggggcggcg gcggagccac cgccggcgcc gccatctgcc acgagcagca gccgttgaag  900
agctactccg ccagcaccat tgatccttgt tcactgcaat acaacaggga aatggcgagc  960
aagcagcaac acgagtgcga gcaagtgcag gactcggaca ccctctcgat gctgacctcc  1020
atgagcgcga ggaacaccaa cacgggcagc atgttccccgt tctcaaagga acatcataac  1080
cacaatcctt tcgaggtgac gagctcgagg ccggactacg ggctggtttc ctccgactcg  1140
ctgatgagct ccccccacag ctccctggag aacgtcaacc tgctcacctc gcagcgagcg  1200
ctctcgagcg agcagcagag ctcgctctcc ctgcagcact tcgcggactg gccgaggacg  1260
ccgtcgcagc aggggcaggg agggggaggc ctctcatggc cggacgccga gaacatgcag  1320
ctggctcatc agcggaccca gcagctctcg gtgtccgccg ctccgatggc gtcctccgac  1380
ctgtcgtcgg cctccacgtc cccatccac gagaagctca tgctgtcgcc cctcaagctg  1440
agccgcgagt acagccccat cggcctcagc gtcgcggcca cggcggcagc ggcggcgaag  1500
gacgaggggg aggcgaactg gatgcccatg ttccgcgact cgtccatggg cgggccactg  1560
ggggaggctc tgaacaagaa caatggcggc aacatggagg ccaagaacta cctgtcggcg  1620
tcgctgaacc tcatgacgga cgcctgggac tcgagcccgc tggagtcgtc gccggtgggg  1680
gtcctgcaga ggaccgcctt cgggtcggtg tccagcagca ccggcagcag ccccaggcag  1740
gagtaccacg gcgtgtatga tggtaatccg cgggatgatc tcggctccat cgtcgtgaat  1800
caccccagca tccgcctcat gtga                                         1824

SEQ ID NO: 151          moltype = DNA  length = 690
FEATURE                 Location/Qualifiers
source                  1..690
                        mol_type = other DNA
                        organism = Triticum aestivum
SEQUENCE: 151
atgaccgagc gaaggcagga gcactcgccg ccgtccaagc tcccccgcct ctccggcccc  60
gacgccgacg ccgacgacaa tgatggcgca gggacggtga ccatggcggc gccgtcgccg  120
ctggttcttg ggctgggtct cggcgtaggc ggcagctgca gtgacagcgg acgcggcgac  180
gcggaggcct ctgcggcgac gcggccgtcg gcgctgacgt tcatgcagcg gcaggagctg  240
```

```
gagcaccagg tgctcatcta ccgctacttc gccgccaacg ctcccgtgcc ggtgcacctc  300
gtcctcccca tctggaagag cgtcgccgcc tcctcctccg ccccgcagag gttcccatcc  360
ctggcgggac tggggagcat gtgctacgac cacaggagca gcatggagcc ggagccggac  420
cggtgccggc gcacggacgg caagaagtgg cggtgctcgc gcggggtggt gccggggcac  480
aagtactgcg agcgccacgt ccaccgcggc cgcggccgtg caagaaagcc tgtggaagcc  540
gcggcggcca catcagccat cccgatccgc gcgatgcacg ccgccgacgc gcagggcgcc  600
accagcgcgc acgcggcgcc gccgcagcgc ctcggcttct cctcccccgc cggcgtgtac  660
ctggcccacg gcaccgcccg tgccacctga                                    690

SEQ ID NO: 152         moltype = DNA  length = 1248
FEATURE                Location/Qualifiers
misc_feature           46..51
                       note = n is a, c, g, or t
source                 1..1248
                       mol_type = other DNA
                       organism = Triticum aestivum
SEQUENCE: 152
atgcttcctg agctcaccgc cgccgccatg gagctcgggc aggtgnnnnn ntacacgccg  60
ccggcgacca aggacgcgag atccggcggc ggcttcgccc aggccgccgc ttgcccctac  120
ccctacccct ccccccttcct cgacgagcag aagatgctca gcttctccaa ggccgccgcc  180
cctccatcgt caggtatgga ttttggcagg tccaatgagc agaggctgct gctggccagg  240
agcaagatgc ccttcactcc ttcacagtgg atggagctgg agcaccaggc cctcatatac  300
aagtatctca atgcaaaggc ccccatacct tccagcctgc tcatctccat cagcaaaagc  360
ttcagaccct cctccgatag aatgccctgg aggcctgtct accaagggtt caccaatgca  420
gattctgacc cggaacctgg aagatgccgt cgaacagacg gcaagaaatg gcggtgctca  480
aaggaggcga tggccgagca caagtactgt gagcggcaca tcaataggaa ccgccatcgt  540
tcaagaaagc ctgtggaaaa ccaaacaagg aagaacgcca aagagacgcc tgctgctggc  600
tcgttatcgg ccgctgtctc acagggtggc tgtaagaaag caaaagctgg tgatgaactg  660
aagccaggga gcgtcagcta ttggacagat aatttaaaca gggcaatggt gagcaaagcc  720
aggggaaaca accctgaaga aggcaacagt gctccactcc tgaattctac taatcaacaa  780
cacacattgt ccttgttctc tcaactgaag caacagagca aaccagataa gttcagcccg  840
gcagtcgata gtgaatcgat ctcctcaaat acagtattga agccctggga aagaagcaac  900
cagcagagca gcaaggacgt ttcttcgacg acgctccatg atcgcgggtg ccttcaatca  960
gtccttcaag atttcagcat gcataagaat gacaagatcg aggctcagaa aaacaatgct  1020
tcagtgccat caactttcta ttcacctaca gaaggtcaac acatcagctg ccttgcatct  1080
aacatgatgc aagtgcagga ggattgcatc tcaagctctt gggagatacc tcaaggtggg  1140
ccattaggtg aaatcctaac aaactccaag aacactgatg acttgaccaa taagtgtgaa  1200
tcaagatcat atggttggtt actgagtctt gatgaacatg aaatgtga                1248

SEQ ID NO: 153         moltype = DNA  length = 1164
FEATURE                Location/Qualifiers
source                 1..1164
                       mol_type = other DNA
                       organism = Triticum aestivum
SEQUENCE: 153
atggcgatgc cctttgcctc cctgtcgccg gcagccgacc accaccgctc ctcccccatc  60
ttccccttct gccgctcctc ccctctctac tcggtagggg aggagacggc gcatcagcag  120
cagcagcagc acacgatgag cggcgcgagg tgggcggcga ggccggcgac cttcacggcg  180
gcgcagtacg aggagctgga gcagcaggcg ctcatctaca agtacctcgt cgccggcgtc  240
cccgtcccgc cggatctcct cctccccatc cgccgcggct tcgactccct cgcctcgcgc  300
ttctaccacc accacgccct cgggtacggt tcctacttcg ggaagaagct ggatccggag  360
ccggggcggt gccggcggac ggacggcaag aagtggcggt gctccaagga ggccgcccag  420
gactccaagt actgcgagcg ccacatgcac cgcggccgca accgttcaag aaagcctgtg  480
gaaacgcagc tcgtcgccac gccccaccac tcccactccc agcagctgca gcagcacgcc  540
cccgccgcca gcgccgccgc gttccacagc cactcgccgt atccggcgat cgcctctggc  600
ggcggcggct ccttcgccgt gggatctgct cagctgcaca tggacaatgc tgcttcgcct  660
tacgcgaccg ctggtgccgc cggaaacaaa gatttcaggt attctgccta tgggtttagg  720
acttcggcga tggaggagca caaccagttc atctctgcgg ccatggagac cgccatggag  780
aactactcat gccgcctgat gccggcccag aactcatcct tctcactcgc cagctacccc  840
atgctgggca ccctgggcga ccttgaccag agcgcgatct gctcgctggc caagacggag  900
agggagcctc tgtccttctt cggcggcggc ggcggcttcg acgacgacga ctcggcggtg  960
aagcaggaga accagacgct gcggcccttc ttcgacgagt ggcccaagga cagggactcg  1020
tggccggagc tgcaggacca cgatgccaac aacagcagca acgccttctc ggccaccaag  1080
ctgtccatct ccatcccggt gaccagctcc gacttctcca ccaccgccgg ctcccgctcg  1140
cccaacggta tatactcccg gtga                                          1164

SEQ ID NO: 154         moltype = DNA  length = 1107
FEATURE                Location/Qualifiers
source                 1..1107
                       mol_type = other DNA
                       organism = Triticum aestivum
SEQUENCE: 154
atgctgagct cgtcggcggc gatggggatg gggctgggcg ggtacggcca gcagcagcag  60
cagcagatgc agatgcagat gcagcggggg gcggagccgg tgttcacgcc ggcgcagtgg  120
gccgagctgg agcagcaggc gctgatttac aagtacctca tggcgggcgt gcccgtgccg  180
cccgatctcc tgctccccat ccgcccccac cccgccggcg ccgccggaac caccttctcc  240
ttcgccaacc ccgccgcctc gcccttctac caccaccacc acccctccat gagttactac  300
gcctactatg gcaagaagct cgacccggag ccgtggcggt gccgacgcac cgacggcaag  360
aagtggcggt gctccaagga ggcgcacccc gactccaagt actgcgagcg ccacatgcac  420
```

```
cgtggccgca accgttcaag aaagcctgtg gaatccaagt ctgcttcccc tgcgcaccag  480
tcgcagcagc cccagttgtc cgccgtcacg tccgcggccc gcgacgccga gcctctcccc  540
tccctcccgg cgggggctaa aacccatggc ctgtccctcg gcggggctgg ctcgtcgcag  600
atgcacgtcg acgcctcgtc atacggcggc aaatactccc ttggagctaa atctgatgtg  660
ggtgaactga gcttcttctc tggagcatca ggaaacaaca acaggggatt caccatcgat  720
tccccaacgg acagctcgtg gcactcaatg ggatccagcc tgaccccata ccaactgtcg  780
aaacctagag attccggcct catgcagggc ggcttctcgt attcccactt tgagccgtcg  840
caggagctcg ggcaggtaac catcgcctcg ctgtcccact cccaggagca ggaccgccgc  900
tctttcgggg gcggtggtgg aggtgggggt ggaggggcag ggctcatggg aaatgttaag  960
caggagaacc agccgctgag gcccttcttc gacgagtggc cggggaggcg ggactcgtgg  1020
tcggagatgg acgacgagcg ctccaacggc acctccttct cgacgaccca gctctcgatc  1080
tccatcccaa tgcctcgatg cgattga                                      1107
```

```
SEQ ID NO: 155          moltype = DNA  length = 1227
FEATURE                 Location/Qualifiers
source                  1..1227
                        mol_type = other DNA
                        organism = Triticum aestivum
SEQUENCE: 155
atggagctcg ggcaggtgct gggctacacg ccaccggcga ccaaggacgc gagatccggc  60
ggcggcttca cccaggctgc cgcttgcccc tacccctacc cctcccccttt cctcgacgag  120
cagaagatgc tcagcttctc caaggccgcc gccgctcacc agccgccctc aggtatggat  180
tttgggaggt ccaatgagca gaggctgttg ctggccagga gcaagatgcc cttcacccct  240
tcacagtgga tggagctgga gcaccaggcc ctcatttaca agtatctcaa tgcaaaggcc  300
cccatacctt ccggcctgct catctccatc agcaagagct tcagaccctc ctccgataga  360
atgccctgga ggcctgtcta tcaagggttc accaatgcag attctgaccc ggaacctgga  420
agatgccgtc gaacagacgg caagaaatgg cggtgctcaa aggaggcgat ggccgagcac  480
aagtactgtg agcggcacat caataggaac cgccatcgtt caagaaagcc tgtggaaaac  540
caaacaagga agaacgccaa agagacacct gctgctggct cgatatcggc cgctgtctca  600
cagggtggct gtaagaaagc aaaagctggt gatgaactga agccagggag cgtcagttat  660
tggacagata atttaaacag ggcaatggtg agcaaagcca ggggaaacaa ccctgaagaa  720
ggcaacagtg ctccactcct gaattctact aatcaacaac acacattgtc cttgttctct  780
caactgaagc aacagagcaa accagataag ttcagcccgg cagtcgatag tgaatcgatc  840
tcctcaaata ctgtattgaa gccttgggaa agaagcaacc agcagagcag taaggacgtt  900
tcttccacga cgctccatga tcgcgggtgc cttcaatcag tccttcaaga tttcagcatg  960
cataagaatg acaagatcga gtctcagaaa aacaatgctt cagtgccatc tactttctat  1020
tcatctacag aaggtcgaca catcagctgc cttgcatcta acatgatgca agtgcaggag  1080
gattgcatct caagctcttg ggagatacct caaggtgggc ctttaggtga aatcctaaca  1140
aactccaaga atactgatga cttgaccaat aagtgtgaat caagatcata tggttggtta  1200
ctgagtcttg atgaacatga aatgtga                                      1227
```

```
SEQ ID NO: 156          moltype = DNA  length = 1836
FEATURE                 Location/Qualifiers
source                  1..1836
                        mol_type = other DNA
                        organism = Triticum aestivum
SEQUENCE: 156
atggacctgg gcggcgtgct gatggcggcc gcggacgcgg gggtgggcgg cggggacctg  60
ggcatgctcg gatctaggct gctcaagcac gggaggggca atgcggcggc ggcggaggcc  120
gacgagcacg gctggggcag cggcaggccg cccgccaagc aggcccgggt cgcggcctcg  180
gccgcgtccg gggacagcga cgccgtgtcc gaggccgtca aggcggcggc accctacctg  240
ctcggcacct gcagccccgg gcacggccgg gagaagatgc tcagcttctc ctcctcgcag  300
ccgccctcct gcccctcctc cgccgccgcc gccgccgctc aggccgcgct gccgctctac  360
tacggcacgc ccgcttcttg ctcagggttg agctcggtga gcttgagcgc cagcatccag  420
aacgccatgg ccagggtgag ggggcccttc acgccgtcgc agtggatgga gctggagcac  480
caggccctga tctacaagta cctggcggcc aacatcgccg tgcctcacaa cctgctcgtc  540
cccatccgcc ggagcgtcac ctcgctctac ccgtccgcct actttggctc ctccacattg  600
gggtgggggc ctttccagct gggctactcc gggagcgcgg acctggagcc cgggcggtgc  660
cgccggacgg acggcaagaa gtggcggtgc tccagggacg ccgtcgccga ccagaagtac  720
tgcgagcggc atatgaaccg gggacgccat cgttcaagaa agcatgtgga aggccagcct  780
ggccatgccg cgaaagcgat gcctgcgacg gtggcggcgg ctgctgccca gcccggtgct  840
ctcgccaccg gggcggcgg cggagctacc gccggcgccg ccgccatctg ccacgagcag  900
cagccgttga agaactacgc cgcgaacacc attgatcctt gttcactgca atataacagg  960
gaaatggtga gcaagcagca gcaacacgag tgcgagcaag tgcaggactc cgacaccctc  1020
tcgatgctga cctccatgag cgcgaggaac accaacacgg gcagcatgtt cccgttctca  1080
aaggagcatc acaatcacaa tcctttcgag gtgacgagct caaggccgga ctacggctg  1140
gtttcatccg actcgctgat gagctcccct cacagctccc tggagaacgt caacctgctc  1200
acctcgcact cgcagcgagc gctctccaac gagcagcaga gctcgctctc cctgcagcac  1260
ttcgcggact ggccgaggac gccctcgcag cagggcaag gaggaggagg tctctcatgg  1320
ccggacgccg aggacatgca agcacatcag aggacccagc tctcggtgtc cgccgctcca  1380
atggcgtccc ccgacctgtc gtcggcctcc acgtccccga tccacgagaa gctcatgctg  1440
tcgcccctca agctgagccg cgagtacagc cccatcggcc tcagcatcgc ggcgacggcg  1500
gcggcggcga aggacgaggg ggaggcgaac tggatgccca tgttccgcga ctcgtccatg  1560
ggcgggccgc tgggggaggc cctgaacaag aacaatggcg gcaacatgga ggccaagaac  1620
tacctgtcgg cgtcgctgaa cctcatgacg gacgcctggg actcgagccc gctggagtcg  1680
tccccggtgg gggtcctgca gaggaccgcc ttcgggtcgg tgtcgagcag caccggcagc  1740
agccccaggc aggagtacca cggcgtgtat gatggtaacc cgcgggatga tctcggctcc  1800
atcgtcgtga atcaccccag catccgcctc atgtga                            1836
```

```
SEQ ID NO: 157          moltype = DNA  length = 930
FEATURE                 Location/Qualifiers
source                  1..930
                        mol_type = other DNA
                        organism = Triticum aestivum
SEQUENCE: 157
atgatgctgg gagggcacgg cggcggcggc gggaggtgcc tgttcacggc gtcgcagtgg  60
cgggagctgg agcaccaggc gctcatctac aagtacatgg ccgccggctc gcaggtgccc  120
cacgagctgg tcctcccgct ccgccaccgc gacgccgccg ccttcgccgg catcgacacc  180
gccccctccg tcgcctgcta ccctcctccg cagccctccc tggggtgggg gctctacggg  240
gcgggggcgc agtacgcgcg gaagccggag gacccggagc ccgggcggtg ccggcggacg  300
gacggcaaga agtggcgctg ctccagggag gcgtacgggg agtccaagta ctgcgacagg  360
cacatgcacc gcggcaagaa ccgttcaaga aagcctgtgg aaccgatgag ctcctcctcc  420
gtctcctccc cggccgcctc ctaccgccag accaccctct ccatgtcgcc ccccacgccg  480
gccgacacgc ccagctacgg ccacggccac ctccgcgcag ctgcttctca gagccagata  540
aaccctctcc agctccacct cgacaccccg tcgcccccgc cgtcctacca caggtacgcg  600
ccggcgcagc agtacggggg ctccttcttc ccgagcaggc agcaggtgca ggaggaggcc  660
gaggcggagg cgaggcggcg gcagcacttc ctggctctcg gcgccgacct gagcctggac  720
aagccggacg ccaccaccgc ggcgtcctcg acaaccgagg agaagccgct gcggcgcttc  780
ttcgacgagt ggccgcgcga cgggaacgcc gtcgaggttc ggccctggaa tatgggccac  840
cgggacgaga cgctgctctc catgtccatc cccacgacga cggcctcgca ccccgacctc  900
gccgcctacc gccaccacaa cgatgaataa                                   930

SEQ ID NO: 158          moltype = DNA  length = 1233
FEATURE                 Location/Qualifiers
source                  1..1233
                        mol_type = other DNA
                        organism = Triticum aestivum
SEQUENCE: 158
atgatgatga tgggcggtcg cgcgggggcc ggcggcgtcg gggccggcgg gggccggtgc  60
ccgttcacgg cgacgcagtg gcaggagctg gagcaccagg cgctcatcta caagtacatg  120
gcctccggcg tgcccatccc ctccgacctc ctcctcccgc tccgccgcag cttcctcctc  180
gactccgccc tcgccacctc cccctccctc gccttccctc cccaggccgc actgggctgg  240
ggatgtttcg ggatggggtt cggccggaag gcggaggacc cggagccggg gcggtgccgg  300
cggactgacg gcaagaagtg gcgctgctcc aaggaggcgt acccggactc caagtactgc  360
gagaagcaca tgcaccgcgg caagaaccgt tcaagaaagc ctgtggaaat gtccttggcc  420
acgcccccgc cgccgccttc ctcctcggcc tcctcctcct cctccaacgt ccactccgcc  480
gtcaacgccg ccaccaccac cacctccccc gcgccgtcct accaccgcca cgccgccgcg  540
actcacgaca cgacgcccta ccacacgctc tacggcggcc cctactcctc cgccggccgc  600
cagcagcacg ccagcgccta ccaccacgcc gcgcaggtca gcccgttcca cctgcacctc  660
gacaccaccc acccgcaccc gccgccgtcc tactactcca ccatggacca cagcaaggac  720
agctacgcct acgggcacag cgtcaaggag gtgcacggcg gcggcgagca cgccttcttc  780
tcctccgacg tcaccactga cagggaccac caccaccacc aacaccacgc cggcgccggc  840
ggcaacgggc agtggcagtt caagcagctc ggcggcatgg agcccaagca gcacaacccc  900
acgtcgctct tccccggctg cggcgggtac ggcaacaacg cggcgtacgc catcgacctg  960
tccagcaaag aagaggacga ggagaaggag aggcggcagc agcagcagca ctgcttcctg  1020
ctgggcgccg acctgaggct cgacaagccg tcgtcggggc acggcgactc cgccgaccag  1080
aagcctctcc ggcccttctt cgacgagtgg ccgcacgaga agaccgggag caaggggtcg  1140
tggatggggc tcgaggggga gacgcagctc tccatctcca tcgccaacga actccccatc  1200
accaccacct cccgctacca ccatggtgaa tga                                1233

SEQ ID NO: 159          moltype = DNA  length = 1230
FEATURE                 Location/Qualifiers
source                  1..1230
                        mol_type = other DNA
                        organism = Triticum aestivum
SEQUENCE: 159
atggcgatgc cgtatgcctc tctttccccg gcaggcgacc gccgctcctc cccggccgcc  60
accgcctccc tcctcccctt ctgccgctcc tccccttctc ccgccggcgg cggcaatggc  120
ggcatggggg aggaggcgcg gatggacggg aggtggatgg cgaggccggt gcccttcacg  180
gcggcgcagt acgaggagct ggagcaccag gcgctgatat acaagtacct ggtggccggc  240
gtgcccgtcc cgccggatct cgtgctcccc atccgccgcg gcatcgaatc cctcgccgcc  300
cgcttctacc acaacccct cgccatcggg tacggatcgt acctaggcaa gaaggtggat  360
ccggagccgg gccggtgccg gcgcacggac ggcaagaagt ggcggtgcgc caaggaggcc  420
gcctccgatt ccaagtattg cgagcgccac atgcaccgcg gccgcaaccg ttcaagaaag  480
cctgtggaaa cgcagctcgt cccgcacacc cagccgccgg ccgcctccgc cgtgccgccc  540
ctcgccaccg gcttccacag ccactccctc taccccgcca tcggcggcag caccaacggt  600
ggtggaggcg gggggaacaa cggcatgtcc atgcccagca cgttctcctc cgcgctgggg  660
ccgcctcagc agcacatggg cagcaatgcc gcctctccct acgcggctct cggtggcgcc  720
ggaacatgca aagatttcag gtataccgca tatggaataa gatctttggc agacgagcac  780
agtcagctca tgacagaagc catgaatacc tccgtggaga acccatggcg cctgccgccg  840
tcgtctcaaa cgacctcatt cccgctttca agctacgctc ctcagcttgg agcaacgagt  900
gacctgggtc agaacaacaa ccacaacaac agcagcagca acagtgccgt caagtccgag  960
cggcagcagc cgctctcctt cccggggtgc ggcgactttg gcggcggcgg catggactcc  1020
gcgaagcagg agaaccagac gctgcggccg ttcttcgacg agtggccgaa gacgagggac  1080
tcgtggtcgg acctgacgga cgacaactcc agcctcgcct ccttctcggc cacccagctg  1140
tcgatctcga tacccatgac gtcctccgac ttctccgccg ccagctccca gtcgcccaac  1200
ggtatgctgt tcgccggcga gatgtactag                                   1230
```

```
SEQ ID NO: 160          moltype = DNA  length = 1113
FEATURE                 Location/Qualifiers
source                  1..1113
                        mol_type = other DNA
                        organism = Triticum aestivum
SEQUENCE: 160
atgctgagct cgtcggcggc gatggggatg gggctgggcg ggtacggcca gcagcagcag  60
cagcagcaga tgcagatgca gatgcagatg cagcgggggg cggggccggt gttcacgccg  120
gcgcagtggg ccgagctgga gcagcaggcg ctgatttaca agtacctcat ggcgggcgtg  180
cccgtgccgc ccgatctcct gctccccatc cgcccccacc ccgccggcgc cggagccacc  240
ttctccttcg ccaaccccgc cgcctcgccc ttctaccacc accaccaccc ctccatgagt  300
tactacgcct actatggcaa gaagctcgac ccggagccgt ggcggtgccg ccgcaccgac  360
ggcaagaagt ggaggtgctc caaggaggcg caccccgact ccaagtactg cgagcgccac  420
atgcaccgtg gccgcaaccg ttcaagaaag cctgtggaat ccaagtctgc ttcccctgcg  480
caccagtcgc agcagccccc gttgtccgcc gtcacgtccg ccacccgcga cgcccgagcct  540
ctcccctccc tcccggcggg ggctaagacc catggcctgt ccctcggcgg ggctggctcg  600
tcgcagatgc acgtcgacgc ctcgtcatac ggcaacaaat actcccttgg agctaaatct  660
gacgtgggtg aactgagctt cttctctgga gcatcaggaa acaacaacag gggcttcacc  720
atcgattccc caacggacag ctcgtggcac tcaatgggat ccagcctgcc cccgtaccaa  780
ctgtcgaaac ctagagattc cggcctcatg caaggcggct tctcgtattc ccactttgag  840
ccgtcgcagg agcttgggca ggtaaccatc gcctcgctgt cccactccca ggagcaggac  900
cgccgctcct tcggtggcgg cggtggtggt ggaggtggag gggcagggct catgggaaat  960
gttaagcagg agaaccagcc gctgaggccc ttcttcgacg agtggccggg gaggcgggac  1020
tcgtggtcgg agatggacga cgagcgctcc aacggcacct ccttctcgac gacccagctc  1080
tcgatctcca tcccaatgcc tcgatgtgat tga                              1113

SEQ ID NO: 161          moltype = DNA  length = 684
FEATURE                 Location/Qualifiers
source                  1..684
                        mol_type = other DNA
                        organism = Triticum aestivum
SEQUENCE: 161
atgaccgagc gaaggcagga acactcgccg ccgtccaagc tcccccgcct ctccggcccc  60
gacgccgacg acaacgacgg cgcagggacg gtgaccatgg cggcgccgtc gccgctggtt  120
cttgggctgg gtctcggcgt aggcggcagc agcagtgaca gtggacgtgg cgacgcggag  180
gcatctgcgg cgacgcggcc atcggcgctg acgttcatgc agcggcagga gctggagcac  240
caggtgctca tctaccgcta cttcgccgcc aacgctcccg tgcccgtgca cctcgtcctc  300
cccatctgga agagcgtcgc cgcctcctcc tccgccccgc agaggttccc atccctggcg  360
ggactgggga gcatgtgcta cgaccacagg agcagcatgg agccggagcc ggaccggtgc  420
cggcgcacgg acggcaaaaa gtggcggtgc tcgcgcggcg tgatgccggg gcacaagtac  480
tgcgagcgcc acgtccaccg cggccgcggc cgtgcaagaa agcctgtgga agccgcgccg  540
gccacatcag ccatcccgat ccgcgcaatg cacgccgccg acgcgcaggg cgccacaagc  600
gcgcacgcgg cgccaccgca gcgcctcggc ttctcctccc ccgccggcgt ctacctggcc  660
cacggcaccg cccgtgccac ctga                                        684

SEQ ID NO: 162          moltype = DNA  length = 648
FEATURE                 Location/Qualifiers
source                  1..648
                        mol_type = other DNA
                        organism = Triticum aestivum
SEQUENCE: 162
atggccgacg agaaagaagc cgactcgctg cagccgccgt ccaagcagcc ccgcctctcc  60
tccgccgact cgaacgccgg tgcggtgacg atggcggtct cgtcgccgct gggtcttggc  120
ctcggcctgg gactcggcgg cgatagccgc ggcgagcagc aggccttcca agcacgggca  180
gccgcggcgg cggcgaaatc ggcgctgacg ttcatgcagc agcaggagct ggagcaccag  240
gtgctcatct accgctactt cgcggcgggg gcgcccgtgc cggtgaacct cgtgctgccc  300
atctggaaga gcatcgccgc ctcctccttc ggcccgcacc gcttcccctc cctgattggg  360
cttgggagcc tgtgcttcga ctaccggagc agcatggagc cggagcccgg gaggtgccgc  420
cgcacggacg gcaagaagtg gcggtgctcc cgcgacgtgc tgcaggggca caagtactgc  480
gagcggcacg tccaccgggg ccgcggccgt tcaagaaagc ctgtggaagg agcccccgca  540
gccccggcgc acagcggcag cagcaccacc gccccgcccc gcgccatcgg cttctccccc  600
gccggcatcc tccacgccac ccacagcgcc gccgcgcgcg ccacctga              648

SEQ ID NO: 163          moltype = DNA  length = 963
FEATURE                 Location/Qualifiers
source                  1..963
                        mol_type = other DNA
                        organism = Triticum aestivum
SEQUENCE: 163
atgatgctgg gagggcacgg cggcggcggc ggcgggaggt gcctgttcac ggcgtcgcag  60
tggcgggagc tggagcacca ggcgctcatc tacaagtaca tggccgccgg ctcgcaggtg  120
ccccacgagc tggtcctccc gctccgccac cgcgacgctg ccgccttcgc cgccatcgac  180
accgtcccct ccctcgcctg ctaccctcct ccgcagccat ccctggggtg ggggctctac  240
ggggcggggg cgcagtacgc gcggaagccg gaggacccgg agccggggcg gtgccggcgg  300
acggacggca agaagtggcg ctgctccagg gaggcgtacg gggagtccaa gtactgcgac  360
aggcacatgc accgcggcaa gaaccgttca agaaagcctg tggaaccgat gtcctcctcc  420
tccgtctcct ccccggccgc ctcctaccgc cagaccgccc tctccatgtc gccccccacg  480
ccggccgaca cgcccaccta cggccacggc cacggccacg accacctccg cgcagctgct  540
ggtcagagtc agagccagat aaaccctctc cagctccacc tcgacacccc gtcgcccccg  600
```

```
ccgtcctacc acaggtacgc gccggcgcag cagtacgggg gctccttctt ccagaacagg  660
cagcaggtgc aggaggaggc ggaggcggag gcgaggcggc ggcagcactt cctggctctc  720
ggcgccgacc tgagcctgga caagcccgac gccaccaccg cggcgtcctc gacaaccgag  780
gagaagccgc tgcggcgctt cttcgacgag tggccgcgcg acgggaacgc cgtcgagggt  840
cggccctgga atatgggcca ccgggacgag acgctgctct ccatgtccat ccccacgacg  900
acggccacgc accccgacct cgccgccgcc tcgcgctacc accaccacca caacgatgaa  960
taa                                                                963

SEQ ID NO: 164          moltype = DNA  length = 1245
FEATURE                 Location/Qualifiers
source                  1..1245
                        mol_type = other DNA
                        organism = Triticum aestivum
SEQUENCE: 164
atgatgatga tgggtggtcg cgcgggggcc ggcggcgtcg gggcaggcgg ggggcggtgc  60
ccgttcacgg cgacgcagtg gcaggagctt gagcaccagg cactcatcta caagtacatg  120
gcctccggcg tgcccatccc ctccgacctc ctcctcccgc tccgccgcag cttcctcctc  180
gactccgccc tcgccacctc cccctccctc gccttccctc cccaggccgc acttggctgg  240
ggttgctttg gcatggggtt cggccggaag gcggaggacc cggagccggg gcggtgccgg  300
cggacggacg gcaagaagtg gcgctgctcc aaggaggcgt acccggactc caagtactgc  360
gagaagcaca tgcaccgcgg caagaaccgt tcaagaaagc ctgtggaaat gtccttggcc  420
acgcccccgc cgccgccttc ctcctcggcc tcctcctcct cctccaacgt ccactccgcc  480
gtcaacgtcg ccaccaccac ctcctccccc gcgccgtcct accaccgcca cgccgccgcg  540
actcacgaca cgacgcccta ccacgcgctc tacggcggcc cctactcctc cgccggccgc  600
cagcagcacg ctagcgccta ccaccacgcc gcgcaggtca gcccgttcca cctgcacctc  660
gacaccaccc acccgcaccc gccgccgtcc tactactcca gcatggacca cagcaaggac  720
agctacgcct acgggcacag cgtcaaggag gtgcacggcg gcggcgagca cgccttcttc  780
tcctccgacg tcaccaccga cagggaccat caccaccacc accatcagca ccaacaccac  840
gctagcgccg gcggcaacgg ccagtggcag ttcaagcagc tcggcggcat ggagccgaag  900
cagcataacc caacgtcgct cttccccggc tgcggcggct acggcaacaa cgcggcctac  960
gccatcgacc tgtccagcaa agaagaggac gaggagaagg agaggcggca gcagcagcag  1020
cactgcttcc tgctgggcgc cgacctgagg ctcgacaagc cgtcgtcggg gcacggcgac  1080
tccgccgacc agaagcctct ccggcccttc ttcgacgagt ggccgcacga gaagaccggg  1140
agcaaggggt cgtggatggg gctcgagggg gagacgcagc tctccatctc catcgccaac  1200
gaactcccca tcaccaccac ctcccgctac caccatggtg aatga                  1245

SEQ ID NO: 165          moltype = DNA  length = 1221
FEATURE                 Location/Qualifiers
source                  1..1221
                        mol_type = other DNA
                        organism = Triticum aestivum
SEQUENCE: 165
atggcgatgc cgtatgcctc tctttccccg gcaggcgacc gccgctcctc cccggccgcc  60
accgcctccc tcctcccctt ctgccgctcc tccccgttct ccgccggcaa tggcggcatg  120
ggggaggagg cgcggatggc cggtaggtgg atggcgaggc cggcgccctt cacggcggcg  180
cagtacgagg agctggagca ccaggcgctg atatacaagt acctggtggc cggcgtgccc  240
gtcccgccgg atctcgtgct ccccatccgc cgcggcatcg agaccctcgc cgcccgcttc  300
taccacaacc ccctcgccat cgggtatgga tcgtacctgg gcaagaaggt ggatccggag  360
cccggccggt gccggcgcac ggacggcaag aagtggcggt gcgccaagga ggccgcctcc  420
gactccaagt attgcgagcg ccacatgcac cgcggccgca accgttcaag aaagcctgtg  480
gaaacgcagc tcgtctcgca ctcccagccg ccggccgcct ccgtcgtgcc gcccctcgcc  540
accggcttcc acaaccactc cctctacccc gccatcggcg gcaccaacgg tggtggaggc  600
ggggggaaca acggcatgcc caacacgttc tcctccgcgc tggggcctcc tcagcagcac  660
atgggcaaca atgcctcctc accctacgcg gctctcggtg gcgccggaac atgcaaagat  720
ttcaggtata ccgcatatgg aataagatct ttggcagacg agcacagtca gctcatgaca  780
gaagccatga atacctccgt ggagaaccca tggcgcctgc cgccatcgtc tcaaacgacc  840
acattcccgc tctcaagcta cgctcctcag cttggagcaa ctagtgacct gggtcagaac  900
aacaacagca gcagcagcaa cagtgccgtc aagtccgaac ggcagcagca gcagcagccc  960
ctctccttcc cggggtgcgg cgacttcggc ggcggcggcg ccatggactc cgcgaagcag  1020
gagaaccaga cgctgcggcc gttcttcgac gagtggccca agacgaggga ctcgtggtcg  1080
gacctgaccg acgacaactc cagcctcgcc tccttctcgg ccacccagct gtcgatctcg  1140
atacccatga cgtcctccga cttctcggcc gccagctccc agtcgcccaa cggtatgctg  1200
ttcgccggcg aaatgtacta g                                            1221

SEQ ID NO: 166          moltype = DNA  length = 1116
FEATURE                 Location/Qualifiers
source                  1..1116
                        mol_type = other DNA
                        organism = Triticum aestivum
SEQUENCE: 166
atgctgagct cgtcggcggc gatggggatg gggctggggg gctacggcca gcagcagcag  60
cagcagatgc agatgcagat gcagcggggc gcggggccgg tgttcacgcc ggcgcagtgg  120
gccgagctgg agcagcaggc gctgatttac aagtacctca tggcaggcgt gcccgtgccg  180
cccgatctcc tgctccccat ccgcccccac caccccgccg ccggcgccgc cggaaccacc  240
ttctccttcg ccagccccgc cgcctcgccc ttctaccacc accaccatcc ctccatgagt  300
tactacgcct actatggcaa gaagctcgac ccggagccgt ggcggtgccg gcgcaccgac  360
ggcaagaagt ggcggtgctc caaggaggcg caccccgact ccaagtactg cgagcgccac  420
atgcaccgtg gccgcaaccg ttcaagaaag cctgtggaat ccaagtctgc ttcccctgcg  480
caccagtcgc agcagccccc gctgtccgcc gtcacgtccg cggcccgcga cgccgagccg  540
```

```
ctcccctccc tcccggctgg ggctaaaacc catggcctgt ccctcggcgg ggctggctcg  600
tcgcagatgc acgtcgacgc ctcatcatac ggcggcaaat actcccttgg agctaaatct  660
gatgtgggtg aactgagctt cttctctgga gcatcaggaa acaacaacag gggcttcacc  720
atcgattccc caacggacag ctcgtggcac tcgatggggt ccagcctgcc cccgtaccaa  780
ctgtcgaaac ctagagattc cggcctcatg caaggcggct tctcgtattc ccactatgag  840
ccgtcgcagg agcttgggca ggtaaccatc gcctcgctgt cccactccca ggagcaggac  900
tgccgctctt tgggtggtgg aggtggagga ggtggaggtg gaggtggagg gctcatggga  960
aatgtcaagc aggagaacca gccgctgagg cccttcttcg acgagtggcc ggggaggcgg  1020
gactcgtggt cggagatgga cgacgagcgc tccaacggca cctccttctc gacgacccag  1080
ctctcgatct ccatcccgat gcctcgatgc gattga                           1116

SEQ ID NO: 167         moltype = DNA  length = 1155
FEATURE                Location/Qualifiers
source                 1..1155
                       mol_type = other DNA
                       organism = Triticum aestivum
SEQUENCE: 167
atggcgatgc cctttgcctc cctgtcgccg gcagccgacc accaccgctc ctccccccatc  60
ttccccttct gccgctcctc ccctctctac tcggcagggg aggaggcggc gcagcagcag  120
cagcagcagc agcacgcgat gagcggcgcg aggtgggcgg cggcgaggcc ggcgaccttc  180
acggcggcgc agtacgagga gctggagcag caggcgctca tctacaagta cctcgtcgcc  240
ggcgtgcccg tcccgccgga tctcctcctc cccatccgcc ggggcttcga ctccctcgcc  300
tcgcgcttct accaccacca cgcccttggg tacgggtcct acttcgggaa gaagctggat  360
ccggagccgg ggcggtgccg gcggacggac ggcaagaagt ggcggtgctc caaggaggcc  420
gcccaggact ccaagtactg cgagcgccac atgcaccgcg gccgcaaccg ttcaagaaag  480
cctgtggaaa cgcagctcgt ctcccactcc cagcagctgc agcagcaggc ccccgccgcc  540
gcgttccacg gccactcgcc gtacccggcg atcgccactg gcgccggcgc gcccggctcc  600
ttcgccctgg ggtctactgc tcagctgcac atggataatg ctgctgcgcc ttacgcgacc  660
gctggcgccg ccgggaacaa agatttcagg tattctgcct atgggtttag gacttcggcg  720
atggaggacc acaaccagtt catcagtgcg gccatggaca ccgccatgga caactactca  780
tggcgcctgc tgccggccca gaactcgtcc ttctcactct cgagctaccc catgctgagc  840
accctgagcg acctggacca gagcgcgatc tgctcgctgg ccaagacgga gagggagccg  900
ctgtccttct tcggcgtggg cggcggcttc gacgacgacg agtcggcggt gaagcaggag  960
aaccagacgc tgcggccctt cttcgacgag tggcccaagg acagggactc gtggccggag  1020
ctgcaggacc atgactccaa ccacaacaat gaggccttct cggccaccaa gctgtccatc  1080
tccatcccgg tgaccagctc cgatttctcc accaccgccg gctcccgctc gccccacggt  1140
atatactccc ggtga                                                  1155

SEQ ID NO: 168         moltype = DNA  length = 639
FEATURE                Location/Qualifiers
source                 1..639
                       mol_type = other DNA
                       organism = Triticum aestivum
SEQUENCE: 168
atggccgacg agaaagaagc cgactcgctg cagccgccgt ccaagcagcc ccgcctctcc  60
tccgccgact cgaacgccgg ggcggtgacg atggcggtct cgtcgccgct gggtcttggc  120
ctcggcctgg ggctcggtgg cgatagccgt ggcgagcagc aggccttcga agcacgggcg  180
gcggcgaagt cggcgctgac gttcatgcag cagcaggagc tggagcacca ggtgctcatc  240
taccgctact tcgcggcggg ggcgcccgtg ccggtgcacc tcgtgctgcc catctggaag  300
agcgtcgccg cctcctcctt cggcccgcac cgcttcccct ccctgattgg gctggggagc  360
ctgtgcttcg actaccggag cagcatggag ccggagcccg ggcggtgccg ccgcacggac  420
ggcaagaagt ggcggtgctc ccgcgacgtg gtgcaggggc acaagtactg cgagcggcac  480
gtccaccggg gccgcggccg ttcaagaaag cctgtggaag gagccccctc agcccgggcg  540
cacagcgaca gcaccgccac cgccccgccc tgcgccatcg gcttctcccc cgccggcatc  600
ctccacgcca cccacagcgc cgccgcgcgc gccacctga                        639

SEQ ID NO: 169         moltype = DNA  length = 951
FEATURE                Location/Qualifiers
source                 1..951
                       mol_type = other DNA
                       organism = Triticum aestivum
SEQUENCE: 169
atgatgctgg gagggcacgg cggcggcggc ggcggcggga ggtgcctgtt cacggcgtcg  60
cagtggcggg agctggagca ccaggcgctc atctacaagt acatggccgc cggctcgcag  120
gtgccccacg agctggtcct cccgctccgc caccgcgacg cagccttcgc cgccatcgac  180
accgcccccct ccctcgcctg ctaccctcct ccgcagccat ccctggggtg ggggctctac  240
ggggcgggat cgcagtacgc gcggaagccg gaggacccgg agcccgggcg gtgccggcgg  300
acggacggca agaaatggcg gtgctccagg gaggcgtatg ggagtccaa gtactgcgac  360
aggcacatgc accgcggcaa gaaccgttca agaaagcctg tggaaccaat gagctccgcc  420
tcctccgtct cctccccggc cgcctcgtac cgccacaccg ccctctccat gtcgcccccc  480
acgccggccg acacgcccag ctacggccac ggccacggcc acgaccacct ccgcgcagct  540
gctggtcaga gccagataaa ccctctccag ctccacctcg acaccccgtc gcccccgccg  600
tcctaccaca ggtacgcgcc ggcgcagcag tacgggggct ccttcttccc gagcaggcag  660
caggtgcagg aggaggaggc gaggcggcgg cagcacttcc tggctctcgg cgccgacctg  720
agcctggaca agccggacgc caccaccgcg gcgtcctcga caaccgagga gaagccgctg  780
cggcgcttct tcgacgagtg gccgcgcgac gggaacgccg tcgagggtag gccctggaat  840
atgggccacc gggacgagac gctgctctcc atgtccatcc ccacgacgac ggcctcgcac  900
cccgacctcg ccgccgcctc gcgctaccac caccaccaca acgatgaata a          951
```

```
SEQ ID NO: 170          moltype = DNA  length = 1227
FEATURE                 Location/Qualifiers
source                  1..1227
                        mol_type = other DNA
                        organism = Triticum aestivum
SEQUENCE: 170
atggcgatgc cgtatgcctc tctttccccg gcaggcgacc gccgctcctc cccggccgcc  60
accgccaccg cctccctcct ccccttctgc cgctcctccc ccttctccgc cggcggcaat  120
ggcggcatgg gggaggaggc gccgatggac gggaggtgga tggcgaggcc ggtgcccttc  180
acggcggcgc agtacgagga gctggagcac caggcgctca tatacaagta cctggtggcc  240
ggcgtgcccg tcccgccgga tctcgtgctc cccatccgcc gcggcatcga gtccctcgcc  300
gccccgcttct accacaaccc cctcgccatc gggtacggat cgtacctggg caagaaggtg  360
gatccggagc cgggccggtg ccggcgcacg gacggcaaga agtggcggtg cgccaaggag  420
gccgcctccg actccaagta ctgcgagcgc cacatgcacc gcggccgcaa ccgttcaaga  480
aagcctgtgg aaacgcagct cgtgccccac tcccagccgc cggccgcctc cgccgtgccg  540
cccctcgcca ccggcttcca cggccactcc ctctaccccg ccgtcggcgg cggcaccaac  600
ggtggtggag gcgggggggaa caacggcatg tccatgcccg gcacgttctc ctccgcgctg  660
gggccgcctc agcagcacat gggcaacaat gccgcctctc cctacgcggc tctcggcggc  720
gccggaacat gcaaagattt caggtatacc gcatatggaa taagatcttt ggcagatgag  780
cagagtcagc tcatgacaga agccatgaac acctccgtgg agaacccatg gcgcctgccg  840
ccatcttctc aaacgactac attcccgctc tcaagctact ctcctcagct tggagcaacg  900
agtgacctgg gtcagaacaa cagcagcaac aacaacagcg gcgtcaaggc cgagcgacag  960
cagcagcagc agccgctctc cttcccgggg tgcggcgact tcggcggcgg cgactccgcg  1020
aagcaggaga accagacgct gcggccgttc ttcgacgagt ggccgaagac gagggactcg  1080
tggtcggacc tgaccgacga caactcgaac gtcgcctcct tctcggccac ccagctgtcg  1140
atctcgatac ctatgacgtc ccccgacttc tccgccgcca gctcccagtc gcccaacggc  1200
atgctgttcg ccggcgagat gtactag                                      1227

SEQ ID NO: 171          moltype = DNA  length = 1230
FEATURE                 Location/Qualifiers
source                  1..1230
                        mol_type = other DNA
                        organism = Triticum aestivum
SEQUENCE: 171
atgatgatga tgggcggtcg cgcgggggcc ggcggcgtcg gggcaggcgg cggccggtgc  60
ccgttcacgg cgacgcagtg gcaggagctg gagcaccagg cgctcatcta caagtacatg  120
gcctccggcg tgcccatccc ctccgacctc ctcctcccgc tccgccgcag cttcctcctc  180
gactccgccc tcgccacctc cccctccctc gccttccctc cccaggccgc acttgggtgg  240
ggttgctttg gcatggggtt cggccggaag gcggaggacc cggagccggg gcggtgccgg  300
cggacggacg ggaagaagtg gcgctgctcc aaggaggcgt acccggactc caagtactgc  360
gagaagcaca tgcaccgggg caagaaccgt tcaagaaagc ctgtggaaat gtccttggcc  420
acgcccccgc cgccgccttc ctcctcggcc tcctcttcct cctccaacgt ccactccgcc  480
gtcaacgtcg ccaccaccac cacctcccca gcgccgtcct accaccgcca cgccgctgcg  540
actcacgaca cgacgcccta ccacgccctc tacggcggcc cctactcctc cgccggccgc  600
cagcagcacg ccagcgccta ccaccacgcg gcgcaggtca gcccgttcca cctgcacctc  660
gacaccaccc acccgcaccc gccgccgtcc tactactcca ccatggacca cagcaaggac  720
agctacgcct acgggcacag cgtcaaggag gtgcacggcg gcggcgagca cgccttcttc  780
tcctccgacg tcagcaccga cagggaccac caccaccatc agcaccaaca ccacgctagc  840
gccggcggca acggccagtg gcagttcaag cagctcggcg gcatggagcc caagcagcac  900
aaccccacgt cgctcttccc cggctacggc aacaacgcgg cgtacgccat cgacctgtcc  960
agcaaagaag aggacgagga gaaggagagg cggcaacagc agcagcactg cttcctgctg  1020
ggcgccgacc tgaggctcga caagccgtcg tcggggcacg gcgactccgc cgaccagaag  1080
cctctccggc cgttcttcga cgagtggccg cacgagaaga ctggcagcaa ggggtcgtgg  1140
atggggctcg agggggagac gcagctctcc atctccatcg ccaatgaact ccccatcacc  1200
accacctccc gctaccacca tggtgaatga                                    1230

SEQ ID NO: 172          moltype = DNA  length = 636
FEATURE                 Location/Qualifiers
source                  1..636
                        mol_type = other DNA
                        organism = Triticum aestivum
SEQUENCE: 172
atggccgacg agaaagaagc cgactcgctg cagccgccgt ccaagcagcc ccgcctctcc  60
tccgccgact cgaacgccgg ggcggtgacg acggcggtct cgtcgccgct gggtcttggc  120
ctcggcctgg ggctcggcgg cgatagccgt ggcgagcagc aggccttcga agcacgggca  180
gccgcggcgg cggcgaaatc ggcgctgacg ttcatgcagc agcaggagct ggagcaccag  240
gtgctcatct accgctactt cgcggcgggt gcgcccgtgc cggtgcacct cgtgctcccc  300
atctggaaga gcgtcgccgc ctcctccttc ggcccgcacc gcttcccctc cctgattggg  360
ctggggagcc tgtgcttcga ctaccggagc agcatggagc cggagcccgg gcggtgccgc  420
cgcacggacg gcaagaagtg gcggtgctcc cgcgacgtgg tgcaggggca caagtactgc  480
gagcggcacg tccaccgggg ccgcggccgt tcaagaaagc ctgtggaagg agcctccgca  540
gccccggcgc acagcggcag ccccaccaca gccccgcccc gcgccatcgg cttctccccc  600
gccggcatcc tccacgccac ccacagcgcc acctga                             636

SEQ ID NO: 173          moltype = DNA  length = 62
FEATURE                 Location/Qualifiers
source                  1..62
                        mol_type = other DNA
                        organism = Triticum aestivum
```

```
SEQUENCE: 173
cacgtccacc ggggccgcgg ccgttcaaga aagcctgtgg aaggagcctc cgcagccccg  60
gc                                                                 62

SEQ ID NO: 174         moltype = DNA  length = 62
FEATURE                Location/Qualifiers
source                 1..62
                       mol_type = other DNA
                       organism = Triticum aestivum
SEQUENCE: 174
cacatgcacc ggggcaagaa ccgttcaaga aagcctgtgg aaatgtcctt ggccacgccc  60
cc                                                                 62

SEQ ID NO: 175         moltype = DNA  length = 62
FEATURE                Location/Qualifiers
source                 1..62
                       mol_type = other DNA
                       organism = Triticum aestivum
SEQUENCE: 175
cacatgcacc gcggccgcaa ccgttcaaga aagcctgtgg aaacgcagct cgtgccccac  60
tc                                                                 62

SEQ ID NO: 176         moltype = DNA  length = 62
FEATURE                Location/Qualifiers
source                 1..62
                       mol_type = other DNA
                       organism = Triticum aestivum
SEQUENCE: 176
cacatgcacc gcggcaagaa ccgttcaaga aagcctgtgg aaccaatgag ctccgcctcc  60
tc                                                                 62

SEQ ID NO: 177         moltype = DNA  length = 62
FEATURE                Location/Qualifiers
source                 1..62
                       mol_type = other DNA
                       organism = Triticum aestivum
SEQUENCE: 177
cacgtccacc ggggccgcgg ccgttcaaga aagcctgtgg aaggagcccc ctcagcccgg  60
gc                                                                 62

SEQ ID NO: 178         moltype = DNA  length = 62
FEATURE                Location/Qualifiers
source                 1..62
                       mol_type = other DNA
                       organism = Triticum aestivum
SEQUENCE: 178
cacatgcacc gcggccgcaa ccgttcaaga aagcctgtgg aaacgcagct cgtctcccac  60
tc                                                                 62

SEQ ID NO: 179         moltype = DNA  length = 62
FEATURE                Location/Qualifiers
source                 1..62
                       mol_type = other DNA
                       organism = Triticum aestivum
SEQUENCE: 179
cacatgcacc gtggccgcaa ccgttcaaga aagcctgtgg aatccaagtc tgcttcccct  60
gc                                                                 62

SEQ ID NO: 180         moltype = DNA  length = 62
FEATURE                Location/Qualifiers
source                 1..62
                       mol_type = other DNA
                       organism = Triticum aestivum
SEQUENCE: 180
cacatgcacc gcggccgcaa ccgttcaaga aagcctgtgg aaacgcagct cgtctcgcac  60
tc                                                                 62

SEQ ID NO: 181         moltype = DNA  length = 62
FEATURE                Location/Qualifiers
source                 1..62
                       mol_type = other DNA
                       organism = Triticum aestivum
SEQUENCE: 181
cacatgcacc gcggcaagaa ccgttcaaga aagcctgtgg aaatgtcctt ggccacgccc  60
cc                                                                 62

SEQ ID NO: 182         moltype = DNA  length = 62
FEATURE                Location/Qualifiers
source                 1..62
```

```
                        mol_type = other DNA
                        organism = Triticum aestivum
SEQUENCE: 182
cacatgcacc gcggcaagaa ccgttcaaga aagcctgtgg aaccgatgtc ctcctcctcc  60
gt                                                                 62

SEQ ID NO: 183          moltype = DNA  length = 62
FEATURE                 Location/Qualifiers
source                  1..62
                        mol_type = other DNA
                        organism = Triticum aestivum
SEQUENCE: 183
cacgtccacc ggggccgcgg ccgttcaaga aagcctgtgg aaggagcccc cgcagccccg  60
gc                                                                 62

SEQ ID NO: 184          moltype = DNA  length = 62
FEATURE                 Location/Qualifiers
source                  1..62
                        mol_type = other DNA
                        organism = Triticum aestivum
SEQUENCE: 184
cacgtccacc gcggccgcgg ccgtgcaaga aagcctgtgg aagccgcgcc ggccacatca  60
gc                                                                 62

SEQ ID NO: 185          moltype = DNA  length = 62
FEATURE                 Location/Qualifiers
source                  1..62
                        mol_type = other DNA
                        organism = Triticum aestivum
SEQUENCE: 185
cacatgcacc gcggccgcaa ccgttcaaga aagcctgtgg aaacgcagct cgtcccgcac  60
ac                                                                 62

SEQ ID NO: 186          moltype = DNA  length = 62
FEATURE                 Location/Qualifiers
source                  1..62
                        mol_type = other DNA
                        organism = Triticum aestivum
SEQUENCE: 186
cacatgcacc gcggcaagaa ccgttcaaga aagcctgtgg aaatgtcctt ggccacgccc  60
cc                                                                 62

SEQ ID NO: 187          moltype = DNA  length = 62
FEATURE                 Location/Qualifiers
source                  1..62
                        mol_type = other DNA
                        organism = Triticum aestivum
SEQUENCE: 187
cacatgcacc gcggcaagaa ccgttcaaga aagcctgtgg aaccgatgag ctcctcctcc  60
gt                                                                 62

SEQ ID NO: 188          moltype = DNA  length = 62
FEATURE                 Location/Qualifiers
source                  1..62
                        mol_type = other DNA
                        organism = Triticum aestivum
SEQUENCE: 188
catatgaacc ggggacgcca tcgttcaaga aagcatgtgg aaggccagcc tggccatgcc  60
gc                                                                 62

SEQ ID NO: 189          moltype = DNA  length = 62
FEATURE                 Location/Qualifiers
source                  1..62
                        mol_type = other DNA
                        organism = Triticum aestivum
SEQUENCE: 189
cacatcaata ggaaccgcca tcgttcaaga aagcctgtgg aaaaccaaac aaggaagaac  60
gc                                                                 62

SEQ ID NO: 190          moltype = DNA  length = 62
FEATURE                 Location/Qualifiers
source                  1..62
                        mol_type = other DNA
                        organism = Triticum aestivum
SEQUENCE: 190
cacatgcacc gcggccgcaa ccgttcaaga aagcctgtgg aaacgcagct cgtcgccacg  60
cc                                                                 62

SEQ ID NO: 191          moltype = DNA  length = 62
```

```
FEATURE                Location/Qualifiers
source                 1..62
                       mol_type = other DNA
                       organism = Triticum aestivum
SEQUENCE: 191
cacatcaata ggaaccgcca tcgttcaaga aagcctgtgg aaaaccaaac aaggaagaac  60
gc                                                                  62

SEQ ID NO: 192         moltype = DNA  length = 62
FEATURE                Location/Qualifiers
source                 1..62
                       mol_type = other DNA
                       organism = Triticum aestivum
SEQUENCE: 192
cacgtccacc gcggccgcgg ccgtgcaaga aagcctgtgg aagccgcggc ggccacatca  60
gc                                                                  62

SEQ ID NO: 193         moltype = DNA  length = 62
FEATURE                Location/Qualifiers
source                 1..62
                       mol_type = other DNA
                       organism = Triticum aestivum
SEQUENCE: 193
catatgaacc ggggacgcca tcgttcaaga aagcatgtgg aaggccagcc tggccatgcc  60
gc                                                                  62

SEQ ID NO: 194         moltype = DNA  length = 62
FEATURE                Location/Qualifiers
source                 1..62
                       mol_type = other DNA
                       organism = Triticum aestivum
SEQUENCE: 194
cacatgcacc gcggccgcaa ccgttcaaga aagcctgtgg aaacgcagct cgtcgccacg  60
cc                                                                  62

SEQ ID NO: 195         moltype = DNA  length = 62
FEATURE                Location/Qualifiers
source                 1..62
                       mol_type = other DNA
                       organism = Triticum aestivum
SEQUENCE: 195
cacgtccacc gcggccgcag ccgtgcaaga aagcctgtgg aagccgcggc ggccacatca  60
gc                                                                  62

SEQ ID NO: 196         moltype = DNA  length = 62
FEATURE                Location/Qualifiers
source                 1..62
                       mol_type = other DNA
                       organism = Triticum aestivum
SEQUENCE: 196
catatgaacc ggggacgcca tcgttcaaga aagcatgtgg aaggccagcc tggccatgcc  60
gc                                                                  62

SEQ ID NO: 197         moltype = DNA  length = 62
FEATURE                Location/Qualifiers
source                 1..62
                       mol_type = other DNA
                       organism = Triticum aestivum
SEQUENCE: 197
cacatgcacc gtggccgcaa ccgttcaaga aagcctgtgg aatccaagtc tgcttcccct  60
gc                                                                  62

SEQ ID NO: 198         moltype = DNA  length = 62
FEATURE                Location/Qualifiers
source                 1..62
                       mol_type = other DNA
                       organism = Triticum aestivum
SEQUENCE: 198
cacatgcacc gtggccgcaa ccgttcaaga aagcctgtgg aatccaagtc tgcttcccct  60
gc                                                                  62

SEQ ID NO: 199         moltype = DNA  length = 22
FEATURE                Location/Qualifiers
source                 1..22
                       mol_type = genomic DNA
                       organism = Triticum aestivum
SEQUENCE: 199
ccgttcaaga aagcctgtgg aa                                            22
```

```
SEQ ID NO: 200         moltype = DNA  length = 22
FEATURE                Location/Qualifiers
source                 1..22
                       mol_type = genomic DNA
                       organism = Triticum aestivum
SEQUENCE: 200
ccgtgcaaga aagcctgtgg aa                                           22

SEQ ID NO: 201         moltype = DNA  length = 22
FEATURE                Location/Qualifiers
source                 1..22
                       mol_type = genomic DNA
                       organism = Triticum aestivum
SEQUENCE: 201
tcgttcaaga aagcatgtgg aa                                           22

SEQ ID NO: 202         moltype = DNA  length = 22
FEATURE                Location/Qualifiers
source                 1..22
                       mol_type = genomic DNA
                       organism = Triticum aestivum
SEQUENCE: 202
tcgttcaaga aagcctgtgg aa                                           22

SEQ ID NO: 203         moltype =   length =
SEQUENCE: 203
000

SEQ ID NO: 204         moltype =   length =
SEQUENCE: 204
000

SEQ ID NO: 205         moltype =   length =
SEQUENCE: 205
000

SEQ ID NO: 206         moltype = AA  length = 207
FEATURE                Location/Qualifiers
REGION                 1..207
                       note = Synthetic cytosine deaminase
source                 1..207
                       mol_type = protein
                       organism = synthetic construct
SEQUENCE: 206
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                      207

SEQ ID NO: 207         moltype = AA  length = 228
FEATURE                Location/Qualifiers
REGION                 1..228
                       note = Synthetic cytosine deaminase
source                 1..228
                       mol_type = protein
                       organism = synthetic construct
SEQUENCE: 207
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK               228

SEQ ID NO: 208         moltype = AA  length = 162
FEATURE                Location/Qualifiers
REGION                 1..162
                       note = Synthetic cytosine deaminase
source                 1..162
                       mol_type = protein
                       organism = synthetic construct
SEQUENCE: 208
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                     162

SEQ ID NO: 209         moltype = AA  length = 1763
FEATURE                Location/Qualifiers
REGION                 1..1763
                       note = Synthetic adenosine deaminase
source                 1..1763
```

```
                        mol_type = protein
                        organism = synthetic construct
SEQUENCE: 209
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTDSGGSSG GSSGSETPGT SESATPESSG GSSGGSDKKY SIGLAIGTNS VGWAVITDEY  420
KVPSKKFKVL GNTDRHSIKK NLIGALLFDS GETAEATRLK RTARRRYTRR KNRICYLQEI  480
FSNEMAKVDD SFFHRLEESF LVEEDKKHER HPIFGNIVDE VAYHEKYPTI YHLRKKLVDS  540
TDKADLRLIY LALAHMIKFR GHFLIEGDLN PDNSDVDKLF IQLVQTYNQL FEENPINASG  600
VDAKAILSAR LSKSRRLENL IAQLPGEKKN GLFGNLIALS LGLTPNFKSN FDLAEDAKLQ  660
LSKDTYDDDL DNLLAQIGDQ YADLFLAAKN LSDAILLSDI LRVNTEITKA PLSASMIKRY  720
DEHHQDLTLL KALVRQQLPE KYKEIFFDQS KNGYAGYIDG GASQEEFYKF IKPILEKMDG  780
TEELLVKLNR EDLLRKQRTF DNGSIPHQIH LGELHAILRR QEDFYPFLKD NREKIEKILT  840
FRIPYYVGPL ARGNSRFAWM TRKSEETITP WNFEEVVDKG ASAQSFIERM TNFDKNLPNE  900
KVLPKHSLLY EYFTVYNELT KVKYVTEGMR KPAFLSGEQK KAIVDLLFKT NRKVTVKQLK  960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 210          moltype = AA  length = 1565
FEATURE                 Location/Qualifiers
REGION                  1..1565
                        note = Synthetic adenosine deaminase
source                  1..1565
                        mol_type = protein
                        organism = synthetic construct
SEQUENCE: 210
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 211          moltype = AA  length = 1565
FEATURE                 Location/Qualifiers
REGION                  1..1565
                        note = Synthetic adenosine deaminase
source                  1..1565
                        mol_type = protein
                        organism = synthetic construct
SEQUENCE: 211
SEVEFSHEYW MRHALTLAKR ARDEREVPVG AVLVLNNRVI GEGWNRAIGL HDPTAHAEIM  60
```

```
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                            1565

SEQ ID NO: 212          moltype = AA  length = 364
FEATURE                 Location/Qualifiers
REGION                  1..364
                        note = Synthetic adenosine deaminase
source                  1..364
                        mol_type = protein
                        organism = synthetic construct
SEQUENCE: 212
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                             364

SEQ ID NO: 213          moltype = AA  length = 167
FEATURE                 Location/Qualifiers
REGION                  1..167
                        note = Synthetic adenosine deaminase
source                  1..167
                        mol_type = protein
                        organism = synthetic construct
SEQUENCE: 213
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                167

SEQ ID NO: 214          moltype = AA  length = 1228
FEATURE                 Location/Qualifiers
REGION                  1..1228
                        note = Lachnospiraceae bacterium
source                  1..1228
                        mol_type = protein
                        organism = unidentified
SEQUENCE: 214
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
```

```
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                     1228

SEQ ID NO: 215          moltype = AA  length = 1307
FEATURE                 Location/Qualifiers
source                  1..1307
                        mol_type = protein
                        organism = Acidaminococcus sp.
SEQUENCE: 215
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 216          moltype = AA  length = 1241
FEATURE                 Location/Qualifiers
source                  1..1241
                        mol_type = protein
                        organism = Butyrivibrio proteoclasticus
SEQUENCE: 216
MLLYENYTKR NQITKSLRLE LRPQGKTLRN IKELNLLEQD KAIYALLERL KPVIDEGIKD  60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KFKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                      1241

SEQ ID NO: 217          moltype = AA  length = 1238
FEATURE                 Location/Qualifiers
source                  1..1238
                        mol_type = protein
                        organism = Methanoplasma termitum
SEQUENCE: 217
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
```

```
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                          1238

SEQ ID NO: 218          moltype = AA  length = 1281
FEATURE                 Location/Qualifiers
source                  1..1281
                        mol_type = protein
                        organism = Eubacterium eligens
SEQUENCE: 218
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                            1281

SEQ ID NO: 219          moltype = AA  length = 1300
FEATURE                 Location/Qualifiers
source                  1..1300
                        mol_type = protein
                        organism = Francisella tularensis
SEQUENCE: 219
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 220          moltype = AA  length = 1206
FEATURE                 Location/Qualifiers
REGION                  1..1206
                        note = Lachnospiraceae bacterium
source                  1..1206
                        mol_type = protein
                        organism = unidentified
SEQUENCE: 220
MYYESLTKQY PVSKTIRNEL IPIGKTLDNI RQNNILESDV KRKQNYEHVK GILDEYHKQL  60
```

-continued

```
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 221         moltype = AA  length = 1233
FEATURE                Location/Qualifiers
REGION                 1..1233
                       note = Lachnospiraceae bacterium
source                 1..1233
                       mol_type = protein
                       organism = unidentified
SEQUENCE: 221
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                                1233

SEQ ID NO: 222         moltype = AA  length = 1227
FEATURE                Location/Qualifiers
REGION                 1..1227
                       note = Lachnospiraceae bacterium
source                 1..1227
                       mol_type = protein
                       organism = unidentified
SEQUENCE: 222
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
```

```
AEDEKLDKVK IASNKEWLEY AQTSVKH                                    1227

SEQ ID NO: 223         moltype = AA  length = 1264
FEATURE                Location/Qualifiers
source                 1..1264
                       mol_type = protein
                       organism = Leptospira inadai
SEQUENCE: 223
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                             1264

SEQ ID NO: 224         moltype = AA  length = 1373
FEATURE                Location/Qualifiers
source                 1..1373
                       mol_type = protein
                       organism = Moraxella bovoculi
SEQUENCE: 224
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR        1373

SEQ ID NO: 225         moltype = AA  length = 1352
FEATURE                Location/Qualifiers
source                 1..1352
                       mol_type = protein
                       note = Parcubacteria bacterium
                       organism = unidentified
SEQUENCE: 225
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
```

```
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 226          moltype = AA  length = 1260
FEATURE                 Location/Qualifiers
source                  1..1260
                        mol_type = protein
                        organism = Porphyromonas crevioricanis
SEQUENCE: 226
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 227          moltype = AA  length = 1324
FEATURE                 Location/Qualifiers
source                  1..1324
                        mol_type = protein
                        organism = Prevotella disiens
SEQUENCE: 227
MENYQEFTNL FQLNKTLRFE LKPIGKTCEL LEEGKIFASG SFLEKDKVRA DNVSYVKKEI  60
DKKHKIFIEE TLSSFSISND LLKQYFDCYN ELKAFKKDCK SDEEEVKKTA LRNKCTSIQR  120
AMREAISQAF LKSPQKKLLA IKNLIENVFK ADENVQHFSE FTSYFSGFET NRENFYSDEE  180
KSTSIAYRLV HDNLPIFIKN IYIFEKLKEQ FDAKTLSEIF ENYKLYVAGS SLDEVFSLEY  240
FNNTLTQKGI DNYNAVIGKI VKEDKQEIQG LNEHINLYNQ KHKDRRLPFF ISLKKQILSD  300
REALSWLPDM FKNDSEVIDA LKGFYIEDGF ENNVLTPLAT LLSSLDKYNL NGIFIRNNEA  360
LSSLSQNVYR NFSIDEAIDA QNAELQTFNN YELIANALRA KIKKETKQGR KSFEKYEEYI  420
DKKVKAIDSL SIQEINELVE NYVSEFNSNS GNMPRKVEDY FSLMRKGDFG SNDLIENIKT  480
KLSAAEKLLG TKYQETAKDI FKKDENSKLI KELLDATKQF QHFIKPLLGT GEEADRDLVF  540
YGDFLPLYEK FEELTLLYNK VRNRLTQKPY SKDKIRLCFN KPKLMTGWVD SKTEKSDNGT  600
QYGGYLFRKK NEIGEYDYFL GISSKAQLFR KNEAVIGDYE RLDYYQPKAN TIYGSAYEGE  660
NSYKEDKKRL NKVIIAYIEQ IKQTNIKKSI IESISKYPNI SDDDKVTPSS LLEKIKKVSI  720
DSYNGILSFK SFQSVNKEVI DNLLKTISPL KNKAEFLDLI NKDYQIFTEV QAVIDEICKQ  780
KTFIYFPISN VELEKEMGDK DKPLCLFQIS NKDLSFAKTF SANLRKKRGA ENLHTMLFKA  840
LMEGNQDNLD LGSGAIFYRA KSLDGNKPTH PANEAIKCRN VANKDKVSLF TYDIYKNRRY  900
MENKFLFHLS IVQNYKAAND SAQLNSSATE YIRKADDLHI IGIDRGERNL LYYSVIDMKG  960
NIVEQDSLNI IRNNDLETDY HDLLDKREKE RKANRQNWEA VEGIKDLKKG YLSQAVHQIA  1020
QLMLKYNAII ALEDLGQMFV TRGQKIEKAV YQQFEKSLVD KLSYLVDKKR PYNELGGILK  1080
AYQLASSITK NNSDKQNGFL FYVPAWNTSK IDPVTGFTDL LRPKAMTIKE AQDFFGAFDN  1140
ISYNDKGYFE FETNYDKFKI RMKSAQTRWT ICTFGNRIKR KKDKNYWNYE EVELTEEFKK  1200
LFKDSNIDYE NCNLKEEIQN KDNRKFFDDL IKLLQLTLQM RNSDDKGNDY IISPVANAEG  1260
QFFDSRNGDK KLPLDADANG AYNIARKGLW NIRQIKQTKN KDDLNLSISS TEWLDFVREK  1320
PYLK                                                              1324

SEQ ID NO: 228          moltype = AA  length = 1484
FEATURE                 Location/Qualifiers
source                  1..1484
                        mol_type = protein
                        note = Peregrinibacteria bacterium
                        organism = unidentified
SEQUENCE: 228
MSNFFKNFTN LYELSKTLRF ELKPVGDTLT NMKDHLEYDE KLQTFLKDQN IDDAYQALKP  60
```

```
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 229          moltype = AA  length = 1245
FEATURE                 Location/Qualifiers
source                  1..1245
                        mol_type = protein
                        organism = Porphyromonas macacae
SEQUENCE: 229
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                 1245

SEQ ID NO: 230          moltype = AA  length = 1250
FEATURE                 Location/Qualifiers
source                  1..1250
                        mol_type = protein
                        organism = Smithella sp.
SEQUENCE: 230
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
```

-continued

```
PKNADANGAY HIALKGLWCL EQISKTDDLK KVKLAISNKE WLEFVQTLKG           1250

SEQ ID NO: 231         moltype = AA  length = 3987
FEATURE                Location/Qualifiers
REGION                 1..3987
                       note = Synthetic Cas12a
source                 1..3987
                       mol_type = protein
                       organism = synthetic construct
SEQUENCE: 231
ATGGCCGGGA GCAAGAAGCG CCGGATAAAG CAGGACACGC AGTTCGAGGG CTTCACCAAC  60
CTGTACCAAG TCTCCAAGAC GCTCCGGTTC GAGCTTATCC CGCAAGGGAA GACCCTGAAA  120
CACATCCAGG AACAAGGTTT CATCGAGGAG GACAAGGCCC GCAACGACCA CTACAAGGAG  180
CTCAAGCCCA TAATCGATCG GATCTACAAG ACGTACGCCG ACCAGTGCCT CCAACTGGTG  240
CAGCTCGACT GGGAGAACCT GAGCGCCGCC ATTGACAGCT ACCGCAAGGA AAAGACGGAG  300
GAGACGCGCA ACGCCCTTAT TGAGGAGCAA GCCACCTACC GCAACGCCAT CCACGACTAC  360
TTCATCGGGC GCACCGACAA CCTGACGGAC GCGATCAACA AGCGCCACGC GGAAATCTAC  420
AAGGGCCTTT TCAAGGCCGA GCTCTTCAAC GGGAAGGTCC TAAAACAGCT CGGGACTGTC  480
ACGACAACCG AGCATGAGAA CGCCCTCCTT CGCAGCTTCG ACAAGTTCAC CACATACTTC  540
TCGGGCTTCT ACCGGAACCG CAAGAACGTT TTCAGCGCCG AGGACATCTC CACCGCCATC  600
CCGCACAGGA TCGTCCAGGA CAACTTCCCC AAGTTCAAGG AGAACTGCCA CATCTTCACG  660
CGCCTGATTA CAGCCGTACC TTCACTTCGT GAGCACTTCG AGAACGTCAA AAAGGCCATC  720
GGGATCTTCG TCTCCACGTC CATCGAGGAG GTATTCTCTT TCCCGTTCTA TAACCAGCTC  780
CTGACCCAGA CGCAGATCGA CCTCTACAAC CAGCTACTGG GCGGCATCAG CCGGGAGGCC  840
GGGACCGAGA AAATAAAGGG CCTCAACGAA GTTCTCAACC TGGCCATCCA GAAGAACGAC  900
GAGACCGCGC ATATCATCGC ATCCCTGCCG CATCGCTTCA TTCCTTTGTT CAAGCAGATA  960
TTGAGCGACC GGAACACCCT CTCGTTCATC CTCGAAGAAT TCAAGAGCGA CGAGGAGGTC  1020
ATTCAGTCTT TCTGCAAGTA CAAGACGCTC CTACGGAATG AGAATGTGCT GGAGACCGCG  1080
GAGGCACTCT TCAATGAGCT GAACTCCATT GACCTGACCC ACATCTTCAT TAGCCACAAG  1140
AAACTGGAGA CGATCTCCAG CGCCCTGTGC GACCACTGGG ACACTCTCCG CAACGCCCTC  1200
TACGAACGCC GGATCTCCGA ACTTACCGGC AAGATAACTA AGTCGGCTAA GGAGAAGGTG  1260
CAACGGAGCC TCAAGCACGA GGACATCAAC CTTCAGGAAA TCATCTCAGC CGCGGGCAAG  1320
GAGCTGAGCG AGGCGTTTAA GCAGAAAACA TCGGAGATAC TGAGCCACGC GCACGCGGCC  1380
CTGGATCAAC CGCTGCCGAC GACTCTCAAG AAGCAAGAGG AGAAGGAAAT CCTTAAGTCC  1440
CAGCTCGACT CGCTGCTCGG CCTCTATCAC TTGCTCGACT GGTTCGCGGT TGATGAGTCC  1500
AACGAGGTGG ACCCGGAGTT CTCCGCGCGC CTCACGGGTA TTAAGCTGGA GATGGAGCCA  1560
AGCTTAAGCT TCTACAACAA GGCCCGCAAC TACGCGACCA AAAAACCGTA CTCAGTCGAG  1620
AAATTCAAGC TGAATTTCCA GATGCCTACA TTGGCGAGGG GGTGGGACGT GAACCGCGAG  1680
AAGAACAATG GAGCCATCCT GTTCGTCAAA AATGGGTTGT ACTACCTGGG CATCATGCCC  1740
AAGCAGAAGG GCCGTTACAA GGCCCTGTCA TTCGAGCCTA CCGAGAAGAC CTCGGAGGGC  1800
TTCGACAAGA TGTACTACGA CTATTTCCCG GACGCCGCCA AGATGATCCC GAAGTGCTCC  1860
ACGCAGCTCA AAGCCGTCAC GGCCCACTTC CAGACGCATA CCACGCCGAT ACTTCTGAGC  1920
AACAACTTCA TTGAGCCGCT AGAGATCACG AAGGAGATAT ACGACCTAAA CAACCCCGAA  1980
AAGGAGCCCA AGAAGTTCCA GACAGCCTAC GCTAAGAAGA CAGGTGATCA GAAGGGATAT  2040
AGGGAGGCAC TCTGCAAGTG GATCGACTTC ACGCGCGACT TCCTGTCGAA ATATACAAAG  2100
ACGACCAGCA TTGACCTAAG TTCTCTCCGC CCATCCTCCC AGTACAAGGA TCTGGGCGAG  2160
TATTATGCGG AGCTGAACCC ATTGCTGTAC CACATCAGCT TCCAGAGGAT CGCCGAGAAG  2220
GAGATTATGG ACGCGGTGGA GACGGGGAAA CTATACCTGT TCCAAATATA TAACAAGGAC  2280
TTCGCTAAAG GGCACCACGG GAAGCCCAAC CTGCACACAC TCTACTGGAC GGGCTTGTTT  2340
TCGCCAGAAA ATTTGGCCAA GACTTCGATC AAGCTCAACG GCCAGGCGGA GTTGTTTTAC  2400
CGTCCCAAGT CTCGCATGAA GCGCATGGCG CATCGCCTCG GAGAGAAAAT GCTTAACAAG  2460
AAGCTCAAGG ATCAGAAGAC GCCCATACCT GATACGTTGT ACCAGGAATT GTACGACTAC  2520
GTGAACCACC GCCTATCGCA CGACCTCTCA GACGAGGCCC GCGCCCTCCT CCCAAACGTG  2580
ATTACTAAGG AGGTTTCCCA TGAAATAATC AAGGACCGAC GGTTCACCAG CGACAAATTT  2640
TTTTTCCACG TGCCTATCAC GCTCAATTAC CAGGCGGCCA ACTCCCCATC GAAGTTCAAC  2700
CAGCGCGTGA ACGCCTACCT TAAGGAGCAC CCGGAGACCC CAATCATCGG GATCGACCGT  2760
GGCGAGCGGA ACCTGATCTA TATTACGGTG ATCGATAGCA CCGGGAAGAT CCTGGAGCAG  2820
CGCTCCCTGA ACACAATCCA GCAGTTTGAC TACCAGAAGA AACTCGACAA CCGGGAGAAG  2880
GAGCGCGTCG CAGCCCGGCA AGCATGGAGT GTGGTCGGCA CCATAAAGGA CCTGAAACAG  2940
GGTTACCTAA GTCAAGTTAT CCACGAGATC GTTGACCTGA TGATACACTA TCAAGCCGTA  3000
GTCGTGCTGG AGAACCTCAA CTTCGGGTTT AAGTCCAAGC GCACCGGCAT CGCGGAGAAG  3060
GCGGTGTACC AGCAGTTCGA GAAGATGCTG ATCGACAAGC TGAACTGCCT GGTGCTCAAG  3120
GACTACCCTG CGGAGAAGGT CGGCGGGGTC TTGAACCCGT ACCAGCTAAC CGACCAGTTC  3180
ACGAGCTTCG CCAAAATGGG CACGCAGTCC GGATTCTTGT TTTATGTCCC GGCTCCATAT  3240
ACAAGTAAGA TCGACCCGCT GACAGGGTTT GTTGACCCAT TCGTGTGGAA GACCATCAAG  3300
AACCACGAGA GCAGGAAACA CTTCTTAGAG GGCTTCGACT TCCTGCATTA CGACGTTAAG  3360
ACAGGCGACT TCATCCTGCA CTTCAAGATG AACCGCAACC TGTCGTTCCA GAGGGGCCTG  3420
CCCGGCTTCA TGCCCGCCTG GGATATCGTC TTTGAGAAGA ATGAGACGCA GTTCGACGCG  3480
AAGGGGACGC CGTTCATCGC TGGAAAGCGG ATCGTGCCGG TCATCGAGAA CCACCGCTTC  3540
ACGGGTCGCT ACCGAGATTT ATACCCCGCC AACGAACTAA TTGCGCTGCT GGAGGAGAAG  3600
GGGATCGTGT TCCGAGATGG CAGCAACATT CTCCCGAAGC TGCTGGAGAA CGACGACTCG  3660
CACGCTATTG ACACGATGGT CGCCCTCATA CGGAGCGTGC TTCAGATGCG GAACAGTAAC  3720
GCTGCCACGG GCGAGGACTA CATTAACTCC CCCGTCCGCG ACCTCAACGG GGTCTGCTTC  3780
GATAGCCGCT TCCAGAACCC GGAGTGGCCT ATGGATGCGG ACGCGAACGG GGCCTACCAC  3840
ATCGCCCTCA AGGGCCAACT CCTGCTCAAC CACTTGAAGG AAAGCAAAGA CCTCAAATTG  3900
CAGAATGGCA TCAGTAACCA GGACTGGCTC GCGTACATCC AGGAACTGAG AAACGGGTCC  3960
AAGAAGCGGC GTATCAAGCA AGATTGA                                     3987

SEQ ID NO: 232         moltype = DNA  length = 3987
```

FEATURE Location/Qualifiers
misc_feature 1..3987
note = Synthetic Cas12a
source 1..3987
mol_type = other DNA
organism = synthetic construct
SEQUENCE: 232

```
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg ggagagaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                     3987
```

SEQ ID NO: 233 moltype = DNA length = 3987
FEATURE Location/Qualifiers
misc_feature 1..3987
note = Synthetic Cas12a

```
source                  1..3987
                        mol_type = other DNA
                        organism = synthetic construct
SEQUENCE: 233
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
cgactcatta ctgctgtacc gtcgttacgc gaacacttcg agaacgtcaa gaaggcaatt  720
ggaatcttcg tctctacgtc aatagaggag gtgttcagct tcccttttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                    3987

SEQ ID NO: 234          moltype = AA  length = 1367
FEATURE                 Location/Qualifiers
REGION                  1..1367
                        note = Synthetic nCas9
source                  1..1367
                        mol_type = protein
                        organism = synthetic construct
```

```
SEQUENCE: 234
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD              1367

SEQ ID NO: 235          moltype = AA  length = 1367
FEATURE                 Location/Qualifiers
REGION                  1..1367
                        note = Synthetic enCas9
source                  1..1367
                        mol_type = protein
                        organism = synthetic construct
SEQUENCE: 235
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD              1367

SEQ ID NO: 236          moltype = DNA  length = 4101
FEATURE                 Location/Qualifiers
misc_feature            1..4101
                        note = Cas9 nucleotide sequence
source                  1..4101
                        mol_type = genomic DNA
                        organism = unidentified
SEQUENCE: 236
gacaagaagt acagcatcgg gctggcgatc gggaccaact ccgtcggctg ggctgtgatt  60
accgacgagt acaaggtgcc atccaagaag ttcaaggtcc tcggcaacac tgaccggcac  120
agcattaaga agaacctgat tggggcgctg ctgttcgatt cgggggagac tgcggaggcg  180
accaggctga agcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca tacaaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
```

```
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg ggaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
ctgagccgga agctgatcaa cggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagagaa tattgtcatc  2280
gagatggcgc gggagaatca gaccacacag aaggggcaga agaactcacg ggagcggatg  2340
aagcgcatcg aggagggcat caaggagctg gggtcgcaga tcctgaagga gcatcccgtg  2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacaggggag attgtctggg ataagggggcg ggatttcgcg  3240
accgtccgga aggtcctgtc gatgccccag gttaatattg tcaagaagac tgaggtccag  3300
actggcggct tctcaaagga gtcgattctc ccaaagagga actccgataa gctcattgct  3360
cggaagaagg attgggaccc caagaagtac gggggattcg actcccccac tgttgcttac  3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tggcggaag cggatgctgg cgtccgcggg ggagctgcaa  3660
aaggggaacg agctggcgct cccctccaag tatgtgaact tcctctacct ggcgtcgcac  3720
tacgagaagc tgaagggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                            4101

SEQ ID NO: 237         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 237
gacaagaagt actccattgg cctggcgatt gggacaaact cggtggggtg ggccgtgatt  60
acggatgagt acaaggttcc aagcaagaag ttcaaggtcc tcgggaacac agatcggcat  120
tcgattaaga agaatctcat tggggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag ggggacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
```

```
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctgggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cggcatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcaccccgtg  2400
gagaataccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac ggggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cgggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                            4101

SEQ ID NO: 238         moltype = DNA  length = 4092
FEATURE                Location/Qualifiers
misc_feature           1..4092
                       note = Cas9 nucleotide sequence
source                 1..4092
                       mol_type = genomic DNA
                       organism = unidentified
SEQUENCE: 238
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag ggggatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
```

```
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg ggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccaggggga ctcactccac  2160
gagcatattg ccaatctggc cggctctcca gctatcaaga agggcatcct gcaaacagtt  2220
aaggttgttg acgagctggt taaggtcatg ggcggcata agcccgagaa cattgtcatc  2280
gagatggctc gggagaacca gacaactcag aagggccaga agaactccag ggagcgcatg  2340
aagcggattg aggagggcat taaggagctg ggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
tactggaggc agctcctgaa tgcgaagctg atcactcaga ggaagttcga caatctgaca  2700
aaggcggaga ggggcgggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                      4092
```

```
SEQ ID NO: 239          moltype = DNA  length = 4101
FEATURE                 Location/Qualifiers
misc_feature            1..4101
                        note = Cas9 nucleotide sequence
source                  1..4101
                        mol_type = genomic DNA
                        organism = unidentified
SEQUENCE: 239
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
```

```
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cgggcgcaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                            4101

SEQ ID NO: 240         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 240
gacaagaagt acagtattgg attggccatc gggacgaaca gcgtgggctg ggccgtcatc  60
accgacgagt acaaggtgcc atccaagaag tttaaggttc tggggaatac cgaccgccac  120
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccacccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
```

```
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cggcggaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccac ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101

SEQ ID NO: 241         moltype = DNA  length = 4092
FEATURE                Location/Qualifiers
misc_feature           1..4092
                       note = Cas9 nucleotide sequence
source                 1..4092
                       mol_type = genomic DNA
                       organism = unidentified
SEQUENCE: 241
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
```

```
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aaggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg gggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                       4092

SEQ ID NO: 242         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 242
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
```

```
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttttg agttggaaaa cggcagaaag agaatgttgg ccagtgccgg ggagcttcaa  3660
aagggcaacg aactggctct gcctagcaaa tatgtgaact tttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                            4101

SEQ ID NO: 243         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 243
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
```

```
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gataggaaa gccactgcaa aatatttctt ttatagcaat  3120
atcatgaatt tctttaagac agaaatcaca ctggccaatg ggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                           4101

SEQ ID NO: 244         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 244
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
```

```
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                          4101
```

```
SEQ ID NO: 245          moltype = DNA  length = 3307
FEATURE                 Location/Qualifiers
misc_feature            1..3307
                        note = Cas9 nucleotide sequence
source                  1..3307
                        mol_type = genomic DNA
                        organism = unidentified
SEQUENCE: 245
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atattttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
```

```
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                            3307

SEQ ID NO: 246          moltype = DNA  length = 4101
FEATURE                 Location/Qualifiers
misc_feature            1..4101
                        note = Cas9 nucleotide sequence
source                  1..4101
                        mol_type = genomic DNA
                        organism = unidentified
SEQUENCE: 246
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg ggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
ataggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
```

```
aaggtggtgg acgagcttgt caaggtgatg ggcgacacaa agcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101
```

```
SEQ ID NO: 247         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 247
gacaagaagt acagcatcgg cctggacatc ggcaccaact ctgtgggctg ggccgtgatc  60
accgacgagt acaaggtgcc cagcaagaaa ttcaaggtgc tgggcaacac cgaccggcac  120
agcatcaaga agaacctgat cggagccctg ctgttcgaca gcggcgaaac agccgaggcc  180
acccggctga agagaaccgc cagaagaaga tacaccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcaccccat cttcggcaac  360
atcgtggacg aggtggccta ccacgagaag taccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
ctggaaaatc tgatcgccca gctgcccggc gagaagaaga atggcctgtt cggaaacctg  720
attgccctga gcctgggcct gacccccaac ttcaagagca acttcgacct ggccgaggat  780
gccaaactgc agctgagcaa ggacacctac gacgacgacc tggacaacct gctggcccag  840
atcggcgacc agtacgccga cctgtttctg gccgccaaga acctgtccga cgccatcctg  900
ctgagcgaca tcctgagagt gaacaccgag atcaccaagg ccccccctgag cgcctctatg  960
atcaagagat acgacgagca ccaccaggac ctgaccctgc tgaaagctct cgtgcggcag  1020
cagctgcctg agaagtacaa agagattttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct tcgacaacgg cagcatcccc caccagatcc acctgggaga gctgcacgcc  1260
attctgcggc ggcaggaaga tttttaccca ttcctgaagg acaaccggga aaagatcgag  1320
aagatcctga ccttccgcat cccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga gaaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca agcccgagaa catcgtgatc  2280
```

```
gaaatggcca gagagaacca gaccacccag aagggacaga agaacagccg cgagagaatg  2340
aagcggatcg aagagggcat caaagagctg ggcagccaga tcctgaaaga acaccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctaagctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact ttttcaagac cgagattacc ctggccaacg gcgagatccg gaagcggcct  3180
ctgatcgaga caaacggcga aaccggggag atcgtgtggg ataagggccg ggattttgcc  3240
accgtgcgga aagtgctgag catgccccaa gtgaatatcg tgaaaaagac cgaggtgcag  3300
acaggcggct tcagcaaaga gtctatcctg cccaagagga acagcgataa gctgatcgcc  3360
agaaagaagg actgggaccc taagaagtac ggcggcttcg acagccccac cgtggcctat  3420
tctgtgctgg tggtggccaa agtggaaaag ggcaagtcca agaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga aacagctgtt tgtggaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca agtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggtga c                                            4101
```

```
SEQ ID NO: 248         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 248
gacaagaagt acagcatcgg cctggacatc ggcaccaact ctgtgggctg ggccgtgatc  60
accgacgagt acaaggtgcc cagcaagaaa ttcaaggtgc tgggcaacac cgaccggcac  120
agcatcaaga agaacctgat cggagccctg ctgttcgaca gcggcgaaac agccgaggcc  180
acccggctga agagaaccgc cagaagaaga tacaccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcaccccat cttcggcaac  360
atcgtggacg aggtggccta ccacgagaag taccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
ctggaaaatc tgatcgccca gctgcccggc gagaagaaga atggcctgtt cggaaacctg  720
attgccctga gcctgggcct gacccccaac ttcaagagca acttcgacct ggccgaggat  780
gccaaactgc agctgagcaa ggacacctac gacgacgacc tggacaacct gctggcccag  840
atcggcgacc agtacgccga cctgtttctg gccgccaaga acctgtccga cgccatcctg  900
ctgagcgaca tcctgagagt gaacaccgag atcaccaagg ccccccctgag cgcctctatg  960
atcaagagat acgacgagca ccaccaggac ctgaccctgc tgaaagctct cgtgcggcag  1020
cagctgcctg agaagtacaa agagattttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct tcgacaacgg cagcatcccc caccagatcc acctgggaga gctgcacgcc  1260
attctgcggc ggcaggaaga tttttaccca ttcctgaagg acaaccggga aaagatcgag  1320
aagatcctga ccttccgcat cccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga gaaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca agcccgagaa catcgtgatc  2280
gaaatggcca gagagaacca gaccacccag aagggacaga agaacagccg cgagagaatg  2340
```

```
aagcggatcg aagagggcat caaagagctg ggcagccaga tcctgaaaga acaccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctggc cgacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctgccctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact ttttcaagac cgagattacc ctggccaacg gcgagatccg gaaggcccct  3180
ctgatcgaga caaacggcga aaccggggag atcgtgtggg ataagggccg ggattttgcc  3240
accgtgcgga aagtgctgag catgccccaa gtgaatatcg tgaaaaagac cgaggtgcag  3300
acaggcggct tcagcaaaga gtctatcctg cccaagagga acagcgataa gctgatcgcc  3360
agaaagaagg actgggaccc taagaagtac ggcggcttcg acagccccac cgtggcctat  3420
tctgtgctgg tggtggccaa agtggaaaag ggcaagtcca agaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga aacagctgtt tgtggaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca agtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggtga c                                           4101
```

```
SEQ ID NO: 249         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 249
gacaagaagt acagcatcgg cctggccatc ggcaccaact ctgtgggctg ggccgtgatc  60
accgacgagt acaaggtgcc cagcaagaaa ttcaaggtgc tgggcaacac cgaccggcac  120
agcatcaaga agaacctgat cggagccctg ctgttcgaca gcggcgaaac agccgaggcc  180
acccggctga agagaaccgc cagaagaaga tacaccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcaccccat cttcggcaac  360
atcgtggacg aggtggccta ccacgagaag taccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
ctggaaaatc tgatcgccca gctgcccggc gagaagaaga atggcctgtt cggaaacctg  720
attgccctga gcctgggcct gacccccaac ttcaagagca acttcgacct ggccgaggat  780
gccaaactgc agctgagcaa ggacacctac gacgacgacc tggacaacct gctggcccag  840
atcggcgacc agtacgccga cctgtttctg gccgccaaga acctgtccga cgccatcctg  900
ctgagcgaca tcctgagagt gaacaccgag atcaccaagg ccccccctgag cgcctctatg  960
atcaagagat acgacgagca ccaccaggac ctgaccctgc tgaaagctct cgtgcggcag  1020
cagctgcctg agaagtacaa agagattttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct tcgacaacgg cagcatcccc caccagatcc acctgggaga gctgcacgcc  1260
attctgcggc ggcaggaaga tttttaccca ttcctgaagg acaaccggga aaagatcgag  1320
aagatcctga ccttccgcat cccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga gaaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca agcccgagaa catcgtgatc  2280
gaaatggcca gagagaacca gaccacccag aagggacaga agaacagccg cgagagaatg  2340
aagcggatcg aagagggcat caaagagctg ggcagccaga tcctgaaaga acaccccgtg  2400
```

```
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctaagctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact tttcaagac cgagattacc ctggccaacg gcgagatccg gaagcggcct  3180
ctgatcgaga caaacggcga aaccggggag atcgtgtggg ataagggccg ggattttgcc  3240
accgtgcgga aagtgctgag catgccccaa gtgaatatcg tgaaaaagac cgaggtgcag  3300
acaggcggct tcagcaaaga gtctatcctg cccaagagga acagcgataa gctgatcgcc  3360
agaaagaagg actgggaccc taagaagtac ggcggcttcg acagccccac cgtggcctat  3420
tctgtgctgg tggtggccaa agtggaaaag ggcaagtcca agaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc cccgaggat aatgagcaga aacagctgtt tgtggaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca agtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggtga c                                             4101

SEQ ID NO: 250         moltype = DNA  length = 4101
FEATURE                Location/Qualifiers
misc_feature           1..4101
                       note = Cas9 nucleotide sequence
source                 1..4101
                       mol_type = genomic DNA
                       organism = unidentified
SEQUENCE: 250
gacaagaagt acagcatcgg cctggacatc ggcaccaact ctgtgggctg ggccgtgatc  60
accgacgagt acaaggtgcc cagcaagaaa ttcaaggtgc tgggcaacac cgaccggcac  120
agcatcaaga agaacctgat cggagccctg ctgttcgaca gcggcgaaac agccgaggcc  180
acccggctga agagaaccgc cagaagaaga tacaccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcaccccat cttcggcaac  360
atcgtggacg aggtggccta ccacgagaag taccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
ctggaaaatc tgatcgccca gctgcccggc gagaagaaga atggcctgtt cggaaacctg  720
attgccctga gcctgggcct gacccccaac ttcaagagca acttcgacct ggccgaggat  780
gccaaactgc agctgagcaa ggacacctac gacgacgacc tggacaacct gctggcccag  840
atcggcgacc agtacgccga cctgtttctg gccgccaaga acctgtccga cgccatcctg  900
ctgagcgaca tcctgagagt gaacaccgag atcaccaagg cccccctgag cgcctctatg  960
atcaagagat acgacgagca ccaccaggac ctgaccctgc tgaaagctct cgtgcggcag  1020
cagctgcctg agaagtacaa agagattttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct tcgacaacgg cagcatcccc caccagatcc acctgggaga gctgcacgcc  1260
attctgcggc ggcaggaaga tttttaccca ttcctgaagg acaaccggga aaagatcgag  1320
aagatcctga ccttccgcat cccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga gaaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca agcccgagaa catcgtgatc  2280
gaaatggcca gagagaacca gaccacccag aagggacaga agaacagccg cgagagaatg  2340
aagcggatcg aagagggcat caaagagctg ggcagccaga tcctgaaaga acaccccgtg  2400
gaaaacaccc agctgcagaa cgagaagctg tacctgtact acctgcagaa tgggcgggat  2460
```

```
atgtacgtgg accaggaact ggacatcaac cggctgtccg actacgatgt ggacgccatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctaagctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact ttttcaagac cgagattacc ctggccaacg gcgagatccg gaagcggcct  3180
ctgatcgaga caaacggcga aaccggggag atcgtgtggg ataagggccg ggattttgcc  3240
accgtgcgga aagtgctgag catgccccaa gtgaatatcg tgaaaaagac cgaggtgcag  3300
acaggcggct tcagcaaaga gtctatcctg cccaagagga acagcgataa gctgatcgcc  3360
agaaagaagg actgggaccc taagaagtac ggcggcttcg acagccccac cgtggcctat  3420
tctgtgctgg tggtggccaa agtggaaaag ggcaagtcca agaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga aacagctgtt tgtggaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca agtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggtga c                                            4101

SEQ ID NO: 251         moltype = DNA  length = 23
FEATURE                Location/Qualifiers
misc_feature           1..23
                       note = Synthetic spacer
source                 1..23
                       mol_type = other DNA
                       organism = synthetic construct
SEQUENCE: 251
tgattccaca ggctttcttg aac                                          23

SEQ ID NO: 252         moltype = DNA  length = 26
FEATURE                Location/Qualifiers
misc_feature           1..26
                       note = Synthetic binding site of GRF5
source                 1..26
                       mol_type = other DNA
                       organism = synthetic construct
SEQUENCE: 252
aaccgttcaa gaaagcctgt ggaacg                                       26

SEQ ID NO: 253         moltype = AA  length = 8
FEATURE                Location/Qualifiers
source                 1..8
                       mol_type = protein
                       organism = Zea mays
SEQUENCE: 253
NRSRKPVE                                                           8

SEQ ID NO: 254         moltype = DNA  length = 27
FEATURE                Location/Qualifiers
source                 1..27
                       mol_type = genomic DNA
                       organism = Zea mays
SEQUENCE: 254
aaccgttcaa gaaagcctgt ggaaacg                                      27

SEQ ID NO: 255         moltype = AA  length = 9
FEATURE                Location/Qualifiers
REGION                 1..9
                       note = Mutant GRF miRNA binding site
source                 1..9
                       mol_type = protein
                       organism = synthetic construct
SEQUENCE: 255
NRSRKPLKT                                                          9

SEQ ID NO: 256         moltype = AA  length = 9
FEATURE                Location/Qualifiers
REGION                 1..9
                       note = Mutant GRF miRNA binding site
```

```
source                  1..9
                        mol_type = protein
                        organism = synthetic construct
SEQUENCE: 256
NRSKKPVET                                                         9

SEQ ID NO: 257          moltype =   length =
SEQUENCE: 257
000

SEQ ID NO: 258          moltype =   length =
SEQUENCE: 258
000

SEQ ID NO: 259          moltype =   length =
SEQUENCE: 259
000

SEQ ID NO: 260          moltype = AA  length = 20
FEATURE                 Location/Qualifiers
source                  1..20
                        mol_type = protein
                        organism = Zea mays
SEQUENCE: 260
HMHRGRNRSR KPVETQLAPQ                                             20

SEQ ID NO: 261          moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 261
cttccacagg ctttcttgaa                                             20

SEQ ID NO: 262          moltype = DNA  length = 20
FEATURE                 Location/Qualifiers
misc_feature            1..20
                        note = Synthetic spacer
source                  1..20
                        mol_type = other DNA
                        organism = synthetic construct
SEQUENCE: 262
attccacagg ctttcttgaa                                             20

SEQ ID NO: 263          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 263
aaccgttcaa gaaagcctgt ggaaacc                                     27

SEQ ID NO: 264          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 264
aaccgttcaa gaaaacctgt ggaaacc                                     27

SEQ ID NO: 265          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 265
aaccgttcaa gaaagcctgt caaaacc                                     27

SEQ ID NO: 266          moltype = DNA  length = 27
FEATURE                 Location/Qualifiers
misc_feature            1..27
```

```
                        note = Synthetic binding site of GRF6
source                  1..27
                        mol_type = other DNA
                        organism = synthetic construct
SEQUENCE: 266
aaccgttcaa gaaaacctgt caaaacc                                        27

SEQ ID NO: 267          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 267
aaccgttcaa aaaagcctgt ggaaacc                                        27

SEQ ID NO: 268          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 268
aaccgttcaa gaaagcctgt aaaaacc                                        27

SEQ ID NO: 269          moltype = DNA  length = 27
FEATURE                 Location/Qualifiers
misc_feature            1..27
                        note = Synthetic binding site of GRF6
source                  1..27
                        mol_type = other DNA
                        organism = synthetic construct
SEQUENCE: 269
aaccgttcaa gaaaacctgt aaaaacc                                        27

SEQ ID NO: 270          moltype = DNA  length = 23
FEATURE                 Location/Qualifiers
misc_feature            1..23
                        note = Synthetic spacer
source                  1..23
                        mol_type = other DNA
                        organism = synthetic construct
SEQUENCE: 270
cacaggcttt cttgaacggt tct                                            23

SEQ ID NO: 271          moltype = DNA  length = 23
FEATURE                 Location/Qualifiers
misc_feature            1..23
                        note = Synthetic spacer
source                  1..23
                        mol_type = other DNA
                        organism = synthetic construct
SEQUENCE: 271
cacaggcttt cttgaacggt gac                                            23

SEQ ID NO: 272          moltype = DNA  length = 23
FEATURE                 Location/Qualifiers
misc_feature            1..23
                        note = Synthetic spacer
source                  1..23
                        mol_type = other DNA
                        organism = synthetic construct
SEQUENCE: 272
cacaggcttt cttgaacggt tct                                            23

SEQ ID NO: 273          moltype = DNA  length = 23
FEATURE                 Location/Qualifiers
misc_feature            1..23
                        note = Synthetic spacer
source                  1..23
                        mol_type = other DNA
                        organism = synthetic construct
SEQUENCE: 273
cacaggcttt cttgaacggt ggc                                            23

SEQ ID NO: 274          moltype = DNA  length = 23
FEATURE                 Location/Qualifiers
```

```
misc_feature           1..23
                       note = Synthetic spacer
source                 1..23
                       mol_type = other DNA
                       organism = synthetic construct
SEQUENCE: 274
cacaggcttt cttgaactgt gaa                                          23

SEQ ID NO: 275         moltype = DNA  length = 68
FEATURE                Location/Qualifiers
source                 1..68
                       mol_type = genomic DNA
                       organism = Zea mays
SEQUENCE: 275
agtactgcga gcgccacatg caccgcggcc gcaaccgttc aagaaagcct gtggaaacgc  60
agctcgcg                                                           68

SEQ ID NO: 276         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 276
agtactgcga gcgccacatg caccgcggcc gcaagaaagc ctgtggaaac gcagctcgcg  60

SEQ ID NO: 277         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 277
agtactgcga gcgccacatg caccgcggcc gagaaagcct gtggaaacgc agctcgcg    58

SEQ ID NO: 278         moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 278
agcctgtgga aacgcagctc gcg                                          23

SEQ ID NO: 279         moltype = DNA  length = 62
FEATURE                Location/Qualifiers
misc_feature           1..62
                       note = Synthetic oligonucleotide
source                 1..62
                       mol_type = other DNA
                       organism = synthetic construct
SEQUENCE: 279
agtactgcga gcgccacatg caccgcggcc gctcaagaaa gcctgtggaa acgcagctcg  60
cg                                                                 62

SEQ ID NO: 280         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 280
agtactgcga gcgccacatg caccgcggcc caagaaagcc tgtggaaacg cagctcgcg   59

SEQ ID NO: 281         moltype = DNA  length = 27
FEATURE                Location/Qualifiers
misc_feature           1..27
                       note = Synthetic oligonucleotide
source                 1..27
                       mol_type = other DNA
                       organism = synthetic construct
SEQUENCE: 281
agaaagcctg tggaaacgca gctcgcg                                      27

SEQ ID NO: 282         moltype = DNA  length = 58
```

```
FEATURE                Location/Qualifiers
misc_feature           1..58
                       note = Synthetic oligonucleotide
source                 1..58
                       mol_type = other DNA
                       organism = synthetic construct
SEQUENCE: 282
agtactgcga gcgccacatg caccgcggcc aagaaagcct gtggaaacgc agctcgcg    58

SEQ ID NO: 283         moltype = DNA  length = 61
FEATURE                Location/Qualifiers
misc_feature           1..61
                       note = Synthetic oligonucleotide
source                 1..61
                       mol_type = other DNA
                       organism = synthetic construct
SEQUENCE: 283
agtactgcga gcgccacatg caccgcggcc gtcaagaaag cctgtggaaa cgcagctcgc  60
g                                                                  61

SEQ ID NO: 284         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 284
agtactgcga gcgccacatg caccgcggcc gcaagaaagc ctgtggaaac gcagctcgcg  60

SEQ ID NO: 285         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 285
agtactgcga gcgccacatg caccgcggcc gaaagcctgt ggaaacgcag ctcgcg      56

SEQ ID NO: 286         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 286
agtactgcga gcgccacatg caccgcggcc gcaagaaagc ctgtggaaac gcagctcgcg  60

SEQ ID NO: 287         moltype = DNA  length = 40
FEATURE                Location/Qualifiers
misc_feature           1..40
                       note = Synthetic oligonucleotide
source                 1..40
                       mol_type = other DNA
                       organism = synthetic construct
SEQUENCE: 287
agtactgcga gcgccacatg caccgcggcc acggctcgcg                        40

SEQ ID NO: 288         moltype = DNA  length = 33
FEATURE                Location/Qualifiers
misc_feature           1..33
                       note = Synthetic oligonucleotide
source                 1..33
                       mol_type = other DNA
                       organism = synthetic construct
SEQUENCE: 288
agtactgcga gcgccacatg caccgcggcc gcg                               33

SEQ ID NO: 289         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 289
agtactgcga gcgccacatg caccgcggcc caagaaagcc tgtggaaacg cagctcgcg   59
```

```
SEQ ID NO: 290         moltype = DNA  length = 63
FEATURE                Location/Qualifiers
misc_feature           1..63
                       note = Synthetic oligonucleotide
source                 1..63
                       mol_type = other DNA
                       organism = synthetic construct
SEQUENCE: 290
agtactgcga gcgccacatg caccgcggcc ggttcaagaa agcctgtgga aacgcagctc  60
gcg                                                                 63

SEQ ID NO: 291         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 291
agtactgcga gcgccacatg caccgcggcc aagaaagcct gtggaaacgc agctcgcg    58

SEQ ID NO: 292         moltype = DNA  length = 67
FEATURE                Location/Qualifiers
misc_feature           1..67
                       note = Synthetic oligonucleotide
source                 1..67
                       mol_type = other DNA
                       organism = synthetic construct
SEQUENCE: 292
agtactgcga gcgccacatg caccgcggcc gcaaccgtca agaaagcctg tggaaacgca  60
gctcgcg                                                             67

SEQ ID NO: 293         moltype = DNA  length = 63
FEATURE                Location/Qualifiers
misc_feature           1..63
                       note = Synthetic oligonucleotide
source                 1..63
                       mol_type = other DNA
                       organism = synthetic construct
SEQUENCE: 293
agtactgcga gcgccacatg caccgcggcc gcttcaagaa agcctgtgga aacgcagctc  60
gcg                                                                 63

SEQ ID NO: 294         moltype = DNA  length = 39
FEATURE                Location/Qualifiers
misc_feature           1..39
                       note = Synthetic oligonucleotide
source                 1..39
                       mol_type = other DNA
                       organism = synthetic construct
SEQUENCE: 294
agtactgcga gcgccacatg caccgcggcc cagtcccaa                          39

SEQ ID NO: 295         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 295
agtactgcga gcgccacatg caccgcggcc caagaaagcc tgtggaaacg cagctcgcg   59

SEQ ID NO: 296         moltype = DNA  length = 62
FEATURE                Location/Qualifiers
misc_feature           1..62
                       note = Synthetic oligonucleotide
source                 1..62
                       mol_type = other DNA
                       organism = synthetic construct
SEQUENCE: 296
agtactgcga gcgccacatg caccgcggcc gctcaagaaa gcctgtggaa acgcagctcg  60
cg                                                                  62

SEQ ID NO: 297         moltype = DNA  length = 59
FEATURE                Location/Qualifiers
misc_feature           1..59
                       note = Synthetic oligonucleotide
```

```
source                  1..59
                        mol_type = other DNA
                        organism = synthetic construct
SEQUENCE: 297
agtactgcga gcgccacatg caccgcggcc gcaagaagcc tgtggaaacg cagctcgcg   59

SEQ ID NO: 298          moltype = DNA  length = 62
FEATURE                 Location/Qualifiers
misc_feature            1..62
                        note = Synthetic oligonucleotide
source                  1..62
                        mol_type = other DNA
                        organism = synthetic construct
SEQUENCE: 298
agtactgcga gcgccacatg caccgcggcc gcaaccgaaa gcctgtggaa acgcagctcg  60
cg                                                                 62

SEQ ID NO: 299          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 299
agtactgcga gcgccacatg caccgcggcc caagaaagcc tgtggaaacg cagctcgcg   59

SEQ ID NO: 300          moltype = DNA  length = 65
FEATURE                 Location/Qualifiers
misc_feature            1..65
                        note = Synthetic oligonucleotide
source                  1..65
                        mol_type = other DNA
                        organism = synthetic construct
SEQUENCE: 300
agtactgcga gcgccacatg caccgcggca accgttcaag aaagcctgtg gaaacgcagc  60
tcgcg                                                              65

SEQ ID NO: 301          moltype = DNA  length = 63
FEATURE                 Location/Qualifiers
misc_feature            1..63
                        note = Synthetic oligonucleotide
source                  1..63
                        mol_type = other DNA
                        organism = synthetic construct
SEQUENCE: 301
agtactgcga gcgccacatg caccgcggcc gcaacaagaa agcctgtgga aacgcagctc  60
gcg                                                                63

SEQ ID NO: 302          moltype = DNA  length = 67
FEATURE                 Location/Qualifiers
misc_feature            1..67
                        note = Synthetic oligonucleotide
source                  1..67
                        mol_type = other DNA
                        organism = synthetic construct
SEQUENCE: 302
agtactgcga gcgccacatg caccgcggcc gcaaccttca agaaagcctg tggaaacgca  60
gctcgcg                                                            67

SEQ ID NO: 303          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 303
agtactgcga gcgccacatg caccgcggcc caagaaagcc tgtggaaacg cagctcgcg   59

SEQ ID NO: 304          moltype = DNA  length = 3431
FEATURE                 Location/Qualifiers
source                  1..3431
                        mol_type = genomic DNA
                        organism = Zea mays
SEQUENCE: 304
ggagcgaagc aaagcacatc acgagcccag cctgcgcctg cggagggagg gggctcatta  60
aagaggggc gcgagcgcga ccggccgcgg ggagcaagca gcgcgcgaga gagacaggtt  120
gagatggcga tgccgtatgc ctctctttcc ccggcaggcg ccgccgacca ccgctcctcc  180
```

-continued

| | | | | | | |
|---|---|---|---|---|---|---|
| acagccacgg | cgtccctcgt | ccccttctgc | cgctccactc | cgctctccgc | gtaagtatcc | 240 |
| accaccgtcg | ctcatcgctt | cttggctcgt | gtagtgtcgt | ctcccattga | tgcccgtctg | 300 |
| gttcgcggtt | gtgttgtgac | gacgtggtgg | tatgtgtgct | ggtgcagggg | cggcgggctg | 360 |
| ggcgaggagg | acgcccaggc | gagcgcgagg | tggccggccg | cgaggccggt | ggtgccgttc | 420 |
| acgccggcgc | agtaccagga | gctggagcag | caggcgctca | tatacaagta | cctggtggcg | 480 |
| ggcgtgcccg | ttccgccgga | tctcgtggtt | ccaatccgcc | gcggcctcga | ctccctcgca | 540 |
| acccgcttct | acggccaacc | cacacgtacg | tacggcattt | ccctccctct | cctctcggcg | 600 |
| ccctgccaga | ctccatctcc | ttcctgtact | gcgtccgggg | tgcttggctg | cttgctccct | 660 |
| ccccgggatc | ctgactcttt | gtttattcca | gccaagcgta | ctttgcctcc | attagttaat | 720 |
| ttgctccagt | catttgttaa | tccctggtgc | gcgattcaag | aaccgtgcgc | gtgtttcata | 780 |
| caagaccccc | gatttgctcc | cggaaagttt | ctgttttttt | aatccgagct | gattcatcaa | 840 |
| atgatgaggc | agagctagct | aggtagctcg | tcatttcgtg | ctgttttgat | ttgataccga | 900 |
| gcttagtagt | tgttggaata | gaggttagaa | tcagtagcac | gcatcgttgt | ggctcaatag | 960 |
| tacgaatact | tttcttttgc | catttatttc | ctctccttct | ggcttctgga | tgatcaatac | 1020 |
| tacgtaactg | tgagaggtcg | ccccctcggc | agcaagcaaa | ttcattgaat | gcaatctgca | 1080 |
| gcagctctcc | gctagctgct | cgccatttcg | tccgactgcg | cctgcatcgg | tactgtcctg | 1140 |
| tactaccaaa | tggcaatcca | tttggacact | gcagatccag | atgcacgcgt | agttgctgcg | 1200 |
| tacatgcaga | tgcacgatga | taaaagcaaa | cgcacaagtg | atgcttaaat | acagcgtctg | 1260 |
| attttctcgg | cgtgatctgt | gcagtcgggt | acggaccgta | cctggggagg | aaactggatc | 1320 |
| cggagcccgg | ccggtgccgg | cgaacggacg | gcaagaagtg | gcggtgctcc | aaggaggccg | 1380 |
| ccccggactc | caagtactgc | gagcgccaca | tgcaccgcgg | ccgcaaccgt | tcaagaaagc | 1440 |
| ctgtggaaac | gcagctcgcg | ccccagtccc | aaccgcccgc | cgccgcagcc | gtctccgccg | 1500 |
| ctccgcccct | ggcagccgcc | gccgccgcca | ccaccaacgg | cagcggcttc | cagaaccact | 1560 |
| ctctctaccc | ggccatcgcc | ggcagcactg | gtggtggagg | aggagttggc | gggtccggca | 1620 |
| atatctcctc | cccgttctcc | tcgtcgatgg | ggggatcgtc | tcagctgcac | atggacagtg | 1680 |
| ctgccagcta | ctcctacgca | gctcttggtg | gtggaactgc | aaaggatctc | aggtgactat | 1740 |
| tctttccctt | ttcttttatt | tcctctccag | tgaccaatgc | tatcctgttt | ttctaacagt | 1800 |
| gctatcgatt | ttaactgatt | ggcgtcagat | ggccacacat | gctataacat | tttaccgatg | 1860 |
| atcgttcact | aatctctgtc | tgtttggcat | cagtggcaat | caaaaccagt | agcgtagtgc | 1920 |
| gtgctccgta | gtacttcact | ggcaaaatca | gcatggccta | cgaggacttt | actcacttca | 1980 |
| agagattacg | ttagagttca | ggcgctggct | ggttgcctgg | ccacgcttta | ttaatgagtt | 2040 |
| cagttctaaa | cccctgctga | agcccaggca | gtgtccatgt | ctctacgaga | tagttgtgcc | 2100 |
| cagggcaggt | ggacgtgcag | gtgtgcagcg | cacagccttg | ttggcttcgg | cacagaccca | 2160 |
| gcttcgaatt | cgtgctggtg | ctgcgcataa | agatggaact | tgtttgtgtc | cagcggtcgc | 2220 |
| agtgctggtg | cctgctgctt | gctgatgctg | tccttccctg | gccattactc | cacgtcttta | 2280 |
| tgatctcgca | ggatcaagtc | gttgctcttg | caactctttt | agggggcagc | atgtaataaa | 2340 |
| atccggtcct | tgtaactact | gataaacctg | aaacgcatca | tgctggaagt | ccatcccctt | 2400 |
| ttgcccatac | cagtttggtt | gattttactg | tacagatgtt | ctttcacttt | gtttacaatt | 2460 |
| tatcgaacag | gataatgaag | actaacacct | cacaaagaag | aaaacatact | gcagttggca | 2520 |
| tgtgtccttt | ttaacctttg | caaccccccct | actaatttgc | tgtgcccacc | ccgctttctg | 2580 |
| aaatccaggt | acaacgctta | cggaataaga | tctctggcgg | acgagcacaa | ccagctgatc | 2640 |
| gcagaagcca | tcgactcgtc | gatagagagc | cagtggcgcc | tccccagctc | gtcgttcccg | 2700 |
| ctctcgagct | acccacatct | cggggcgctg | ggcgacctgg | gcggccagaa | cagcacggtg | 2760 |
| agctcgctgc | cgaagatgga | gaagcagcag | ccgccctcgt | ccttcctagg | gaacgacacc | 2820 |
| ggggccggca | tggccatggg | ctccgcctcc | gcgaagcagg | agggccagac | gctgcggcac | 2880 |
| ttcttcgacg | agtggcccaa | ggcgcgggac | tcctggccgg | gcctctccga | cgagaccgcc | 2940 |
| agcctcgcct | cgttcccccc | ggcgacccag | ctgtcgatgt | ccatacccat | ggcgtcctcc | 3000 |
| gacttctccg | tggccagctc | ccagtcgccc | aacggtgagt | cgcgtacgtt | cctgctggcc | 3060 |
| acggaccgaa | ggtgaaaggt | tgttgctggt | ttactgatag | gagacaacca | tgtctggtct | 3120 |
| ctgcagatga | ctaatggtgc | gtggatcgtc | gcgttctggc | cctttgtctg | tcttccctcc | 3180 |
| agtcctccac | ccaccgcgca | gtagtagctg | cggaaacagc | ccatgctcct | gtatatttgt | 3240 |
| cggtcatttt | ccgtgtcaga | tctgtgtacc | aaaccaagcg | gcggcggccg | tcgtctctcc | 3300 |
| ccgcctccgc | ctcgcctcat | gtgggtgggt | gaacatgaga | ccgttttgct | taggctcaaa | 3360 |
| gctttgtgtg | accccactga | tcggttgtct | gcgtactacc | tgaaagcctg | ctgcttttgt | 3420 |
| agcattactg | t | | | | | 3431 |